United States Patent
Turley et al.

(10) Patent No.: US 10,844,102 B2
(45) Date of Patent: Nov. 24, 2020

(54) PEPTIDES, COMPOSITIONS, AND METHODS FOR STIMULATING SUBCUTANEOUS ADIPOGENESIS

(71) Applicant: The Regents of the University of California, Oakland, CA (US)

(72) Inventors: Eva A. Turley, London (CA); Seyed Bahram Bahrami, Menlo Park, CA (US); Mina J. Bissell, Berkeley, CA (US)

(73) Assignee: The Regents of the University of California, Oakland, CA (US)

( * ) Notice: Subject to any disclaimer, the term of this patent is extended or adjusted under 35 U.S.C. 154(b) by 255 days.

(21) Appl. No.: 15/313,538

(22) PCT Filed: May 28, 2015

(86) PCT No.: PCT/US2015/032952
§ 371 (c)(1),
(2) Date: Nov. 22, 2016

(87) PCT Pub. No.: WO2015/184125
PCT Pub. Date: Dec. 3, 2015

(65) Prior Publication Data
US 2018/0230188 A1    Aug. 16, 2018

Related U.S. Application Data

(60) Provisional application No. 62/004,050, filed on May 28, 2014.

(51) Int. Cl.
| | | |
|---|---|---|
| C07K 14/47 | (2006.01) |
| A61Q 19/06 | (2006.01) |
| A61Q 19/08 | (2006.01) |
| A61K 8/65 | (2006.01) |
| A61K 9/107 | (2006.01) |
| A61P 17/00 | (2006.01) |
| A61P 29/00 | (2006.01) |
| A61K 8/64 | (2006.01) |
| A61K 9/00 | (2006.01) |
| A61K 38/39 | (2006.01) |
| A61K 45/06 | (2006.01) |
| A61L 27/24 | (2006.01) |
| A61L 27/54 | (2006.01) |
| A61Q 19/00 | (2006.01) |
| A61K 38/00 | (2006.01) |

(52) U.S. Cl.
CPC ............... *C07K 14/47* (2013.01); *A61K 8/64* (2013.01); *A61K 8/65* (2013.01); *A61K 9/0014* (2013.01); *A61K 9/0019* (2013.01); *A61K 9/1075* (2013.01); *A61K 38/39* (2013.01); *A61K 45/06* (2013.01); *A61L 27/24* (2013.01); *A61L 27/54* (2013.01); *A61P 17/00* (2018.01); *A61P 29/00* (2018.01); *A61Q 19/00* (2013.01); *A61Q 19/06* (2013.01); *A61Q 19/08* (2013.01); *A61K 38/00* (2013.01); *A61L 2300/402* (2013.01); *A61L 2300/412* (2013.01); *A61L 2430/34* (2013.01)

(58) Field of Classification Search
None
See application file for complete search history.

(56) References Cited

U.S. PATENT DOCUMENTS

| | | |
|---|---|---|
| 6,127,525 A | 10/2000 | Crystal et al. |
| 6,153,432 A | 11/2000 | Halvorsen et al. |
| 6,211,149 B1 | 4/2001 | Chesebro et al. |
| 6,271,344 B1 | 8/2001 | Turley |
| 6,429,291 B1 | 8/2002 | Turley et al. |
| 6,709,864 B1 | 3/2004 | Pittenger et al. |
| 6,864,235 B1 | 3/2005 | Turley et al. |
| 6,911,429 B2 | 6/2005 | Cruz et al. |
| 7,544,661 B2 | 6/2009 | Stupp et al. |
| 7,576,052 B2 | 8/2009 | Kahn et al. |
| 8,093,217 B2 | 1/2012 | Toole et al. |
| 8,715,653 B2 | 5/2014 | Turley et al. |
| 10,494,402 B2 | 12/2019 | Turley et al. |
| 2002/0127227 A1 | 9/2002 | Holmes et al. |
| 2003/0100490 A1 | 5/2003 | Cruz et al. |
| 2003/0144329 A1 | 7/2003 | Pfahl et al. |
| 2003/0170755 A1 | 9/2003 | Schmitt et al. |
| 2003/0223997 A1 | 12/2003 | Challita-Eid et al. |
| 2004/0010812 A1 | 1/2004 | Turley et al. |
| 2004/0037834 A1 | 2/2004 | Woloski et al. |
| 2004/0171821 A1 | 9/2004 | Valenzuela et al. |
| 2004/0229219 A1 | 11/2004 | Gallaher et al. |
| 2005/0008621 A1 | 1/2005 | Kirkland et al. |

(Continued)

FOREIGN PATENT DOCUMENTS

| | | |
|---|---|---|
| CA | 2 160 603 C | 4/2003 |
| EP | 0 950 708 A2 | 10/1999 |

(Continued)

OTHER PUBLICATIONS

GenBank (<https://www.ncbi.nlm.nih.gov/protein/OHT01994.1?report=genbank&log$=protalign&blast_rank=1&RID=RZ6WUMN2015 >OHT01994.1; Oct. 25, 2016).*

(Continued)

*Primary Examiner* — James H Alstrum-Acevedo
*Assistant Examiner* — Tara L Martinez
(74) *Attorney, Agent, or Firm* — Emily M. Haliday; Weaver Austin Villeneuve & Sampson LLP

(57) ABSTRACT

Peptides that stimulate subcutaneous adipogenesis in mammals and uses thereof are provided.

22 Claims, 14 Drawing Sheets
Specification includes a Sequence Listing.

(56) References Cited

U.S. PATENT DOCUMENTS

| | | |
|---|---|---|
| 2005/0032064 A1 | 2/2005 | Staels |
| 2005/0048135 A1 | 3/2005 | Iinuma et al. |
| 2005/0058646 A1 | 3/2005 | Turley et al. |
| 2005/0164183 A1 | 7/2005 | Imagawa et al. |
| 2005/0209145 A1 | 9/2005 | Stupp et al. |
| 2007/0116669 A1 | 5/2007 | Merzouk et al. |
| 2007/0179085 A1 | 8/2007 | Savani |
| 2007/0185027 A1 | 8/2007 | Erickson et al. |
| 2007/0292869 A1 | 12/2007 | Becker et al. |
| 2008/0234183 A1 | 9/2008 | Hallbrink et al. |
| 2009/0176306 A1 | 7/2009 | Taira et al. |
| 2009/0298164 A1 | 12/2009 | Cattadoris et al. |
| 2009/0312746 A1 | 12/2009 | Khouri et al. |
| 2010/0062000 A1 | 3/2010 | Turley et al. |
| 2010/0093640 A1 | 4/2010 | Bonte et al. |
| 2010/0143382 A1 | 6/2010 | Turley et al. |
| 2010/0290989 A1 | 11/2010 | Tolg et al. |
| 2010/0323984 A1 | 12/2010 | Piccirilli et al. |
| 2011/0236411 A1 | 9/2011 | Scholler et al. |
| 2011/0288034 A1 | 11/2011 | Chada et al. |
| 2012/0076810 A1 | 3/2012 | Poland et al. |
| 2013/0224234 A1 | 8/2013 | Nakamura et al. |
| 2013/0259807 A1 | 10/2013 | Bissell et al. |
| 2014/0179616 A1 | 6/2014 | Turley et al. |
| 2015/0284433 A1 | 10/2015 | Turley et al. |

FOREIGN PATENT DOCUMENTS

| | | |
|---|---|---|
| EP | 1 158 044 A1 | 11/2001 |
| EP | 1 456 187 A1 | 9/2004 |
| EP | 1 696 945 A1 | 9/2006 |
| EP | 2 079 460 A2 | 7/2009 |
| JP | 2000-217576 A | 8/2000 |
| JP | 2000-512484 A | 9/2000 |
| JP | 2004-536819 A | 12/2004 |
| JP | 2005-525371 A | 8/2005 |
| JP | 2007-513174 A | 5/2007 |
| JP | 2010-506893 A | 3/2010 |
| WO | WO 93/021312 A1 | 10/1993 |
| WO | WO 94/016328 A1 | 7/1994 |
| WO | WO 97/024111 A2 | 7/1997 |
| WO | WO 97/38098 A1 | 10/1997 |
| WO | WO 1999/63080 * | 12/1999 |
| WO | WO 00/044882 A2 | 8/2000 |
| WO | WO 00/46348 A1 | 8/2000 |
| WO | WO 02/100428 A1 | 12/2002 |
| WO | WO 03/033535 A2 | 4/2003 |
| WO | WO 03/075858 A2 | 9/2003 |
| WO | WO 2005/018552 A2 | 3/2005 |
| WO | WO 2005/056039 A2 | 6/2005 |
| WO | WO 2006/130974 A1 | 12/2006 |
| WO | WO 2008/47061 A2 | 4/2008 |
| WO | WO 2008/140586 A2 | 11/2008 |
| WO | WO 2009/036246 * | 3/2009 |
| WO | WO 2009/061130 A2 | 5/2009 |
| WO | WO 2011/150495 A1 | 12/2011 |
| WO | WO 2012/031015 A1 | 3/2012 |
| WO | WO 2014/082042 A2 | 5/2014 |
| WO | WO 2015/184125 A1 | 12/2015 |

OTHER PUBLICATIONS

UniProt (<https://www.uniprot.org/uniprot/A0A061F9Q4> A0A061F9Q4; intergrated into UniProt Sep. 3, 2014).*
U.S. Office Action dated Jul. 12, 2019 issued in U.S. Appl. No. 14/089,445.
U.S. Notice of Allowance dated Jul. 17, 2019 in U.S. Appl. No. 14/646,298.
U.S. Office Action dated Jul. 25, 2012 issued in U.S. Appl. No. 12/515,405.
U.S. Final Office Action dated Apr. 23, 2013 issued in U.S. Appl. No. 12/515,405.
U.S. Notice of Allowance dated Dec. 16, 2013 issued in U.S. Appl. No. 12/515,405.
U.S. Office Action dated Mar. 31, 2015 issued in U.S. Appl. No. 13/818,641.
U.S. Office Action dated Jan. 5, 2015 issued in U.S. Appl. No. 14/089,445.
U.S. Final Office Action dated Sep. 24, 2015 issued in U.S. Appl. No. 14/089,445.
U.S. Office Action dated Apr. 21, 2016 issued in U.S. Appl. No. 14/089,445.
U.S. Final Office Action dated Feb. 9, 2017 issued in U.S. Appl. No. 14/089,445.
U.S0 Office Action dated Feb. 2, 2018 issued in U.S. Appl. No. 14/089,445.
U.S. Final Office Action dated Nov. 30, 2018 issued in U.S. Appl. No. 14/089,445.
U.S. Preliminary Amendment dated Nov. 2, 2015 in U.S. Appl. No. 14/646,298.
U.S. Restriction Requirement dated Mar. 15, 2016 in U.S. Appl. No. 14/646,298.
U.S. Office Action dated Jun. 9, 2016 in U.S. Appl. No. 14/646,298.
U.S. Final Office Action dated Jan. 13, 2017 in U.S. Appl. No. 14/646,298.
U.S. Office Action dated Jan. 8, 2018 in U.S. Appl. No. 14/646,298.
U.S. Office Action dated Nov. 8, 2018 in U.S. Appl. No. 14/646,298.
PCT International Search Report and Written Opinion dated Nov. 7, 2008 issued in PCT/US2007/085453.
PCT International Preliminary Report on Patentability dated May 26, 2009 issued in PCT/US2007/085453.
Australian Examination Report dated Apr. 23, 2012 issued in AU2007353332.
Canadian Examination Report dated Aug. 5, 2014 issued in CA 2,670,320.
Canadian Examination Report dated Jul. 8, 2015 issued in CA 2,670,320.
Canadian Examination Report dated Jun. 28, 2016 issued in CA 2,670,320.
European Supplemental Search Report dated Mar. 4, 2010 issued in EP 07 874 313.5.
European Examination Report dated Jun. 21, 2010 issued in EP 07 874 313.5.
European Examination Report dated Nov. 15, 2011 issued in EP 07 874 313.5.
European Examination Report dated Sep. 10, 2013 issued in EP 07 874 313.5.
European Examination Report dated Jul. 22, 2015 issued in EP 07 874 313.5.
European Examination Report dated Feb. 23, 2016 issued in EP 07 874 313.5.
European response to the communication pursuant to Article 94(3) EPC dated Feb. 23, 2016 in EP 07 874 313.5 dated Aug. 23, 2016.
European Communication dated Oct. 27, 2016 issued in EP 07 874 313.5.
European Partial Search Report dated Feb. 11, 2013 issued in EP 12 172 124.5.
European Extended Search Report dated Jun. 5, 2013 issued in EP 12 172 124.5.
European Examination Report dated Jul. 18, 2014 issued in EP 12 172 124.5.
PCT International Search Report and Written Opinion dated Jan. 4, 2012 issued in PCT/US2011/050054.
PCT International Preliminary Report on Patentability dated Mar. 5, 2013 issued in PCT/US2011/050054.
Extended European Search Report dated Mar. 5, 2014 issued in EP 11 822 599.4.
European Office Action dated Feb. 25, 2015 issued in EP 11 822 599.4.
Japanese Office Action dated Aug. 3, 2015 issued in JP 2013-527285.
PCT Invitation to Pay Additional Fees dated Feb. 3, 2014 issued in PCT/US2013/071719.
PCT International Search Report and Written Opinion dated May 26, 2014 issued in PCT/US2013/071719.

(56) References Cited

OTHER PUBLICATIONS

PCT International Preliminary Report on Patentability dated Jun. 4, 2015 issued in PCT/US2013/071719.
Chinese Office Action dated Aug. 3, 2017 issued in CN 201380061413.4.
Israel Office Action dated Aug. 15, 2018 issued in IL 239008.
European Office Action dated Jun. 23, 2016 issued in EP 13 802 811.3.
European response to the communication pursuant to Article 94(3) EPC dated Jun. 23, 2016 in EP 13 802 811.3 dated Dec. 30, 2016.
Japanese Office Action dated Aug. 8, 2017 issued in JP 2015-544173.
PCT International Search Report and Written Opinion dated Aug. 24, 2015 issued in PCT/US2015/032952.
PCT International Preliminary Report on Patentability dated Nov. 29, 2016 issued in PCT/US2015/032952.
Database Geneseq [Online] (Dec. 18, 2003) "RHAMM/Erk 1 competitive binding peptide D5.", XP-002718746, retrieved from EBI accession No. GSP:ADC02454 Database accession No. ADC02454; One Page.
Database Geneseq [Online] (May 19, 2005) "Heparin binding protein associated amino acid sequence, SEQ ID No. 65.", XP-002718747, retrieved from EBI accession No. GSP:ADY52132 Database accession No. ADY52132; One Page.
Database Geneseq [Online] (Feb. 17, 2011) "Structural peptide SEQ ID No. 23563.", XP-002718745, retrieved from EBI accession No. GSP:AJG37689 Database accession No. AJG37689; One Page.
GeneBank Accession No. CAI75473.1 [Online] (retrieved on Jan. 16, 2018) "hypothetical protein, conserved [*Theileria annulata*]—Protein—NCBI", Retrieved from the Internet: https://www.ncbi.nlm.nih.gov/protein/CAI75473, 3 Pages.
GeneBank Accession No. ARB15206 [Online] (retrieved on Oct. 29, 2018) "hypothetical protein Ccr32_gp288 [Caulobacter phage Ccr32]—Protein—NCBI]", Retrieved from the Internet: https://www.ncbi.nlm.nih.gov/protein/arb15206, 1 Page.
Sequence Listing for WO 2011/150495 (PCT/CA2011/000613) published on Dec. 8, 2011, 16 Pages.
"Peptide Modifications" (Oct. 2007) *Genscript peptide modification*, 2 pages.
Adamia et al. (2005) "Hyaluronan and hyaluronan synthases: potential therapeutic targets in cancer," *Curr Drug Targets Cardiovasc Haematol Disord*, 5:3-14.
Aitken et al. (2001) "Stretch-Induced Bladder Smooth Muscle Cell (SMC) Proliferation Is Mediated by RHAMM Dependent Extracellular-Regulated Kinase (erk) Signaling," *Urology*, 57(Supp 6A):109.
Assmann et al. (1998) "The human hyaluronan receptor RHAMM is expressed as an intracellular protein in breast cancer cells," *Journal of Cell Science*, 111(12):1685-94.
Assmann et al. (1999) "The intracellular hyaluronan receptor RHAMM/IHABP interacts with microtubules and actin filaments," *Journal of Cell Science*, 112:3943-3954.
Babish et al. (2010) "Antidiabetic Screening of Commercial Botanical Products in 3T3-L1 Adipocytes and *db/db* Mice," *Journal of Medicinal Food*, 13(3):535-547.
Bissell (2001) "Chronic liver injury, TGF-beta, and cancer," *Exp Mol Med*, 33:179-190.
Bost et al. (2005) "The extracellular signal-regulated kinase isoform ERK1 is specifically required for in vitro and in vivo adipogenesis." *Diabetes*, 54(2):402-11.
Cheon et al. (2002) "β-Catenin stabilization dysregulates mesenchymal cell proliferation, motility, and invasiveness and causes aggressive fibromatosis and hyperplastic cutaneous wounds," *Proc. Natl. Acad. Sci.*, 99(10):6973-6978.
Cheung et al. (1999) "Receptor for hyaluronan mediated motility (RHAMM), a hyaladherin that regulates cell responses to growth factors," *Biochem Soc Trans*, 27:135-142.
Choi et al. (Mar. 2003) "The Role of Ghrelin and Growth Hormone Secretagogues Receptor on Rat Adipogenesis," *Endocrinology*, 144(3):754-759.

Domaszewska et al. (2006) "Dermal keratinocytes—protective mechanical, biochemical and immune functions related to grafting," *Ann. Transplnt.*, 11(4):45-52.
Esguerra et al. (2010) "Tubulin derived peptides as optical imaging probes targeting RHAMM," *The Journal of Nuclear Medicine*, 51 (Supplement 2):394; Abstract No. 394; Downloaded from Internet http://jnumedmtg.snmjournals.org/cgi/content/meeting_abstract/51/2_Meeting Abstracts/394 on Aug. 14, 2013; 2 pages.
Evanko et al. (Nov. 10, 2007) "Hyaluronan-Dependent Pericellular Matrix" *Adv Drug Deliv Rev.*, 59(13):1351-1365; NIH Public Access Author Manuscript; available in PMC Jan. 3, 2008; 30 pages.
Feldman et al. (1998) "Anti-TNF alpha therapy is useful in rheumatoid arthritis and Crohn's disease: analysis of the mechanism of action predicts utility in other disease," *Transplant. Proc.*, 30:4126-4127.
Fu et al. (2006) "Enhanced wound-healing quality with bone marrow mesenchymal stem cells autografting after skin injury," *Wound Repair Regen*, 14:325-335.
Fukumura et al. (2003) "Paracrine regulation of angiogenesis and adipocyte differentiation during vivo adipogenesis," *Circulation Research*, 93(9):E88-E97.
Greiner et al. (2005) "RHAMM/CD168-R3 Peptide Vaccination of HLA-A2+ Patients with Acute Myeloid Leukemia (AML), Myelodysplastic Syndrome (MDS) and Multiple Myeloma (MM)," *Blood*, 106: Abstract 2781; One Page.
Greiner et al. (Aug. 1, 2005) "Identification and characterization of epitopes of the receptor for hyaluronic acid—mediated motility (RHAMM/CD168) recognized by $CD8^+T$ cells of HLA-A2—positive patients with acute myeloid leukemia," *BLOOD*, 106(3):938-945.
Hall et al. (1995) "Overexpression of the hyaluronan receptor RHAMM is transforming and is also required for H-ras transformation," *Cell*, 82:19-28.
Hall et al. (1996) "pp60(c-src) is required for cell locomotion regulated by the hyaluronanreceptor RHAMM," *Oncogene*, 13:2213-2224.
Hall et al. (2001) "Fibroblasts require protein kinase C activation to respond to hyaluronan with increased locomotion," *Matrix Biol*, 20:183-192.
Hardwick et al. (1992) "Molecular cloning of a novel hyaluronan receptor that mediates tumor cell motility," *J Cell Biol.*, 117(6):1343-1350.
Huang et al. (2004) "MAP kinases and cell migration," *J Cell Sci*, 117:4619-4628.
Ji et al. (2013) "Inhibition of adipogenesis in 3T3-L1 cells and suppression of abdominal fat accumulation in high-fat diet-feeding C57BL/6J mice after downregulation of hyaluronic acid" *Int. J. Obes. (Lond.)*, 1035-1043.
Kang et al. (2013) "Hyaluronan accumulates with high-fat feeding and contributes to insulin resistance." *Diabetes*, 62(6):1888-96.
Kaya et al. (1997) "Selective suppression of CD44 in keratinocytes of mice bearing an antisense CD44 transgene driven by a tissue-specific promoter disrupts hyaluronate metabolism in the skin and impairs keratinocyte proliferation," *Genes and Development*, 11(8):996-1007.
Kim et al. (2014) "Adipose-derived stem cell-containing hyaluronic acid/alginate hydrogel improves vocal fold wound healing." *Laryngoscope*, 124(3):E64-72.
Lee et al. (2010) "A functional role for the p62-ERK1 axis in the control of energy homeostasis and adipogenesis." *EMBO Rep.*, 11(3):226-32.
Li et al. (2006) "Adult bone-marrow-derived mesenchymal stem cells contribute to wound healing of skin appendages," *Cell Tissue Res*, 326(3):725-736.
Liu et al. (2012) "ANKRD26 and Its Interacting Partners TRIO, GPS2, HMMR and DIPA Regulate Adipogenesis in 3T3-L1 Cells" *PloS One*, 7(5):e38130 [10 pages].
Lovvorn et al. (1998) "Hyaluronan receptor expression increases in fetal excisional skin wounds and correlates with fibroplasia," *J Pediatr Surg*, 33:1062-1069.
Mansilla et al. (2006) "Bloodstream cells phenotypically identifical to human mesenchymal bone marrow stem cells circulate in large

(56) References Cited

OTHER PUBLICATIONS amounts under the influence of acute large skin damage: new evidence for their use in regenerative medicine," *Transplant Proc*, 38:967-969.
Maxwell et al. (2003) "RHAMM Is a Centrosomal Protein That Interacts with Dynein and Maintains Spindle Pole Stability," *Molecular Biology of the Cell*, 14:2262-2276.
Maxwell et al. (2008) "Cell-surface and mitotic-spindle RHAMM: moonlighting or dual oncogenic functions?" *J. Cell. Sci.* 121(Pt 7):925-32.
Mestas et al. (2004) "Of Mice and Not Men: Differences between Mouse and Human Immunology," *Journal of Immunology*, 172:2731-2738.
Moreno-Navarrete et al. (2012) "Adipocyte Differentiation," *Adipose Tissue Biology Chapter 2*, 23 Pages, DOI 10.1007/978-1-4614-0965-6_2.
Mummert et al. (2000) "Development of a Peptide Inhibitor of Hyaluronan-Mediated Leukocyte Trafficking," *The Journal of Experimental Medicine*, 192(6):769-779.
Nedvetzki et al. (2004) "RHAMM, a receptor for hyaluronan-mediated motility, compensates for CD44 in inflamed CD44-knockout mice: A different interpretation of redundancy," *Proc. Natl. Acad. Sci. USA*, 101:18081-18086.
Nickel (2005) "Unconventional secretory routes: direct protein export across the plasma membrane of mammalian cells," *Traffic*, 6:607-614.
Niemelä et al. (2008) "Adipose Tissue and Adipocyte Differentiation: Molecular and Cellular Aspects and Tissue Engineering Applications," *Topics in Tissue Engineering, vol. 4. Eds. N. Asham makhi, R Reis, & F Chiellini*, 26 Pages.
Park et al. (2000) "The influence of the microenvironment on the malignant phenotype," *Mol Med Today*, 6:324-329.
Peer et al. (2004) "Tumor-Targeted Hyaluronan Nanoliposomes Increase the Antitumor Activity of Liposomal Doxorubicin in Syngeneic and Human Xenograft Mouse Tumor Models," *Neoplasia*, 6(4):343-353.
Piccinno et al. (2013) "Adipose stromal/stem cells assist fat transplantation reducing necrosis and increasing graft performance" *Apoptosis*, 18(10):1274-89.
Providence et al. (2004) "PAI-1 expression is required for epithelial cell migration in two distinct phases of in vitro wound repair," *J Cell Physiol*, 200:297-308.
Reid et al. (2004) "The future of wound healing: pursuing surgical models in transgenic and knockout mice," *J Am Coll Surg*, 199:578-585.
Samuel et al. (1993) "TGF-beta 1 stimulation of cell locomotion utilizes the hyaluronan receptor RHAMM and hyaluronan," *J Cell Biol*, 123:749-758.
Savani et al. (1995) "Migration of bovine aortic smooth muscle cells after wounding injury. The role of hyaluronan and RHAMM," *J Clin Invest*, 95:1158-1168.
Savani et al. (2000) "A Role for Hyaluronan in Macrophage Accumulation and Collagen Deposition after Bleomycin-Induced Lung Injury," *Am. J. Respir. Cell Mol. Biol.*, 23:475-484.
Schmits et al. (1997) "CD44 regulates hematopoietic progenitor distribution, granuloma formation, and tumorigenicity," *Blood*, 90:2217-2233.
Shoham et al. (2013) "The mechanics of hyaluronic acid/adipic acid dihydrazide hydrogel: towards developing a vessel for delivery of preadipocytes to native tissues." *J. Mech. Behav. Biomed. Mater.*, 28:320-31.
Shumakov (2003) "Mesenchymal bone marrow stem cells more effectively stimulate regeneration of deep burn wounds than embryonic fibroblasts," *Bull Exp Biol Med*, 136(2):192-195.
Tammi et al. (2002) "Hyaluronan and homeostasis: a balancing act," *J Biol Chem*, 277:4581-4584.
Tolg et al. (2006) "RHAMM −/− fiibroblasts are defective in CD44-mediated ERK1, 2 motogenic signaling, leading to defective skin wound repair," *J Cell Biol*, 175(6):1017-1028.
Tolg et al. (2010) "RHAMM Promotes Interphase Microtubule Instability and Mitotic Spindle Integrity through MEK1/ERK1/2 Activity" *J. Biol. Chem.*, 285(34):26461-74.
Tolg et al. (Oct. 2003) "Genetic deletion of receptor for hyaluronan-mediated motility (Rhamm) attenuates the formation of aggressive fibromatosis (desmoid tumor)," *Oncogene*, 22(44):6873-6882.
Tolg et al. (Oct. 2012) "A RHAMM Mimetic Peptide Blocks Hyaluronan Signaling and Reduces Inflammation and Fibrogenesis in Excisional Skin Wounds," *The American Journal of Pathology*, 181(4):1250-1270; With supplemental Figures 1-5 and supplemental Table S1; Total 27 pages.
Toole (2004) "Hyaluronan: from extracellular glue to pericellular cue," *Nat Rev Cancer*, 4:528-539.
Tschöp et al. (Oct. 2000) "Ghrelin induces adiposity in rodents," *Nature*, 407(6806):908-913.
Tufveson et al. (1993) "New Immunosuppressants: Testing and Development in Animal Models and the Clinic: with Special Reference to DSG," *Immunological Reviews*, 136(1):99-109.
Turley (1982) "Purification of a hyaluronate-binding protein fraction that modifies cell social behavior," *Biochem Biophys Res Commun*, 108:1016-1024.
Turley et al. (2002) "Signaling properties of hyaluronan receptors," *J Biol Chem*, 277(7):4589-4592.
Turley et al. (Jan. 1993) "Expression and Function of a Receptor for Hyaluronan-Mediated Motility on Normal and Malignant B Lymphocytes," *BLOOD*, 81(2):446-453.
Veiseh et al. (2014) "Cellular heterogeneity profiling by hyaluronan probes reveals an invasive but slow-growing breast tumor subset" *Proc. Natl. Acad. Sci. U S A.*, 111(17):E1731-9.
Wang et al. (2014) "Hyperglycemia Diverts Dividing Osteoblastic Precursor Cells to an Adipogenic Pathway and Induces Synthesis of a Hyaluronan Matrix That Is Adhesive for Monocytes" *J. Biol. Chem.*, 289(16):11410-20.
Yang et al. (1993) "Identification of Two Hyaluronan-binding Domains in the Hyaluronan Receptor RHAMM," *The Journal of Biological Chemistry*, 268(12):8617-8623.
Yang et al. (1994) "Identification of a common hyaluronan binding motif in the hyaluronan binding proteins RHAMM, CD44 and link protein," *The EMBO Journal*, 13(2):286-296.
Yusufoglu et al. (Dec. 2008) "Bioinspired synthesis of self-assembled calcium phosphate nanocomposites using block copolymer-peptide conjugates," *J. Mater. Res.*, 23(12):3196-3212.
Zhang et al. (1998) "The hyaluronan receptor RHAMM regulates extracellular-regulated kinase," *J Biol Chem*, 273:11342-11348.
Ziebell et al. (2004) "Interactions of peptide mimics of hyaluronic acid with the receptor for hyaluronan mediated motility (RHAMM)," *Journal of Computer-Aided Molecular Design*, 18(10):597-614.

\* cited by examiner

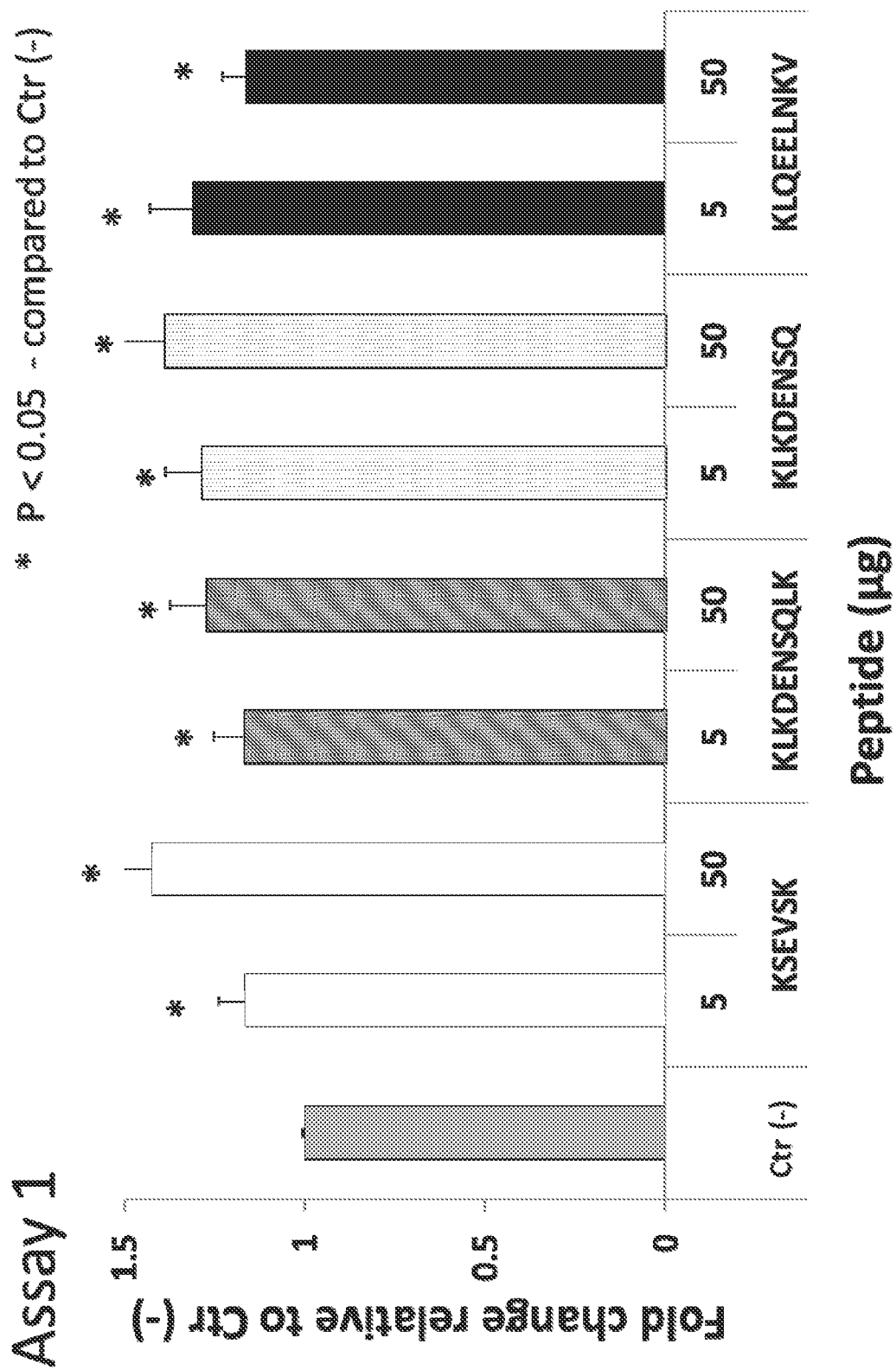

Fig. 4

AKQKIHVVKLKDENSQLKSEVSKLRCQLAKKQSETKLQEELNKVLGIKH (SEQ ID NO: 4)

FIG. 8

PEPTIDES, COMPOSITIONS, AND METHODS FOR STIMULATING SUBCUTANEOUS ADIPOGENESIS

REFERENCE TO RELATED APPLICATIONS

This application is a U.S. 371 National Phase of PCT/US2015/032952, filed on May 28, 2015, which claims the benefit of U.S. Provisional Application Ser. No. 62/004,050, filed on May 28, 2014, the entire contents of which are hereby incorporated by reference.

STATEMENT OF GOVERNMENTAL SUPPORT

This invention was made with government support under Contract No. DE-AC02-05CH11231 awarded by the U.S. Department of Energy.

FIELD OF THE INVENTION

The present invention generally relates to peptides that stimulate subcutaneous adipogenesis. The invention also relates to pharmaceutical and cosmetic compositions containing such peptides, and to various methods of using such peptides and compositions to reduce scarring or fibrosis, improve the appearance of skin, improve tissue volume, smooth skin, recruit stem cells to the formation of subcutaneous fat, reconstruct tissue, and reduce heel pain.

BACKGROUND OF THE INVENTION

RHAMM is an hyaluronan (HA)-binding protein that is either poorly expressed or not expressed in most normal adult tissues but is highly expressed in aggressive human tumors (Adamia et al. (2005) *Curr. Drug Targets Cardiovasc. Haematol. Disord.,* 5: 3-14; Tammi et al. (2002) *J. Biol. Chem.* 277: 4581-4584; Toole (2004) *Nat. Rev. Cancer,* 4: 528-539). RHAMM (gene name HMMR) is the Receptor for Hyaluronic Acid Mediated Motility, also known as CD168. RHAMM is a non-integral cell surface protein (CD168) and an intracellular hyaluronan binding protein. Analyses of animal models suggest roles for RHAMM in tumorigenesis and in other disease processes such as arthritis, consistent with its well-documented in vitro functions in cell migration and proliferation and apoptosis (Turley et al. (2002) *J. Biol. Chem.,* 277: 4589-4592). Although cell migration and proliferation and apoptosis are essential functions for morphogenesis and tissue homeostasis, genetic deletion of RHAMM does not appear to affect embryogenesis or adult homeostasis (Tolg et al. (2003) *Oncogene* 22: 6873-6882). To date, a primary physiological function for RHAMM has remained elusive.

RHAMM was originally isolated from subconfluent migrating fibroblasts in vitro (Turley (1982) *Biochem. Biophys. Res. Commun.* 108: 1016-1024) and subsequently cloned from mesenchymal cells (see, e.g., Hardwick et al. (1992) J. Cell Biol., 117: 1343-1350). Since antibodies prepared against a shed form of RHAMM blocked HA-stimulated-fibroblast motility, RHAMM was originally described as a cell surface protein that can transduce motogenic signaling pathways in culture (Turley et al. (2002) J. Biol. Chem. 277: 4589-4592). However, HA-bound RHAMM was later detected in intracellular compartments such as the actin and microtubule cytoskeletons, nucleus and cytoplasm (Adamia et al. (2005) *Curr. Drug Targets Cardiovasc. Haematol. Disord.,* 5: 3-14). More recently, RHAMM has been shown to decorate centrosomes and mitotic spindles. RHAMM appears to be required for mitotic spindle formation in culture and acts on the BRCA1/BARD1 pathway to regulate mitotic spindle integrity (Joukov et al. (2006) *Cancer Cell,* 127: 539-52). Collectively, these results suggest that RHAMM may have both extracellular and intracellular functions, (Nickel (2005) *Traffic* 6: 607-614; Samuel et al. (1993) *J. Cell Biol.,* 123: 749-758; Zhang et al. (1998) *J. Biol. Chem.,* 273: 11342-11348) thus resembling a group of proteins including epimorphin/syntaxin-2, and autocrine motility factor/phosphoglucose isomerase that are also found at the cell surface where they transmit signals across the cell membrane even though, like RHAMM, they lack both Golgi-ER export peptides and membrane spanning sequences (Nickel (2005) *Traffic* 6: 607-614).

Although the intracellular versus extracellular functions of RHAMM have not yet been clearly dissected, accumulating data suggest that both forms may contribute to mesenchymal phenotypes, at least during disease. For example, RHAMM expression in culture is increased in transformed fibroblasts by fibrogenic cytokines such as TGF-β (Samuel et al. (1993) *J. Cell Biol.,* 123: 749-758). Cell surface RHAMM is required for activation through fibrogenic cytokines such as PDGF (Zhang et al. (1998) *J. Biol. Chem.,* 273: 11342-11348). It has also been demonstrated that RHAMM expression is high in clinically aggressive mesenchymal tumors (fibromatoses or desmoid tumors) (see, e.g., Tolg et al. (2003) *Oncogene* 22: 6873-6882). In a mouse model susceptible to desmoid and upper intestinal tract tumors, genetic deletion of RHAMM strongly reduces desmoid initiation and invasion but not upper intestinal tract tumors. Fibroproliferative processes such as aggressive fibromatosis resemble proliferative/migratory stages of wound healing (Cheon et al. (2002) *Proc. Natl. Acad. Sci. USA,* 99: 6973-6978). Furthermore, the expression of RHAMM is modulated during wounding (Lovvorn et al. (1998) *J. Pediatr. Surg.,* 33: 1062-1069; discussion 1069-1070).

It has been found that factors that regulate fibroblast function play dual roles in wound repair and tumorigenesis (Bissell (2001) *Exp. Mol. Med.,* 33: 179-190; Park et al. (2000) *Mol. Med. Today,* 6: 324-329) and mesenchymal stem cell trafficking/differentiation into wound sites has become a topic of study (see, e.g., Fu et al. (2006) *Wound Repair Regen.,* 14: 325-35; Mansilla et al. (2006) *Transplant Proc.* 38: 967-969; Shumakov (2003) *Bull. Exp. Biol. Med.,* 136: 192-195). Mesenchymal stem cells and resident fibroblasts in wounds have immune-modulatory functions that affect the timing and extent of fibrosis during wound repair (Domaszewska and Oszewski (2006) *Ann. Transplnt.* 11: 45-52).

Genetic loss of RHAMM or blocking RHAMM function using peptides mimicking its hyaluronan binding sequence or antibodies to this sequence have been shown to promote subcutaneous adipogenesis. One such peptide (STMMSR-SHKTRSHHV (SEQ ID NO: 1), P-1 peptide, also referred to herein as peptide P15-1) isolated from a random phage library has been shown to bind to hyaluronan, is adipogenic and resembles the hyaluronan binding region of RHAMM, a mesenchymal factor involved in wound repair. Another peptide, peptide B (KLKDENSQLKSEVSK (SEQ ID NO: 2)), which contains several key residues required for an interaction of RHAMM with HA, is strongly adipogenic. It was reported in PCT Publication No. WO 2008/140586 that RHAMM displays an effect in modulation of adipose tissue development. In particular, histology analysis of tissue sections through unwounded skin of RHAMM−/− mice showed that the subcutaneous layer of fat was two to three times thicker than in wild-type littermate skin and fibroblasts grown from RHAMM−/− wounds incorporated high levels of fat droplets and reduced smooth muscle actin. Furthermore, RHAMM−/− dermal fibroblasts converted to adipocytes when grown in adipogenic medium. In contrast fibroblasts grown from litter matched wild-type wounds did not exhibit fat droplets, and expressed abundant smooth muscle actin. RHAMM-rescued dermal fibroblasts do not undergo adipogenic conversion when grown in adipogenic medium. Conversely, image analysis of RHAMM−/− mice showed that they have significantly less visceral fat and a lower bone density than wild-type litter mates. These data were said to indicate that RHAMM has a differential effect on visceral vs. subcutaneous adipogenesis.

It is also believed that RHAMM is selective in its regulation of subcutaneous vs. visceral fat, and that this regulation is associated with effects on bone marrow stem cells since bone density provides a measure of stem cell activity. This indicates that RHAMM affects subcutaneous fat deposition through its ability to regulate mesenchymal stem cell differentiation, a conclusion substantiated by the effect of RHAMM loss on another mesenchymal stem cell type, myofibroblasts. Furthermore, hyaluronan/RHAMM interactions play a role in this effect on mesenchymal differentiation since HA binding peptides also promote adipogenesis. In addition to these in vivo effects, RHAMM−/− dermal fibroblasts spontaneously develop into adipocytes when cultures become crowded while wild type dermal fibroblasts do not.

The mechanisms by which RHAMM promotes adipogenesis are currently not known. However it is unusual in that either blocking its function or ablating its expression promotes subcutaneous adipogenesis but reduces visceral adipogenesis. Many of the factors that are studied for their adipogenic effect (e.g. ERK1, PPAR-gamma) affect both subcutaneous and visceral adipogenesis. However, there are important differences between these two fat depots. They arise from different cell types and from different stimuli. For example, visceral fat occurs from transdifferentiation of resident fibroblasts and monocytes into adipocytes as a result of high fat diets for example, while subcutaneous fat occurs from resident pre-adipogenic fat cells and multipotential skin fibroblasts and is increased in response to chronic exposure to cold temperatures or altered as a result of aging. Visceral and subcutaneous fat depots also exhibit quite distinct phenotypic profiles. For example, visceral fat produces some pro-inflammatory cytokines, which are absent in subcutaneous depots and visceral fat is generally insulin insensitive while subcutaneous fat is generally insulin sensitive.

RHAMM may exhibit differential effects on these two fat depots through its HA receptor functions, association with adipogenic proteins (Liu et al., *PloS One*, 2012; 7(5): e38130; Tolg et al., *J. Biol. Chem.*, 2010; 285(34):26461-74) and/or action on insulin signaling pathways.

HA has recently been linked to adipogenesis through its effects on stem cell differentiation (Shoham et al., *J. Mech. Behav. Biomed. Mater.*, 2013; 28:320-31; Wang et al., *J. Biol. Chem.*, 2014; 289(16):11410-20; Kim et al., *Laryngoscope*, 2014; 124(3):E64-72; Piccinno et al., *Apoptosis*, 2013; 18(10):1274-89) in high glucose environments (Wang et al., *J. Biol. Chem.*, 2014; 289(16):11410-20). Furthermore, its accumulation in tissues promotes visceral adipogenesis (Ji et al., *Int. J. Obes.* (Lond.), 2013) and insulin resistance (Kang et al., *Diabetes*, 2013; 62(6):1888-96) but examination of data presented in these reports (Ji et al., *Int. J. Obes.* (Lond.), 2013; Kang et al., *Diabetes*, 2013; 62(6): 1888-96) suggest it has no effect on subcutaneous fat depots. RHAMM is an HA receptor that is involved in regulating the intracellular trafficking and signaling of HA and (Veiseh et al., *Proc. Natl. Acad. Sci. U.S.A.*, 2014; 111(17):E1731-9) RHAMM loss is therefore expected to disrupt ability of HA to promote visceral fat formation. Loss of RHAMM function will also reduce visceral adipogenesis. However, RHAMM is a multifunctional protein (Maxwell et al., *J. Cell. Sci.* 2008; 121(Pt 7):925-32) that exhibits HA-independent effects and the opposite is true for its regulation of subcutaneous fat deposition. For example, RHAMM binds to ERK1 (Tolg et al., *J. Biol. Chem.*, 2010; 285(34):26461-74), a map kinase that regulates adipogenesis in culture and in vivo (Lee et al., *EMBO Rep.*, 2010; 11(3):226-32; Bost et al., *Diabetes*, 2005; 54(2):402-11) as well as to ANKRD26, TRIO, GPS2 and DIA (Liu et al., *PloS One*, 2012; 7(5): e38130). When the expression of these proteins is suppressed, adipogenesis occurs. This is consistent with previous experimental data (e.g., in PCT Publication No. WO 2008/140586), indicating RHAMM function or expression may also need to be suppressed in order to promote subcutaneous adipogenesis: these proteins are likely to be part of the RHAMM signaling network that must be downregulated in order for subcutaneous adipogenesis to occur.

SUMMARY OF THE INVENTION

A peptide is provided. The peptide has a length of 7 to 13 amino acids and comprises the sequence (I): $X^1$-$X^2$-$X^3$-$X^4$-$X^5$-$X^6$-$X^7$, wherein $X^1$ is lysine (K) or arginine (R); $X^2$ is any amino acid; $X^3$ is arginine (R); $X^4$ is serine (S) or alanine (A); $X^5$ is histidine (H); $X^6$ is histidine (H); and $X^7$ is valine (V). The peptide optionally comprises a cysteine (C) residue inserted between $X^4$ and $X^5$, or a threonine (T) followed by an alanine (A) inserted between $X^5$ and $X^6$.

Another peptide is also provided. The peptide has a length of 7 to 14 amino acids and comprises the sequence (II): $X^1$-$X^2$-$X^3$-$X^4$-$X^5$-$X^6$-$X^7$, wherein $X^1$ is lysine (K) or arginine (R); $X^2$ is any amino acid; $X^3$ is arginine (R); $X^4$ is serine (S) or alanine (A); $X^5$ is histidine (H); $X^6$ is histidine (H); and $X^7$ is valine (V). The peptide optionally comprises a cysteine (C) residue inserted between $X^4$ and $X^5$, or a threonine (T) followed by an alanine (A) inserted between $X^5$ and $X^6$. When the length of the peptide is 14 amino acids, the peptide does not comprise a serine (S) residue at its amino terminus.

Preferably, the amino acid sequence (I) or (II) consists of KTRSHHV (SEQ ID NO: 6), KTRSHTAHV (SEQ ID NO: 63), RTRSHHV (SEQ ID NO: 64), KARSHHV (SEQ ID NO: 66), KSRSHHV (SEQ ID NO: 67), KIRSHHV (SEQ ID NO: 68), KNRSHHV (SEQ ID NO: 69), KPRSHHV (SEQ ID NO: 70), KDRSHHV (SEQ ID NO: 72), KKRSHHV (SEQ ID NO: 73), KQRSHHV (SEQ ID NO: 74), KERSHHV (SEQ ID NO: 75), KLRSHHV (SEQ ID NO: 76), KVRSHHV (SEQ ID NO: 77), KRRSHHV (SEQ ID NO: 83), KTRAHHV (SEQ ID NO: 87), KTRSCHHV (SEQ ID NO: 111), HKTRSHHV (SEQ ID NO: 112), SHKTRSHHV (SEQ ID NO: 113), RSHKTRSHHV (SEQ ID NO: 114), SRSHKTRSHHV (SEQ ID NO: 115), MSRSHKTRSHHV (SEQ ID NO: 116), MMSRSHKTRSHHV (SEQ ID NO: 117), or TMMSRSHKTRSHHV (SEQ ID NO: 118).

Yet another peptide is also provided. The peptide has a length of 7 to 14 amino acids and comprises the sequence (III): $Z^1$-$Z^2$-$Z^3$-$Z^4$-$Z^5$-$Z^6$-$Z^7$-$Z^8$-$Z^9$-$Z^{10}$, wherein $Z^1$ is lysine (K), alanine (A), or absent; $Z^2$ is leucine (L), isoleucine (I), alanine (A), or valine (V); $Z^3$ is lysine (K), glutamine (Q), arginine (R), glutamic acid (E), valine (V), or alanine (A); $Z^4$ is a negatively charged amino acid, threonine (T), asparagine (N), isoleucine (I), valine (V), alanine (A), tryptophan (Y), glutamine (Q), or glycine (G); $Z^5$ is a negatively charged amino acid, leucine (L), glutamine (Q), lysine (K), or alanine (A); $Z^6$ is asparagine (N), leucine (L), serine (S), glutamic acid (E), isoleucine (I), glutamine (Q), threonine (T), valine (V), lysine (K), or alanine (A); $Z^7$ is any amino acid; $Z^8$ is glutamine (Q) or lysine (K); $Z^9$ is leucine (L), valine (V), isoleucine (I), glycine (G), alanine (A), or is absent; and $Z^{10}$ is lysine (K), arginine (R), alanine (A), glutamic acid (E) or is absent. When $Z^6$ is leucine (L), $Z^9$ is not valine (V). When $Z^9$ is valine (V), $Z^6$ is not leucine (L). When the length of the peptide is 14 amino acids, $Z^1$ is lysine (K). When $Z^{10}$ is arginine (R), one of $Z^2$, $Z^3$, $Z^4$, $Z^5$, $Z^6$, $Z^7$, or $Z^9$ is alanine (A). The peptide optionally comprises an aspartic acid residue (D) inserted between $Z_4$ and $Z_5$, or a glutamine residue (Q) inserted between $Z_5$ and $Z_6$.

A further peptide is also provided. The peptide has a length of 7 to 14 amino acids and comprises the sequence (IV): $Z^1$-$Z^2$-$Z^3$-$Z^4$-$Z^5$-$Z^6$-$Z^7$-$Z^8$-$Z^9$-$Z^{10}$, wherein $Z^1$ is lysine (K), alanine (A), or absent; $Z^2$ is leucine (L), isoleucine (I), alanine (A), or valine (V); $Z^3$ is lysine (K), glutamine (Q), arginine (R), glutamic acid (E), or valine (V), or alanine (A); $Z^4$ is a negatively charged amino acid, threonine (T), asparagine (N), isoleucine (I), valine (V), alanine (A), tryptophan (Y), glutamine (Q), or glycine (G); $Z^5$ is a negatively charged amino acid, leucine (L), glutamine (Q), lysine (K), or alanine (A); $Z^6$ is asparagine (N), leucine (L), serine (S), glutamic acid (E), isoleucine (I), glutamine (Q), threonine (T), valine (V), lysine (K), or alanine (A); $Z^7$ is any amino acid; $Z^8$ is glutamine (Q) or lysine (K); $Z^9$ is leucine (L), valine (V), isoleucine (I), glycine (G), alanine (A), or is absent; and $Z^{10}$ is lysine (K), arginine (R), alanine (A), glutamic acid (E) or is absent. When the length of the peptide is 14 amino acids, $Z^1$ is lysine (K). When $Z^{10}$ is arginine (R), one of $Z^2$, $Z^3$, $Z^4$, $Z^5$, $Z^6$, $Z^7$, or $Z^9$ is alanine (A). The peptide optionally comprises an aspartic acid residue (D) inserted between $Z_4$ and $Z_5$, or a glutamine residue (Q) inserted between $Z_5$ and $Z_6$. The peptide does not comprise KLQEELNKV (SEQ ID NO: 53).

Where the peptide is a peptide comprising the sequence (III) or (IV), the peptide preferably consists of KLKDENSQLK (SEQ ID NO: 3), KLKDENSQL (SEQ ID NO: 119), KLKDENSQ (SEQ ID NO: 120), KLKDDNSQLK (SEQ ID NO: 16), KLKDENAQLK (SEQ ID NO: 18), KLKEENNQLK (SEQ ID NO: 20), KLKEENTQLK (SEQ ID NO: 21), KLKEENSQLR (SEQ ID NO: 22), KLKNENKQLK (SEQ ID NO: 27), KLKNENIQLK (SEQ ID NO: 28), KLKVENGQLK (SEQ ID NO: 32), KVKDENSQLK (SEQ ID NO: 36), KLKDEQEKLK (SEQ ID NO: 39), KLKDENEQLK (SEQ ID NO: 40), KLKNENRQLK (SEQ ID NO: 42), KLEDEQNSQIK (SEQ ID NO: 45), KLKDETSKLK (SEQ ID NO: 46), KLRDENSQLK (SEQ ID NO: 47), KLKQENTQLK (SEQ ID NO: 48), KLQEENHQL (SEQ ID NO: 49), KLKDDEVAQL (SEQ ID NO: 51), KLVEETKQL (SEQ ID NO: 52), LKDENSKL (SEQ ID NO: 54), LKNKNSQLK (SEQ ID NO: 55), LKEENSQ (SEQ ID NO: 56), LKGENEQLK (SEQ ID NO: 58), KLKEEITQL (SEQ ID NO: 59), LKDQNSKL (SEQ ID NO: 61), KLKDENTQLK (SEQ ID NO: 94), KLKTENSQLK (SEQ ID NO: 95), KIKDENSQLK (SEQ ID NO: 92), ALKDENSQLK (SEQ ID NO: 90), KLADENSQLK (SEQ ID NO: 91), KAKDENSQLR (SEQ ID NO: 98), KLADENSQLR (SEQ ID NO: 99), KLKAENSQLR (SEQ ID NO: 100), KLKDANSQLR (SEQ ID NO: 101), KLKDEASQLR (SEQ ID NO: 102), KLKDENAQLR (SEQ ID NO: 103), KLKDENSQAR (SEQ ID NO: 105), KLKDENSQLA (SEQ ID NO: 106), KLKDENSQLKS (SEQ ID NO: 121), KLKDENSQLKSE (SEQ ID NO: 122), KLKDENSQLKSEV (SEQ ID NO: 123), or KLKDENSQLKSEVS (SEQ ID NO: 124).

Pharmaceutical and cosmetic compositions comprising any of the above peptides and a pharmaceutically or cosmetically acceptable carrier are also provided.

Further pharmaceutical and cosmetic compositions are also provided. The compositions comprise a pharmaceutically or cosmetically acceptable carrier and a peptide. The peptide has a length of 7 to 14 amino acids and comprises the sequence (V): $Z^1$-$Z^2$-$Z^3$-$Z^4$-$Z^5$-$Z^6$-$Z^7$-$Z^8$-$Z^9$-$Z^{10}$, wherein $Z^1$ is lysine (K), alanine (A), or absent; $Z^2$ is leucine (L), isoleucine (I), alanine (A), or valine (V); $Z^3$ is lysine (K), glutamine (Q), arginine (R), glutamic acid (E), valine (V), or alanine (A); $Z^4$ is a negatively charged amino acid, threonine (T), asparagine (N), isoleucine (I), valine (V), alanine (A), tryptophan (Y), glutamine (Q), or glycine (G); $Z^5$ is a negatively charged amino acid, leucine (L), glutamine (Q), lysine (K), or alanine (A); $Z^6$ is asparagine (N), leucine (L), serine (S), glutamic acid (E), isoleucine (I), glutamine (Q), threonine (T), valine (V), lysine (K), or alanine (A); $Z^7$ is any amino acid; $Z^8$ is glutamine (Q) or lysine (K); $Z^9$ is leucine (L), valine (V), isoleucine (I), glycine (G), alanine (A), or is absent; and $Z^{10}$ is lysine (K), arginine (R), alanine (A), glutamic acid (E) or is absent. When the length of the peptide is 14 amino acids, $Z^1$ is lysine (K). When $Z^{10}$ is arginine (R), one of $Z^2$, $Z^3$, $Z^4$, $Z^5$, $Z^6$, $Z^7$, or $Z^9$ is alanine (A). The peptide optionally comprises an aspartic acid residue (D) inserted between $Z_4$ and $Z_5$, or a glutamine residue (Q) inserted between $Z_5$ and $Z_6$.

The peptide comprising the sequence (V) in the compositions described above preferably consists of KLKDENSQLK (SEQ ID NO: 3), KLKDENSQL (SEQ ID NO: 119), KLKDENSQ (SEQ ID NO: 120), KLKDDNSQLK (SEQ ID NO: 16), KLKDENAQLK (SEQ ID NO: 18), KLKEENNQLK (SEQ ID NO: 20), KLKEENTQLK (SEQ ID NO: 21), KLKEENSQLR (SEQ ID NO: 22), KLKNENKQLK (SEQ ID NO: 27), KLKNENIQLK (SEQ ID NO: 28), KLKVENGQLK (SEQ ID NO: 32), KVKDENSQLK (SEQ ID NO: 36), KLKDEQEKLK (SEQ ID NO: 39), KLKDENEQLK (SEQ ID NO: 40), KLKNENRQLK (SEQ ID NO: 42), KLEDEQNSQIK (SEQ ID NO: 45), KLKDETSKLK (SEQ ID NO: 46), KLRDENSQLK (SEQ ID NO: 47), KLKQENTQLK (SEQ ID NO: 48), KLQEENHQL (SEQ ID NO: 49), KLKDDEVAQL (SEQ ID NO: 51), KLVEETKQL (SEQ II) NO: 52), LKDENSKL (SEQ ID NO: 54), LKNKNSQLK (SEQ ID NO: 55), LKEENSQ (SEQ ID NO: 56), LKGENEQLK (SEQ ID NO: 58), KLKEEITQL (SEQ ID NO: 59), LKDQNSKL (SEQ ID NO: 61), KLKDENTQLK (SEQ ID NO: 94), KLKTENSQLK (SEQ ID NO: 95), KIKDENSQLK (SEQ ID NO: 92), ALKDENSQLK (SEQ ID NO: 90), KLADENSQLK (SEQ ID NO: 91), KAKDENSQLR (SEQ ID NO: 98), KLADENSQLR (SEQ ID NO: 99), KLKAENSQLR (SEQ ID NO: 100), KLKDANSQLR (SEQ ID NO: 101), KLKDEASQLR (SEQ ID NO: 102), KLKDENAQLR (SEQ ID NO: 103), KLKDENSQAR (SEQ ID NO: 105), KLKDENSQLA (SEQ ID NO: 106), KLKDENSQLKS (SEQ ID NO: 121), KLKDENSQLKSE (SEQ ID NO: 122), KLKDENSQLKSEV (SEQ ID NO: 123), or KLKDENSQLKSEVS (SEQ ID NO: 124).

Any of the above peptides are preferably capable of stimulating subcutaneous adipogenesis.

A method for reducing scarring or fibrosis is provided. The method comprises administering any one or more of the above peptides or compositions to a subject in an amount sufficient to reduce an area of scarring or fibrosis or improve the appearance of a scarred or fibrotic area.

A method of improving the appearance of skin is also provided. The method comprises administering any one or more of the above peptides or compositions to a subject in an amount sufficient to improve the appearance of skin in an area of a subject.

A method of improving tissue volume in an area of a subject is provided. The method comprises administering any one or more of the above peptides or compositions to the subject in an amount sufficient to increase the tissue volume in the area.

A method of smoothing skin in an area of a subject is also provided. The method comprises administering any one or more of the above peptides or compositions to the subject in an amount sufficient to smooth skin in the area.

A method of recruiting stem cells to formation of subcutaneous fat in a subject is provided. The method comprises administering any one or more of the above peptides or compositions to the subject in an amount sufficient to recruit stem cells to the formation of subcutaneous fat in the subject.

A method of reconstructing tissue of a subject is also provided. The method comprises administering any one or more of the above peptides or compositions to the tissue of the subject in an amount sufficient to increase the volume of the tissue during or after a tissue reconstruction procedure.

A method of reducing heel pain in a subject is also provided. The method comprises administering any one or more of the above peptides or compositions to the subject in an amount sufficient to reduce heel pain in the subject during walking.

Other objects and features will be in part apparent and in part pointed out hereinafter.

Definitions

The term "peptide" as used herein refers to a polymer of amino acid residues typically ranging in length from about 7 to about 14 amino acids. The amino acid residues of the peptide can be "L-form" amino acid residues, "D" amino acid residues, or a combination thereof. L-, D-, or β-amino acid versions of the peptide sequence as well as retro, inverso, and retro-inverso isoforms are included. "β-peptides" are comprised of "β amino acids", which have their amino group bonded to the β carbon rather than the α-carbon as in the 20 standard biological amino acids.

The terms "standard" and "natural" as applied to peptides herein refer to peptides constructed only from the standard naturally-occurring amino acids: alanine (Ala, A), cysteine (Cys, C), aspartate (Asp, D), glutamate (Glu, E), phenylalanine (Phe, F), glycine (Gly, G), histidine (His, H), isoleucine (Ile, I), lysine (Lys, K), leucine (Leu, L), methionine (Met, M), asparagine (Asn, N), proline (Pro, P), glutamine (Gln, Q), arginine (Arg, R), serine (Ser, S), threonine (Thr, T), valine (Val, V), tryptophan (Trp, W), and tyrosine (Tyr, Y). A peptide of the invention "corresponds" to a natural peptide if it elicits a biological activity (e.g., adipogenic activity) related to the biological activity and/or specificity of the naturally occurring peptide. The elicited activity may be the same as, greater than or less than that of the natural peptide.

The terms "non-standard," and "non-natural," and "analogue" as applied to peptides herein refer to peptides which contain one or more amino acids which are not standard amino acids and/or which are not naturally-occurring amino acids. A skilled artisan would be familiar such non-standard and non-naturally occurring amino acids and would be able to select suitable non-standard and non-naturally occurring amino acids for use in the peptides of the present invention. Amino acid analogues include amino acids that occur in nature but which are non-standard (e.g., norvaline, norleucine), as well as synthetic amino acids that do not occur in nature. For example, various amino acid analogues include, but are not limited to 2-aminoadipic acid, 3-aminoadipic acid, beta-alanine (beta-aminopropionic acid), 2-aminobutyric acid, 4-aminobutyric acid, piperidinic acid, 6-aminocaproic acid, 2-aminoheptanoic acid, 2-aminoisobutyric acid, 3-aminoisobutyric acid, 2-aminopimelic acid, 2,4 diaminobutyric acid, desmosine, 2,2'-diaminopimelic acid, 2,3-diaminopropionic acid, n-ethylglycine, n-ethylasparagine, hydroxylysine, allo-hydroxylysine, 3-hydroxyproline, 4-hydroxyproline, isodesmosine, allo-isoleucine, n-methylglycine, sarcosine, n-methylisoleucine, 6-n-methyllysine, n-methylvaline, norvaline, norleucine, ornithine, and the like. These modified amino acids are illustrative and not intended to be limiting.

The term "conservative substitution" is used to refer to an amino acid substitution that does not substantially alter the activity (e.g., adipogenic activity and/or specificity) of the peptide. Conventional conservative amino acid substitutions involve substituting one amino acid for another amino acid with similar structure and chemical properties (e.g., charge or hydrophobicity). Such conventional substitutions include, but are not limited to, the following: 1) glycine (G)/alanine (A), 2) arginine (R)/lysine (K), 3) serine (S)/threonine (T)/tyrosine (Y), 4) leucine (L)/isoleucine (I)/valine (V), 5) aspartic acid (D)/glutamic acid (E), 6) glutamine (Q)/asparagine (N), and 7) phenylalanine (F)/tyrosine (Y)/tryptophan (W). Other functional conservative substitutions include, but are not limited to 8) glycine (G)/alanine (A)/proline (P), 9) tyrosine (Y)/histidine (H), 10) arginine (R)/lysine (K)/histidine (H), 11) serine (S)/threonine (T)/cysteine (C), 12) leucine (L)/isoleucine (I)/valine (V)/methionine (M), 13) alanine (A)/serine (S)/threonine (T)/methionine (M)/glycine (G), and 14) methionine (M)/lysine (K) (under hydrophobic conditions). Conservative substitutions also include "analog substitutions" where a standard amino acid is replaced by a non-standard (e.g., rare, synthetic, etc.) amino acid differing minimally from the standard amino acid. Such analog substitutions can be derived synthetically from the standard amino acids, are isomers, or are metabolite precursors. Examples of such "analog substitutions" include, but are not limited to, 1) Lys→ornithine (Orn), 2) Leu→Norleucine, 3) Lys→Lys[TFA], 4) Phe→phenylglycine, and 5) δ-amino butylglycine ξ-amino hexylglycine, where [TFA] refers to trifluoroacetyl. Conservative substitutions also include a replacement of an amino acid with another amino acid having shared properties as shown in FIG. 1. Such substitutions include substitutions of one amino acid in one of the following groups with another amino acid in the same group: 1) aromatic amino acids: phenylalanine (F)/tyrosine (Y)/histidine (H)/tryptophan (W); 2) aliphatic amino acids: isoleucine (I)/valine (V)/leucine(L)/alanine (A)/glycine (G); 3) positively charged amino acids: histidine (H)/lysine (K)/arginine (R); 4) negatively charged amino acids: aspartate (D)/glutamate (E); and 5) tiny amino acids: cysteine (C)/alanine (A)/glycine (G)/serine (S). Conservative substitutions also include substitutions of amino acids having uncharged polar side chains, i.e., serine (S)/threonine (T)/asparagine (N)/glutamine (Q)/tyrosine (Y)/cysteine (C). Where amino acid sequences are disclosed herein, amino acid sequences comprising one or more of the above-identified conservative substitutions are also contemplated.

The term "variant" refers to a peptide differing from a peptide of the invention, but retaining essential properties thereof (e.g., the ability to inhibit RHAMM activity and/or the ability to induce subcutaneous adipogenesis). Generally, variants are overall closely similar, and may be identical, in many regions, to a peptide sequence of the invention. Besides conservative amino acid substitution, a variant peptide can include (i) substitutions with one or more of non-conserved amino acid residues, where the substituted amino acid residues may or may not be a standard amino acid and may or may not be a naturally occurring amino acid, and/or (ii) conservative substitutions with one or more non-standard or non-naturally occurring amino acid residues, and/or (iii) fusion of the peptide with another compound, such as a compound to increase the stability and/or solubility of the peptide (for example, polyethylene glycol), and/or (iv) fusion of the peptide with additional amino acids, such as, for example, an IgG Fc fusion region peptide, or leader or secretory sequence, or a sequence facilitating purification. Methods of making such variant peptides are within the skill of one of ordinary skill in the art. For example, peptide variants containing amino acid substitutions of charged amino acids with other charged or neutral amino acids may produce peptides with improved characteristics, such as less aggregation. Aggregation of pharmaceutical formulations both reduces activity and increases clearance due to the aggregate's immunogenic activity (see, e.g., Pinckard et al. (1967) *Clin. Exp. Immunol.* 2: 331340; Robbins et al. (1987) *Diabetes* 36: 838-845; Cleland et al. (1993) *Crit. Rev. Therapeutic Drug Carrier Systems,* 10: 307-377).

The terms "subject," "individual," and "patient" may be used interchangeably and refer to a mammal, preferably a human or a non-human primate, but also domesticated mammals (e.g., canine or feline), laboratory mammals (e.g., mouse, rat, rabbit, hamster, guinea pig), and agricultural mammals (e.g., equine, bovine, porcine, ovine, capra, and the like). The subject can be a human (e.g., adult male, adult female, adolescent male, adolescent female, male child, female child) under the care of a physician, nurse practitioner, or other health worker in a hospital, as an outpatient, or in other clinical contexts. Alternatively, the subject may not be under the care or prescription of a physician, nurse practitioner, or other health worker.

BRIEF DESCRIPTION OF THE DRAWINGS

FIGS. 3A and 3B show illustrative data regarding the adipogenic effects of KLKDENSQLK (SEQ ID NO: 3) and several related sequences in Assay 1 (FIG. 3A) and Assay 2 (FIG. 3B).

FIG. 4 depicts a functional region of RHAMM (SEQ ID NO: 4).

FIGS. 7, 8, and 9 show illustrative data from adiponectin ELISA assays performed on supernatant medium from 3T3L cells treated with the peptides indicated in FIGS. 7, 8, and 9.

DESCRIPTION OF THE PREFERRED EMBODIMENTS

Figure 1:
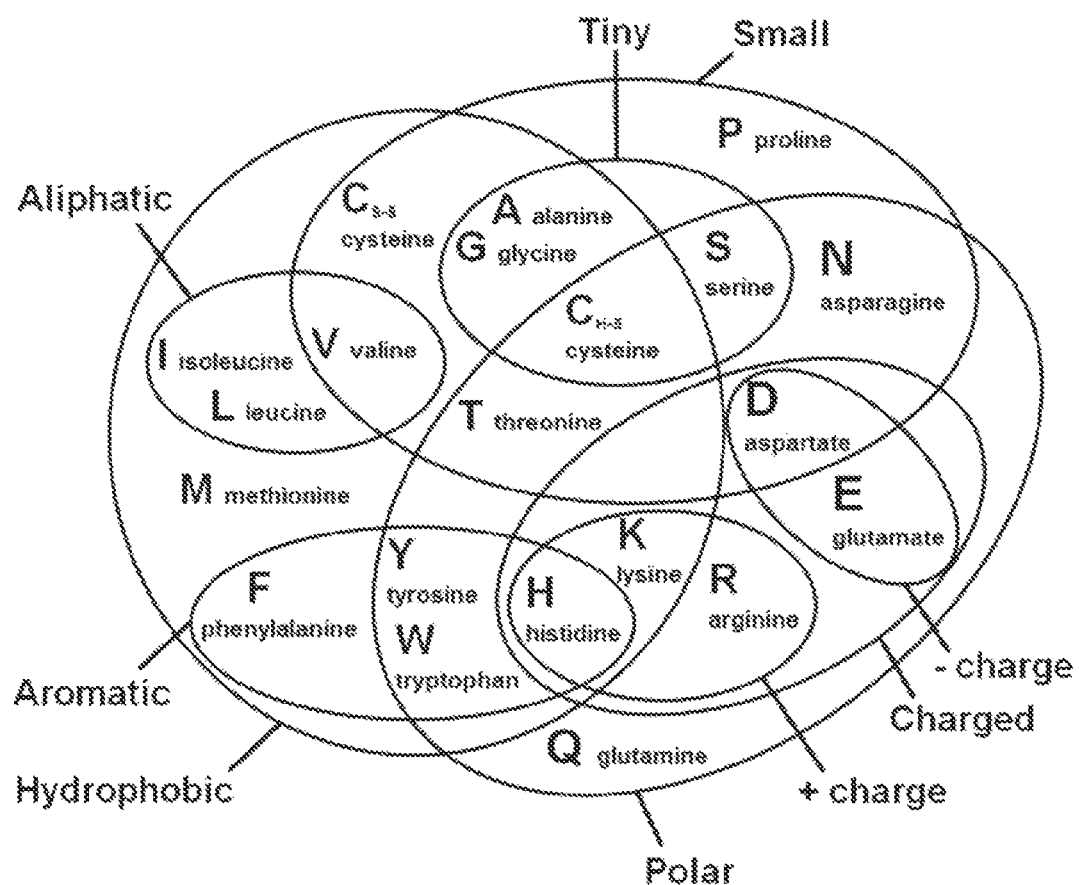
FIG. 1 illustrates the classification used herein for various naturally occurring standard amino acids. It will be recognized that non-standard and/or non-naturally occurring amino acids can also fall into this classification.

The present invention provides peptides that stimulate subcutaneous adipogenesis. These peptides are useful in a variety of cosmetic and therapeutic applications. Without being bound to a particular theory, it is believed that the peptides described herein achieve their adipogenic activity by inhibiting (fully or partially) the RHAMM functions related to adipogenesis, e.g. affecting hyaluronan and/or adipogenic protein interactions.

The peptides of the invention are relatively short in length, having a length of 7 to 13 or 7 to 14 amino acids. The "short" peptides offer certain advantages such as reduced cost of production, reduced immunogenicity, increased activity, and increased penetration into skin when applied topically.

Peptide B is 15-mer peptide having the sequence KLKDENSQLKSEVSK (SEQ ID NO: 2). Peptide B was derived from the binding region of RHAMM. PCT Publication No. WO 2014/082042 provides data showing that peptide B and a 6-mer fragment derived from the carboxy terminus of peptide B (KSEVSK, SEQ ID NO: 7) are strongly adipogenic. A peptide derived from the amino terminus of peptide B, KLKDENS (SEQ ID NO: 8), was previously found to lack adipogenic activity. However, as is described in more detail below in the Examples, it has now been discovered that several other peptides derived from the amino terminus of peptide B, KLKDENSQLK (SEQ ID NO: 3) and KLKDENSQ (SEQ ID NO: 9), are adipogenic.

Peptide P15-1, having the sequence STMMSRSHK-TRSHHV (SEQ ID NO: 1), was isolated by screening a random phage library for peptides having the ability to bind to hyaluronan (HA). Alignments were performed to assess the similarity of the P15-1 peptide to peptide B, a peptide derived from the HA-binding region of RHAMM. As described in PCT Publication No. WO 2014/082042, these alignments indicated that the adipogenic region of peptide P15-1 was localized to its amino-terminal region, and in particular to the 6-mer fragment STMMSR (SEQ ID NO: 10). However, it has now been discovered that a peptide derived from the carboxy terminus of peptide P15-1, KTRSHHV (SEQ ID NO: 6), is adipogenic.

In addition, as described in detail below in the Examples, it was possible to identify conserved motifs that are believed to be responsible for the adipogenic properties of the peptides.

It is also believed that the use of RHAMM-inhibiting peptides described herein provides signals that force differentiation into adipocytes. In addition, RHAMM −/− dermal fibroblasts express very low levels of smooth muscle actin indicating that RHAMM also regulates development of this mesenchymal stem cell lineage.

With respect to mesenchymal and other skin stem cells, a unique advantage of using the RHAMM-inhibiting peptides described herein for increasing subcutaneous fat is that its effects are selective. Thus, visceral fat, whose increased accumulation on body organs is associated with disease is decreased while subcutaneous fat is increased. This is an unusual effect and differentiates RHAMM's effects from other adipocyte promoting factors such as leptin that affect accumulation of both types of adipocytes. Accordingly, it is believed the peptides described herein will not increase visceral fat.

Another property of RHAMM is related to its very restricted expression in the adult human tissues. RHAMM is poorly expressed or not expressed physiologically but is increased following tissue injury or transformation to the neoplastic state. Therefore, the RHAMM-inhibitory peptides described herein should not induce any pathology or defect due to RHAMM inhibition. In fact, it is believed that blocking RHAMM function can be beneficial to those with a tumor load or with inflammation-based diseases such as arthritis since RHAMM has pro-oncogenic, pro-inflammatory functions.

RHAMM Inhibiting Peptides.

Peptides are provided that inhibit RHAMM biological activity and thereby induce or stimulate subcutaneous adipogenesis. As described above, such peptides comprise peptides derived from the carboxy terminus of peptide P15-1 and related sequences, or peptides derived from the amino terminus of peptide B and related sequences.

Peptides Derived from the Carboxy Terminus of Peptide P15-1 and Related Sequences A peptide that stimulates subcutaneous adipogenesis is provided that has a length of 7 to 13 amino acids and comprises the sequence (I):

$$X^1\text{-}X^2\text{-}X^3\text{-}X^4\text{-}X^5\text{-}X^6\text{-}X^7 \tag{I}$$

wherein $X^1$ is lysine (K) or arginine (R); $X^2$ is any amino acid; $X^3$ is arginine (R); $X^4$ is serine (S) or alanine (A); $X^5$ is histidine (H); $X^6$ is histidine (H); and $X^7$ is valine (V). The peptide optionally comprises a cysteine (C) residue inserted between $X^4$ and $X^5$, or a threonine (T) followed by an alanine (A) inserted between $X^5$ and $X^6$.

Another peptide that stimulates subcutaneous adipogenesis is also provided. The peptide has a length of 7 to 14 amino acids and comprises the sequence (II):

$$X^1\text{-}X^2\text{-}X^3\text{-}X^4\text{-}X^5\text{-}X^6\text{-}X^7 \tag{II}$$

$X^1$ is lysine (K) or arginine (R); $X^2$ is any amino acid; $X^3$ is arginine (R); $X^4$ is serine (S) or alanine (A); $X^5$ is histidine (H); $X^6$ is histidine (H); and $X^7$ is valine (V). The peptide optionally comprises a cysteine (C) residue inserted between $X^4$ and $X^5$, or a threonine (T) followed by an alanine (A) inserted between $X^5$ and $X^6$. When the length of the peptide is 14 amino acids, the peptide does not comprise a serine (S) residue at its amino terminus.

In the peptides comprising the sequence (I) or (II), the peptide preferably does not comprise a cysteine (C) residue inserted between $X^4$ and $X^5$, or a threonine (T) followed by an alanine (A) inserted between $X^5$ and $X^6$.

In the peptides comprising the sequence (I) or (II), $X^1$ is preferably lysine (K).

In the peptides comprising the sequence (I) or (II), $X^2$ can be threonine (T), alanine (A), serine (S), isoleucine (I), asparagine (N), proline (P), aspartic acid (D), lysine (K), glutamine (Q), glutamic acid (E), leucine (L), valine (V), or arginine (R). For example, $X^2$ can be threonine (T), serine (S), isoleucine (I), asparagine (N), proline (P), aspartic acid (D), glutamic acid (E), or leucine (L). $X^2$ is suitably threonine (T), serine (S), asparagine (N), proline (P), aspartic acid (D), or leucine (L). $X^2$ can be threonine (T), isoleucine (I), or glutamic acid (E). $X^2$ is preferably threonine (T), serine (S), or asparagine (N). For example $X^2$ can be threonine (T) or serine (S). $X^2$ can be serine (S) or asparagine (N). $X^2$ can be threonine (T).

The amino acid sequence (I) or (II) of the peptide can comprise KTRSHHV (SEQ ID NO: 6), KTRSHTAHV (SEQ ID NO: 63), RTRSHHV (SEQ ID NO: 64), KARSHHV (SEQ ID NO: 66), KSRSHHV (SEQ ID NO: 67), KIRSHHV (SEQ ID NO: 68), KNRSHHV (SEQ ID NO: 69), KPRSHHV (SEQ ID NO: 70), KDRSHHV (SEQ ID NO: 72), KKRSHHV (SEQ ID NO: 73), KQRSHHV (SEQ ID NO: 74), KERSHHV (SEQ ID NO: 75), KLRSHHV (SEQ ID NO: 76), KVRSHHV (SEQ ID NO: 77), KRRSHHV (SEQ ID NO: 83), KTRAHHV (SEQ ID NO: 87), KTRSCHHV (SEQ ID NO: 111), or a combination thereof. Preferably, the amino acid sequence (I) or (II) of the peptide comprises KTRSHHV (SEQ ID NO: 6), KTRAHHV (SEQ ID NO: 87), KSRSHHV (SEQ ID NO: 67), or KNRSHHV (SEQ ID NO: 69). For example, the amino acid sequence (I) or (II) of the peptide can comprise KTRSHHV (SEQ ID NO: 6). The amino acid sequence (I) or (II) of the peptide can comprise KTRAHHV (SEQ ID NO: 87). The amino acid sequence (I) or (II) of the peptide can comprise KSRSHHV (SEQ ID NO: 67) or KNRSHHV (SEQ ID NO: 69).

The amino acid sequence (I) or (II) of the peptide can consist of KTRSHHV (SEQ ID NO: 6), KTRSHTAHV (SEQ ID NO: 63), RTRSHHV (SEQ ID NO: 64), KARSHHV (SEQ ID NO: 66), KSRSHHV (SEQ ID NO: 67), KIRSHHV (SEQ ID NO: 68), KNRSHHV (SEQ ID NO: 69), KPRSHHV (SEQ ID NO: 70), KDRSHHV (SEQ ID NO: 72), KKRSHHV (SEQ ID NO: 73), KQRSHHV (SEQ ID NO: 74), KERSHHV (SEQ ID NO: 75), KLRSHHV (SEQ ID NO: 76), KVRSHHV (SEQ ID NO: 77), KRRSHHV (SEQ ID NO: 83), KTRAHHV (SEQ ID NO: 87), KTRSCHHV (SEQ ID NO: 111), HKTRSHHV (SEQ ID NO: 112), SHKTRSHHV (SEQ ID NO: 113), RSHKTRSHHV (SEQ ID NO: 114), SRSHKTRSHHV (SEQ ID NO: 115), MSRSHKTRSHHV (SEQ ID NO: 116), MMSRSHKTRSHHV (SEQ ID NO: 117), or TMMSRSHKTRSHHV (SEQ ID NO: 118). Preferably, the amino acid sequence (I) or (II) of the peptide consists of KTRSHHV (SEQ ID NO: 6), KTRAHHV (SEQ ID NO: 87), KSRSHHV (SEQ ID NO: 67), or KNRSHHV (SEQ ID NO: 69). For example, the amino acid sequence (I) or (II) of the peptide can consist of KTRSHHV (SEQ ID NO: 6). The amino acid sequence (I) or (II) of the peptide can consist of KTRAHHV (SEQ ID NO: 87). The amino acid sequence (I) or (II) of the peptide can consist of KSRSHHV (SEQ ID NO: 67) or KNRSHHV (SEQ ID NO: 69).

The peptides comprising the sequence (I) or (II) can have a length of 13 amino acids, 12, amino acids, 11 amino acids, 10 amino acids, 9 amino acids, 8 amino acids, or 7 amino acids. The peptides comprising the sequence (II) can also have a length of 14 amino acids.

Peptides Derived from the Carboxy Terminus of Peptide B and Related Sequences

A peptide is provided that has a length of 7 to 14 amino acids and comprises the sequence (III):

$$Z^1\text{-}Z^2\text{-}Z^3\text{-}Z^4\text{-}Z^5\text{-}Z^6\text{-}Z^7\text{-}Z^8\text{-}Z^9\text{-}Z^{10} \tag{III}$$

wherein $Z^1$ is lysine (K), alanine (A), or absent; $Z^2$ is leucine (L), isoleucine (I), alanine (A), or valine (V); $Z^3$ is lysine (K), glutamine (Q), arginine (R), glutamic acid (E), valine (V), or alanine (A); $Z^4$ is a negatively charged amino acid, threonine (T), asparagine (N), isoleucine (I), valine (V), alanine (A), tryptophan (Y), glutamine (Q), or glycine (G); $Z^5$ is a negatively charged amino acid, leucine (L), glutamine (Q), lysine (K), or alanine (A); $Z^6$ is asparagine (N), leucine (L), serine (S), glutamic acid (E), isoleucine (I), glutamine (Q), threonine (T), valine (V), lysine (K), or alanine (A); $Z^7$ is any amino acid; $Z^8$ is glutamine (Q) or lysine (K); $Z^9$ is leucine (L), valine (V), isoleucine (I), glycine (G), alanine (A), or is absent; and $Z^{10}$ is lysine (K), arginine (R), alanine (A), glutamic acid (E) or is absent. When $Z^6$ is leucine (L), $Z^9$ is not valine (V). When $Z^9$ is valine (V), $Z^6$ is not leucine (L). When the length of the peptide is 14 amino acids, $Z^1$ is lysine (K). When $Z^{10}$ is arginine (R), one of $Z^2$, $Z^3$, $Z^4$, $Z^5$, $Z^6$, $Z^7$, or $Z^9$ is alanine (A). The peptide optionally comprises an aspartic acid residue (D) inserted between $Z_4$ and $Z_5$, or a glutamine residue (Q) inserted between $Z_5$ and $Z_6$.

Another peptide is also provided. The peptide has a length of 7 to 14 amino acids and comprises the sequence (IV):

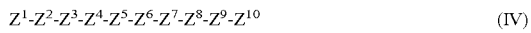

$$Z^1\text{-}Z^2\text{-}Z^3\text{-}Z^4\text{-}Z^5\text{-}Z^6\text{-}Z^7\text{-}Z^8\text{-}Z^9\text{-}Z^{10} \qquad (IV)$$

wherein $Z^1$ is lysine (K), alanine (A), or absent; $Z^2$ is leucine (L), isoleucine (I), alanine (A), or valine (V); $Z^3$ is lysine (K), glutamine (Q), arginine (R), glutamic acid (E), or valine (V), or alanine (A); $Z^4$ is a negatively charged amino acid, threonine (T), asparagine (N), isoleucine (I), valine (V), alanine (A), tryptophan (Y), glutamine (Q), or glycine (G); $Z^5$ is a negatively charged amino acid, leucine (L), glutamine (Q), lysine (K), or alanine (A); $Z^6$ is asparagine (N), leucine (L), serine (S), glutamic acid (E), isoleucine (I), glutamine (Q), threonine (T), valine (V), lysine (K), or alanine (A); $Z^7$ is any amino acid; $Z^8$ is glutamine (Q) or lysine (K); $Z^9$ is leucine (L), valine (V), isoleucine (I), glycine (G), alanine (A), or is absent; and $Z^{10}$ is lysine (K), arginine (R), alanine (A), glutamic acid (E) or is absent. When $Z^{10}$ is arginine (R), one of $Z^2$, $Z^3$, $Z^4$, $Z^5$, $Z^6$, $Z^7$, or $Z^9$ is alanine (A). When the length of the peptide is 14 amino acids, $Z^1$ is lysine (K). The peptide optionally comprises an aspartic acid residue (D) inserted between $Z_4$ and $Z_5$, or a glutamine residue (Q) inserted between $Z_5$ and $Z_6$. The peptide does not comprise KLQEELNKV (SEQ ID NO: 53).

In the peptides comprising the sequence (III) or (IV), the peptide preferably does not comprise an aspartic acid residue (D) inserted between $Z_4$ and $Z_5$, or a glutamine residue (Q) inserted between $Z_5$ and $Z_6$.

In the peptides comprising the sequence (III) or (IV), $Z^1$ is lysine (K) or alanine (A). $Z^1$ is more preferably lysine (K).

In the peptides comprising the sequence (III) or (IV), $Z^2$ can be leucine (L), isoleucine (I), or alanine (A). $Z^2$ is preferably leucine (L) or isoleucine (I). For example, $Z^2$ can be leucine (L).

In the peptides comprising the sequence (III) or (IV), $Z^3$ can be lysine (K), glutamine (Q), or alanine (A). $Z^3$ is preferably lysine (K) or alanine (A). For example, $Z^3$ can be lysine (K).

In the peptides comprising the sequence (III) or (IV), $Z^4$ can be a negatively charged amino acid, threonine (T), or alanine (A). For example, $Z^4$ can be aspartic acid (D), glutamic acid (E), threonine (T), or alanine (A). $Z^4$ is preferably aspartic acid (D), threonine (T), or alanine (A). For example, $Z^4$ can be aspartic acid (D) or threonine (T). $Z^4$ can be aspartic acid (D) or alanine (A). $Z^4$ can be aspartic acid (D) or glutamic acid (E). For example, $Z^4$ can be aspartic acid (D).

In the peptides comprising the sequence (III) or (IV), $Z^5$ can be a negatively charged amino acid or alanine (A). $Z^5$ is preferably a negatively charged amino acid. The negatively charged amino acid is aspartic acid (D) or glutamic acid (E). For example, the negatively charged amino acid can be glutamic acid (E).

In the peptides comprising the sequence (III) or (IV), $Z^6$ can asparagine (N), leucine (L), or alanine (A). For example, $Z^6$ can be asparagine (N) or leucine (L). As another example, $Z^6$ can be asparagine (N) or alanine (A). $Z^6$ is preferably asparagine (N).

In the peptides comprising the sequence (III) or (IV), $Z^7$ can be serine (5), asparagine (N), alanine (A), or threonine (T). For example, $Z^7$ can be serine (S), asparagine (N), or alanine (A). As another example, $Z^7$ can be serine (S), alanine (A), or threonine (T). $Z^7$ can be serine (S) or alanine (A). $Z^7$ can be serine (S).

In the peptides comprising the sequence (III) or (IV), $Z^8$ is preferably glutamine (Q).

In the peptides comprising the sequence (III) or (IV), $Z^9$ can be leucine (L), valine (V), alanine (A), or can be absent. For example, $Z^9$ can be leucine (L), valine (V), or alanine (A). As another example, $Z^9$ can be leucine (L), valine (V), or is absent. $Z^9$ can be leucine (L) or alanine (A). $Z^9$ is preferably leucine (L).

In the peptides comprising the sequence (III) or (IV), $Z^{10}$ can be lysine (K), arginine (R), alanine (A), or can be absent. For example, $Z^{10}$ can be lysine (K) or arginine (R), or alanine (A). $Z^{10}$ is preferably lysine (K).

In the peptides comprising the sequence (III) or (IV), when $Z^{10}$ is arginine (R), one of $Z^2$, $Z^4$, or $Z^7$ is preferably alanine (A).

In the peptides comprising the sequence (III) or (IV), preferably no more than one of $Z^1$, $Z^2$, $Z^3$, $Z^5$, $Z^6$, $Z^7$, $Z^9$, and $Z^{10}$ is alanine (A).

In preferred peptides comprising sequence (III) or (IV), $Z^1$ is lysine (K) or alanine (A); $Z^2$ is leucine (L), isoleucine (I), or alanine (A); $Z^3$ is lysine (K), glutamine (Q), or alanine (A); $Z^4$ is aspartic acid (D), glutamic acid (E), threonine (T), or alanine (A); $Z^5$ is aspartic acid (D), glutamic acid (E), or alanine (A); $Z^6$ is asparagine (N), leucine (L), or alanine (A); $Z^7$ is serine (S), asparagine (N), threonine (T), or alanine (A); $Z^9$ is leucine (L), valine (V), alanine (A), or absent; and $Z^{10}$ is lysine (K), arginine (R), alanine (A), or absent.

For example, in the peptides comprising the sequence (III) or (IV), $Z^5$ can be aspartic acid (D) or glutamic acid (E); $Z^6$ can be asparagine (N) or leucine (L); $Z^7$ can be serine (S), asparagine (N), or alanine (A); and $Z^9$ can be leucine (L), valine (V), or absent.

As another example, in the peptides comprising the sequence (III) or (IV), $Z^3$ can be lysine (K) or alanine (A); $Z^4$ can be aspartic acid (D), threonine (T), or alanine (A); $Z^6$ can be asparagine (N) or alanine (A); $Z^7$ can be serine (S), threonine (T), or alanine (A); $Z^8$ can be glutamine (Q); $Z^9$ can be leucine (L) or alanine (A); and $Z^{10}$ can be lysine (K), arginine (R), or alanine (A).

As yet another example, in the peptides comprising the sequence (III) or (IV), $Z^3$ can be lysine (K) or alanine (A); $Z^4$ can be aspartic acid (D), threonine (T), or alanine (A); $Z^5$ can be aspartic acid (D) or glutamic acid (E); $Z^6$ can be asparagine (N); $Z^7$ can be serine (S) or alanine (A); $Z^8$ can be glutamine (Q); $Z^9$ can be leucine (L); and $Z^{10}$ can be lysine (K), arginine (R), or alanine (A).

As a further example, in the peptides comprising the sequence (III) or (IV), $Z^1$ can be lysine (K); $Z^2$ can be leucine (L) or isoleucine (I); $Z^3$ can be lysine (K) or alanine (A); $Z^4$ can be aspartic acid (D) or threonine (T); $Z^5$ can be aspartic acid (D) or glutamic acid (E); $Z^6$ can be asparagine (N); $Z^7$ can be serine (S); $Z^8$ can be glutamine (Q); $Z^9$ can be leucine (L); and $Z^{10}$ can be lysine (K).

As another example, in the peptides comprising the sequence (III) or (IV), $Z^1$ can be lysine (K) or alanine (A); $Z^2$ can be leucine (L), isoleucine (I), or alanine (A); $Z^3$ can be lysine (K) or alanine (A); $Z^4$ can be aspartic acid (D) or alanine (A); $Z^5$ can be aspartic acid (D), glutamic acid (E), or alanine (A); $Z^6$ can be asparagine (N) or alanine (A); $Z^7$ can be serine (S), threonine (T), or alanine (A); $Z^8$ can be glutamine (Q); $Z^9$ can be leucine (L) or alanine (A); and $Z^{10}$ can be lysine (K), arginine (R), or alanine (A).

As yet another example, in the peptides comprising the sequence (III) or (IV), $Z^5$ can be aspartic acid (D) or glutamic acid (E); $Z^6$ can be asparagine (N); $Z^7$ can be serine (S) or alanine (A); and $Z^9$ can be leucine (L).

In other preferred peptides comprising sequence (III) or (IV), $Z^1$ is lysine (K); $Z^2$ is leucine (L); $Z^3$ is lysine (K), glutamine (Q), or arginine (R); $Z^4$ is a negatively charged amino acid, threonine (T), asparagine (N), isoleucine (I), valine (V), or alanine (A); $Z^5$ is a negatively charged amino acid; $Z^6$ is asparagine (N) or leucine (L); $Z^9$ is leucine (L), valine (V), isoleucine (I), or is absent; and $Z^{10}$ is lysine (K), arginine (R), or is absent. For example, $Z^4$ can be a negatively charged amino acid, threonine (T), or asparagine (N); $Z^8$ can be glutamine (Q); and $Z^9$ can be leucine (L), valine (V), or is absent.

In further preferred peptides comprising sequence (III) or (IV), $Z^2$ is leucine (L) or isoleucine (I); $Z^3$ is lysine (K), glutamine (Q), arginine (R), or valine (V); $Z^4$ is aspartic acid (D), glutamic acid (E), threonine (T), asparagine (N), isoleucine (I), valine (V), alanine (A), tryptophan (Y), glutamine (Q), or glycine (G); $Z^5$ is aspartic acid (D), glutamic acid (E), leucine (L), or glutamine (Q); $Z^6$ is asparagine (N), serine (S), glutamic acid (E), glutamine (Q), or threonine (T); $Z^7$ is serine (S), asparagine (N), alanine (A), threonine (T), isoleucine (I), lysine (K), leucine (L), phenylalanine (F), glycine (G), valine (V), glutamic acid (E), or histidine (H); $Z^9$ is leucine (L), valine (V), or is absent; and $Z^{10}$ is lysine (K), arginine (R), or is absent. For example, $Z^1$ can be lysine (K); $Z^3$ can be lysine (K); $Z^4$ can be aspartic acid (D), glutamic acid (E), threonine (T), asparagine (N), isoleucine (I), valine (V), or tryptophan (Y); $Z^5$ can be aspartic acid (D), glutamic acid (E), or leucine (L); $Z^6$ can be asparagine (N), serine (S), glutamic acid (E), or glutamine (Q); $Z^7$ can be serine (S), asparagine (N), alanine (A), threonine (T), isoleucine (I), lysine (K), leucine (L), phenylalanine (F), glycine (G), valine (V), or glutamic acid (E); $Z^8$ can be glutamine (Q); $Z^9$ can be leucine (L); and $Z^{10}$ can be lysine (K) or arginine (R).

The amino acid sequence (III) or (IV) of the peptide can comprise KLKDENSQLK (SEQ ID NO: 3), KLKDENSQL (SEQ ID NO: 119), KLKDENSQ (SEQ ID NO: 120), KLKDDNSQLK (SEQ ID NO: 16), KLKDENAQLK (SEQ ID NO: 18), KLKEENNQLK (SEQ ID NO: 20), KLKEENTQLK (SEQ ID NO: 21), KLKEENSQLR (SEQ ID NO: 22), KLKNENKQLK (SEQ ID NO: 27), KLKNENIQLK (SEQ ID NO: 28), KLKVENGQLK (SEQ ID NO: 32), KVKDENSQLK (SEQ ID NO: 36), KLKDEQEKLK (SEQ ID NO: 39), KLKDENEQLK (SEQ ID NO: 40), KLKNENRQLK (SEQ ID NO: 42), KLEDEQNSQIK (SEQ ID NO: 45), KLKDETSKLK (SEQ ID NO: 46), KLRDENSQLK (SEQ ID NO: 47), KLKQENTQLK (SEQ ID NO: 48), KLQEENHQL (SEQ ID NO: 49), KLKDDEVAQL (SEQ ID NO: 51), KLVEETKQL (SEQ ID NO: 52), LKDENSKL (SEQ ID NO: 54), LKNKNSQLK (SEQ ID NO: 55), LKEENSQ (SEQ ID NO: 56), LKGENEQLK (SEQ ID NO: 58), KLKEETKQL (SEQ ID NO: 59), LKDQNSKL (SEQ ID NO: 61), KLKDENTQLK (SEQ ID NO: 94), KLKTENSQLK (SEQ ID NO: 95), KIKDENSQLK (SEQ ID NO: 92), ALKDENSQLK (SEQ ID NO: 90), KLADENSQLK (SEQ ID NO: 91), KAKDENSQLR (SEQ ID NO: 98), KLADENSQLR (SEQ ID NO: 99), KLKAENSQLR (SEQ ID NO: 100), KLKDANSQLR (SEQ ID NO: 101), KLKDEASQLR (SEQ ID NO: 102), KLKDENAQLR (SEQ ID NO: 103), KLKDENSQAR (SEQ ID NO: 105), KLKDENSQLA (SEQ ID NO: 106), or a combination thereof.

The amino acid sequence (III) or (IV) of the peptide preferably comprises KLKDENSQLK (SEQ ID NO: 3), KLKDENSQL (SEQ ID NO: 119), KLKDENSQ (SEQ ID NO: 120), KLQEELNKV (SEQ ID NO: 53), KLKDDNSQLK (SEQ ID NO: 16), KLKTENSQLK, KIKDENSQLK (SEQ ID NO: 92), KLADENSQLK (SEQ ID NO: 91), KLKDENTQLK (SEQ ID NO: 94), ALKDENSQLK (SEQ ID NO: 90), KAKDENSQLR (SEQ ID NO: 98), KLADENSQLR (SEQ ID NO: 99), KLKAENSQLR (SEQ ID NO: 100), KLKDANSQLR (SEQ ID NO: 101), KLKDEASQLR (SEQ ID NO: 102), KLKDENAQLR (SEQ ID NO: 103), KLKDENSQAR (SEQ ID NO: 105), KLKDENSQLA (SEQ ID NO: 106), or a combination thereof.

For example, the amino acid sequence (III) or (IV) of the peptide can comprise KLKDENSQLK (SEQ ID NO: 3), KLKDENSQL (SEQ ID NO: 119), KLKDENSQ (SEQ ID NO: 120), KLQEELNKV (SEQ ID NO: 53), KLKDDNSQLK (SEQ ID NO: 16), KLKTENSQLK (SEQ ID NO: 95), KIKDENSQLK (SEQ ID NO: 92), KLADENSQLK (SEQ ID NO: 91), ALKDENSQLK (SEQ ID NO: 90), KAKDENSQLR (SEQ ID NO: 98), KLKAENSQLR (SEQ II) NO: 100), KLKDENAQLR (SEQ ID NO: 103), KLKDENSQLA (SEQ ID NO: 106), or a combination thereof.

As another example, the amino acid sequence (III) or (IV) of the peptide can comprise KLKDENSQLK (SEQ ID NO: 3), KLKDDNSQLK (SEQ ID NO: 16), KLKTENSQLK (SEQ ID NO: 95), KIKDENSQLK (SEQ ID NO: 92), KLADENSQLK (SEQ ID NO: 91), KLKDENTQLK (SEQ ID NO: 94), ALKDENSQLK (SEQ ID NO: 90), KAKDENSQLR (SEQ ID NO: 98), KLADENSQLR (SEQ ID NO: 99), KLKAENSQLR (SEQ ID NO: 100), KLKDANSQLR (SEQ ID NO: 101), KLKDEASQLR (SEQ ID NO: 102), KLKDENAQLR (SEQ ID NO: 103), KLKDENSQAR (SEQ ID NO: 105), KLKDENSQLA (SEQ ID NO: 106), or a combination thereof.

The amino acid sequence (III) or (IV) of the peptide more preferably comprises KLKDENSQLK (SEQ ID NO: 3), KLKDDNSQLK (SEQ ID NO: 16), KLKTENSQLK (SEQ ID NO: 95), KIKDENSQLK (SEQ ID NO: 92), KLADENSQLK (SEQ ID NO: 91), ALKDENSQLK (SEQ ID NO: 90), KAKDENSQLR (SEQ ID NO: 98), KLKAENSQLR (SEQ ID NO: 100), KLKDENAQLR (SEQ ID NO: 103), KLKDENSQLA (SEQ ID NO: 106), or a combination thereof.

For example, the amino acid sequence (III) or (IV) of the peptide can comprise KLKDENSQLK (SEQ ID NO: 3), KLKDDNSQLK (SEQ ID NO: 16), KLKTENSQLK (SEQ ID NO: 95), KIKDENSQLK (SEQ ID NO: 92), KLADENSQLK (SEQ ID NO: 91), or a combination thereof.

The amino acid sequence (III) or (IV) of the peptide can comprise KLKDDNSQLK (SEQ ID NO: 16), KLKTENSQLK (SEQ ID NO: 95), KIKDENSQLK (SEQ ID NO: 92), or a combination thereof.

The amino acid sequence (III) or (IV) of the peptide can comprise KLKDENSQLK (SEQ ID NO: 3), KLK- DENTQLK (SEQ ID NO: 94), KLKDDNSQLK (SEQ ID NO: 16), KIKDENSQLK (SEQ ID NO: 92), ALKDENSQLK (SEQ ID NO: 90), KLADENSQLK (SEQ ID NO: 91), KAKDENSQLR (SEQ ID NO: 98), KLADENSQLR (SEQ ID NO: 99), KLKAENSQLR (SEQ ID NO: 100), KLKDANSQLR (SEQ ID NO: 101), KLKAEASQLR (SEQ ID NO: 102), KLKDENAQLR (SEQ ID NO: 103), KLKDENSQAR (SEQ ID NO: 105), KLKDENSQLA (SEQ ID NO: 106), or a combination thereof.

For example, the amino acid sequence (III) or (IV) of the peptide can comprise KLKDENSQLK (SEQ ID NO: 3), KLKDDNSQLK (SEQ ID NO: 16), KIKDENSQLK (SEQ ID NO: 92), ALKDENSQLK (SEQ ID NO: 90), KLADENSQLK (SEQ ID NO: 91), KAKDENSQLR (SEQ ID NO: 98), KLKAENSQLR (SEQ ID NO: 100), KLKDENAQLR (SEQ ID NO: 103), KLKDENSQLA (SEQ ID NO: 106), or a combination thereof.

The amino acid sequence (III) or (IV) of the peptide can comprise KLKDENSQLK (SEQ ID NO: 3).

The amino acid sequence (III) or (IV) of the peptide can consist of KLKDENSQLK (SEQ ID NO: 3), KLKDENSQL (SEQ ID NO: 119), KLKDENSQ (SEQ ID NO: 120), KLKDDNSQLK (SEQ ID NO: 16), KLKDENAQLK (SEQ ID NO: 18), KLKEENNQLK (SEQ ID NO: 20), KLKEENTQLK (SEQ ID NO: 21), KLKEENSQLR (SEQ ID NO: 22), KLKNENKQLK (SEQ ID NO: 27), KLKNENRQLK (SEQ ID NO: 28), KLIKVENGQLK (SEQ ID NO: 32), KVKDENSQLK (SEQ ID NO: 36), KLKDEQEKLK (SEQ ID NO: 39), KLKDENSQLK (SEQ ID NO: 40), KLKNENRQLK (SEQ ID NO: 42), KLEDEQNSQIK (SEQ ID NO: 45), KLKDETSKLK (SEQ ID NO: 46), KLRDENSQLK (SEQ ID NO: 47), KLKQENTQLK (SEQ ID NO: 48), KLQEENHQL (SEQ ID NO: 49), KLKDDEVAQL (SEQ ID NO: 51), KLVEETKQL (SEQ ID NO: 52), LKDENSKL (SEQ ID NO: 54), LKNKNSQLK (SEQ ID NO: 55), LKEENSQ (SEQ ID NO: 56), LKGENEQLK (SEQ ID NO: 58), KLKEEITQL (SEQ ID NO: 59), LKDQNSKL (SEQ ID NO: 61), KLKDENTQLK (SEQ ID NO: 94), KLKTENSQLK (SEQ ID NO: 95), KIKDENSQLK (SEQ ID NO: 92), ALKDENSQLK (SEQ ID NO: 90), KLADENSQLK (SEQ ID NO: 91), KAKDENSQLR (SEQ ID NO: 98), KLADENSQLR (SEQ ID NO: 99), KLKAENSQLR (SEQ ID NO: 100), KLKDANSQLR (SEQ ID NO: 101), KLKDEASQLR (SEQ ID NO: 102), KLKDENAQLR (SEQ ID NO: 103), KLKDENSQAR (SEQ ID NO: 105), KLKDENSQLA (SEQ ID NO: 106), KLKDENSQLKS (SEQ ID NO: 121), KLKDENSQLKSE (SEQ ID NO: 122), KLKDENSQLKSEV (SEQ ID NO: 123), or KLKDENSQLKSEVS (SEQ ID NO: 124).

The amino acid sequence (III) or (IV) of the peptide preferably consists of KLKDENSQLK (SEQ ID NO: 3), KLKDENSQL (SEQ ID NO: 119), KLKDENSQ (SEQ ID NO: 120), KLQEELNKV (SEQ ID NO: 53), KLKDDNSQLK (SEQ ID NO: 16), KLKTENSQLK (SEQ ID NO: 95), KIKDENSQLK (SEQ ID NO: 92), KLADENSQLK (SEQ ID NO: 91), KLKDENTQLK (SEQ ID NO: 94), ALKDENSQLK (SEQ ID NO: 90), KAKDENSQLR (SEQ ID NO: 98), KLADENSQLR (SEQ ID NO: 99), KLKAENSQLR (SEQ ID NO: 100), KLKDANSQLR (SEQ ID NO: 101), KLKDEASQLR (SEQ ID NO: 102), KLKDENAQLR (SEQ ID NO: 103), KLKDENSQAR (SEQ ID NO: 105), or KLKDENSQLA (SEQ ID NO: 106).

For example, the amino acid sequence (III) or (IV) of the peptide can consist of KLKDENSQLK (SEQ ID NO: 3), KLKDENSQL (SEQ ID NO: 119), KLKDENSQ (SEQ ID NO: 120), KLQEELNKV (SEQ ID NO: 53), KLKDDNSQLK (SEQ ID NO: 16), KLKTENSQLK (SEQ ID NO: 95), KIKDENSQLK (SEQ ID NO: 92), KLADENSQLK (SEQ ID NO: 91), ALKDENSQLK (SEQ ID NO: 90), KAKDENSQLR (SEQ ID NO: 98), KLKAENSQLR (SEQ ID NO: 100), KLKDENAQLR (SEQ ID NO: 103), or KLKDENSQLA (SEQ ID NO: 106).

As another example, the amino acid sequence (III) or (IV) of the peptide can consist of KLKDENSQLK (SEQ ID NO: 3), KLKDDNSQLK (SEQ ID NO: 16), KLKTENSQLK (SEQ ID NO: 95), KIKDENSQLK (SEQ ID NO: 92), KLADENSQLK (SEQ ID NO: 91), KLKDENTQLK (SEQ ID NO: 94), ALKDENSQLK (SEQ ID NO: 90), KAKDENSQLR (SEQ ID NO: 98), KLADENSQLR (SEQ ID NO: 99), KLKAENSQLR (SEQ ID NO: 100), KLKDANSQLR (SEQ ID NO: 1101), KLKDEASQLR (SEQ ID NO: 102), KLKDENAQLR (SEQ ID NO: 103), KLKDENSQAR (SEQ ID NO: 105), or KLKDENSQLA (SEQ ID NO: 106).

The amino acid sequence (III) or (IV) of the peptide more preferably consists of KLKDENSQLK (SEQ ID NO: 3), KLKDDNSQLK (SEQ ID NO: 16), KLKTENSQLK (SEQ ID NO: 95), KIKDENSQLK (SEQ ID NO: 92), KLADENSQLK (SEQ ID NO: 91), ALKDENSQLK (SEQ ID NO: 90), KAKDENSQLR (SEQ ID NO: 98), KLKAENSQLR (SEQ ID NO: 100), KLKDENAQLR (SEQ ID NO: 103), or KLKDENSQLA (SEQ ID NO: 106).

For example, the amino acid sequence (III) or (IV) of the peptide can consist of KLKDENSQLK (SEQ ID NO: 3), KLKDDNSQLK (SEQ ID NO: 16), KLKTENSQLK (SEQ ID NO: 95), KIKDENSQLK (SEQ ID NO: 92), or KLADENSQLK (SEQ ID NO: 91).

The amino acid sequence (III) or (IV) of the peptide can consist of KLKDDNSQLK (SEQ ID NO: 16), KLKTENSQLK (SEQ ID NO: 95), or KIKDENSQLK (SEQ ID NO: 92).

The amino acid sequence (III) or (IV) of the peptide can consist of KLKDENSQLK (SEQ ID NO: 3), KLKDENTQLK (SEQ ID NO: 94), KLKDDNSQLK (SEQ ID NO: 16), KIKDENSQLK (SEQ ID NO: 92), ALKDENSQLK (SEQ ID NO: 90), KLADENSQLK (SEQ ID NO: 91), KAKDENSQLR (SEQ ID NO: 98), KLADENSQLR (SEQ ID NO: 99), KLKAENSQLR (SEQ ID NO: 100), KLKDANSQLR (SEQ ID NO: 101), KLKDEASQLR (SEQ ID NO: 102), KLKDENAQLR (SEQ ID NO: 103), KLKDENSQAR (SEQ ID NO: 105), or KLKDENSQLA (SEQ II) NO: 106).

For example, the amino acid sequence (III) or (IV) of the peptide can consist of KLKDENSQLK (SEQ ID NO: 3), KLKDDNSQLK (SEQ ID NO: 16), KIKDENSQLK (SEQ ID NO: 92), ALKDENSQLK (SEQ ID NO: 90), KLADENSQLK (SEQ ID NO: 91), KAKDENSQLR (SEQ ID NO: 98), KLKAENSQLR (SEQ ID NO: 100), KLKDENAQLR (SEQ ID NO: 103), or KLKDENSQLA (SEQ ID NO: 106).

The amino acid sequence (III) or (IV) of the peptide can consist of KLKDENSQLK (SEQ ID NO: 3).

The amino acid sequence (III) or (IV) of the peptide optionally does not comprise or consist of KLQEELNKV.

The peptides comprising the sequence (III) or (IV) can have a length of 14 amino acids, 13 amino acids, 12 amino acids, 11 amino acids, 10 amino acids, 9 amino acids, 8 amino acids, or 7 amino acids.

Any of the peptides described herein (i.e., any peptide comprising a sequence (I) to (V)) are preferably capable of stimulating subcutaneous adipogenesis In any of the peptides described herein (i.e., any peptide comprising a sequence (I) to (V)), the peptide can have a substantially alpha-helical conformation.

In any of the peptides described herein (i.e., any peptide comprising a sequence (I) to (V)), the peptide can be a beta-peptide.

In any of the peptides described herein (i.e., any peptide comprising a sequence (I) to (V)), the peptide can be in the retro form, the inverso form, or the retro-inverso form.

In any of the peptides described herein (i.e., any peptide comprising a sequence (I) to (V)), all of the amino acids in the peptide can be L amino acids. Alternatively, the peptide can comprise one or more D amino acids, or all of the amino acids in the peptide can be D amino acids. Thus, the peptide can comprise a mixture of L amino acids and D amino acids.

Peptide Variants

The peptides described herein can be composed of amino acids joined to each other by peptide bonds or modified peptide bonds, i.e., peptide isosteres, and may contain amino acids other than the 20 gene-encoded standard amino acids. The peptides may be modified by either natural processes, such as posttranslational processing, or by chemical modification techniques that are well known in the art. Modifications can occur anywhere in a peptide, including the peptide backbone, the amino acid side-chains and the amino or carboxyl termini. The same type of modification may be present in the same or varying degrees at several sites in a peptide. Also, a peptide may contain many types of modifications.

Peptides may be branched, for example, as a result of ubiquitination, and they may be cyclic, with or without branching. Cyclic, branched, and branched cyclic peptides may result from posttranslation natural processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine-cysteine disulfide bonds, formation of pyroglutamate, formylation, gamma-carboxylation, glycosylation, GPI anchor formation, hydroxylation, iodination, methylation, myristoylation, oxidation, PEGylation, proteolytic processing, phosphorylation, prenylation, palmitoylation, racemization, selenoylation, sulfation, transfer-RNA mediated addition of amino acids to proteins such as arginylation, and ubiquitination. (see, e.g., Creighton et al. (1993) *Proteins—Structure and Molecular Properties,* 2nd Ed., T. E. Creighton, W. H. Freeman and Company, New York; Johnson, ed. (1983) *Posttranslational Covalent Modification Of Proteins,* Academic Press, New York; Seifter et al. (1990) *Meth. Enzymol.,* 182: 626-646; Rattan et al. (1992) *Ann. N.Y. Acad. Sci.,* 663: 48-62; and the like).

Using known methods of protein engineering and recombinant DNA technology, variants may be generated to improve or alter the characteristics of the peptides described herein. Such variants include deletions, insertions, inversions, repeats, and substitutions (e.g., conservative substitutions) selected according to general rules well known in the art so as have little effect on activity.

Peptoids are also contemplated wherein the peptoid has an essentially corresponding monomer sequence, where a natural amino acid is replaced by an N-substituted glycine derivative, if the N-substituted glycine derivative resembles the original amino acid in hydrophilicity, hydrophobicity, polarity, etc. The following are illustrative, but non-limiting N-substituted glycine replacements: N-(1-methylprop-1-yl) glycine→isoleucine (I), N-(prop-2-yl)glycine→valine (V), N-benzylglycine→phenylalanine (F), N-(2-hydroxyethyl) glycine→serine (S), and the like. In certain aspects of the invention, substitutions need not be "exact." Thus for example, in certain aspects of the invention, N-(2-hydroxyethyl)glycine may substitute for S, T, C, and/or M; N-(2-methylprop-1-yl)glycine may substitute for V, L, and/or I; N-(2-hydroxyethyl)glycine can be used to substitute for T or S. In general, one may use an N-hydroxyalkyl-substituted glycine to substitute for any polar amino acid, an N-benzyl- or N-aralkyl-substituted glycine to replace any aromatic amino acid, an N-alkyl-substituted glycine such as N-butyl-glycine to replace any nonpolar amino acid (e.g., L, V, I, etc.), and an N-(aminoalkyl)glycine to replace any basic polar amino acid (e.g., L and R).

Functionalization and Protecting Groups

While the various peptides described herein are shown without protecting groups, they can bear one or more protecting groups. The protecting groups can be coupled to the C- and/or N-terminus of the peptide and/or to one or more internal residues of the peptide. Thus, for example, any of the peptides described herein can bear, e.g., an acyl group protecting the amino terminus and/or an amide group protecting the carboxyl terminus. These blocking groups enhance the helix-forming tendencies of the peptides.

Without being bound by a particular theory, it is believed that blockage, particularly of the amino and/or carboxyl termini of the peptide can improve ex vivo and/or in vivo peptide stability and/or can improve skin penetration when administered topically.

Suitable protecting groups include, but are not limited to, acetyl, amide, and alkyl groups with acetyl and alkyl groups being particularly preferred for N-terminal protection and amide groups being preferred for carboxyl terminal protection. Alkyl protecting groups include, but are not limited to, alkyl chains as in fatty acids such as propionyl, formyl, and others. For example, the alkyl can be 3- to 20-carbon alkyl. Carboxyl protecting groups include amides, esters, and ether-forming protecting groups. Such blocking groups include alkyl groups of various lengths, e.g., groups having the formula: $CH_3\text{-}(CH_2)_n\text{—CO—}$ where n ranges from about 1 to about 20, preferably from about 1 to about 16 or 18, more preferably from about 3 to about 13, and most preferably from about 3 to about 10.

Other suitable protecting groups include, but are not limited to, fluorenylmethyloxycarbonyl (FMOC), t-butoxycarbonyl (t-BOC), 9-fluoreneacetyl, 1-fluorenecarboxylic, 9-florenecarboxylic, 9-fluorenone-1-carboxylic, benzyloxycarbonyl, xanthyl (Xan), trityl (Trt), 4-methyltrityl (Mtt), 4-methoxytrityl (Mmt), 4-methoxy-2,3,6-trimethyl-benzenesulphonyl (Mtr), mesitylene-2-sulphonyl (Mts), 4,4-dimethoxybenzhydryl (Mbh), tosyl (Tos), 2,2,5,7,8-pentamethyl chroman-6-sulphonyl (Pmc), 4-methylbenzyl (MeBzl), 4-methoxybenzyl (MeOBzl), benzyloxy (BzlO), benzyl (Bzl), benzoyl (Bz), 3-nitro-2-pyridinesulphenyl (Npys), 1-(4,4-dimentyl-2,6-diaxocyclohexylidene)ethyl (Dde), 2,6-dichlorobenzyl (2,6-DiCl-Bzl), 2-chlorobenzyloxycarbonyl (2-Cl-Z), 2-bromobenzyloxycarbonyl (2-Br-Z), benzyloxymethyl (Bom), cyclohexyloxy (cHxO),t-butoxymethyl (Bum), t-butoxy (tBuO), t-Butyl (tBu), acetyl (Ac), and trifluoroacetyl (TFA).

Protecting/blocking groups are well known to those of skill as are methods of coupling such groups to the appropriate residue of the peptide (see, e.g., Greene et al., (1991) *Protective Groups in Organic Synthesis,* 2nd ed., John Wiley & Sons, Inc. Somerset, N.J.). For example, acetylation can be accomplished during synthesis when the peptide is on the resin using acetic anhydride. Amide protection can be achieved by the selection of a proper resin for the synthesis. During the synthesis of the peptide, rink amide resin can be used. After the completion of the synthesis, the semipermanent protecting groups on acidic bifunctional amino acids such as Asp and Glu, the basic amino acid Lys, and the hydroxyl of Tyr are all simultaneously removed. The peptides released from such a resin using acidic treatment have the N-terminus protected with acetyl and the carboxy-terminus protected with $NH_2$ with the simultaneous removal of all of the other protecting groups.

The peptides may comprise one or more D-amino acids (dextro rather than levo). Every other, or even every amino acid (e.g., every enantiomeric amino acid) of the peptide can be a D-amino acid. For example, at least 50%, at least 80%, at least 90% or even all of the enantiomeric amino acids can be D-amino acids.

The peptides can also be functionalized with a polymer (e.g., polyethylene glycol and/or a cellulose or modified cellulose) to increase bioavailability.

Peptide Mimetics

Peptide analogs are commonly used in the pharmaceutical industry as non-peptide drugs with properties analogous to those of the template peptide. These types of non-peptide compounds are termed "peptide mimetics" or "peptidomimetics" (Fauchere (1986) *Adv. Drug Res.* 15: 29; Veber and Freidinger (1985) *TINS p.*392; and Evans et al. (1987) *J. Med. Chem.* 30: 1229) and are usually developed with the aid of computerized molecular modeling. Peptide mimetics that are structurally similar to peptides of the invention may be used to produce an equivalent therapeutic or prophylactic effect.

Peptidomimetics are structurally similar to a peptide, but have one or more peptide linkages optionally replaced by a linkage such as —$CH_2NH$—, —$CH_2S$—, —$CH_2$—$CH_2$—, —$CH$=$CH$— (cis and trans), —$COCH_2$—, —$CH(OH)$ $CH_2$—, or —$CH_2SO$— by methods known in the art and further described in the following references: Spatola (1983) p. 267 in *Chemistry and Biochemistry of Amino Acids, Peptides, and Proteins*, B. Weinstein, eds., Marcel Dekker, New York; Spatola (1983) *Vega Data* 1(3) *Peptide Backbone Modifications*. (general review); Morley (1980) *Trends Pharm Sci pp.* 463-468 (general review); Hudson et al. (1979) *Int J Pept Prot Res* 14:177-185 (—$CH_2NH$—, —$CH_2$—$CH_2$—); Spatola et al. (1986) Life Sci 38:1243-1249 (—$CH_2$—$S$—); Hann, (1982) *J Chem Soc Perkin Trans* I 307-314 (—$CH$=$CH$—, cis and trans); Almquist et al. (1980) *J Med Chem.* 23: 1392-1398 (—$COCH_2$—); Jennings-White et al. (1982) *Tetrahedron Lett.* 23: 2533 (—$COCH_2$—); Szelke et al. (1982) European Appln. EP 45665 (—$CH(OH)CH_2$—); Holladay et al. (1983) *Tetrahedron Lett* 24:4401-4404 (—$C(OH)CH_2$—); and Hruby (1982) *Life Sci.,* 31:189-199 (—$CH_2$—$S$—)).

A particularly useful non-peptide linkage is —$CH_2NH$—. Such peptide mimetics may have significant advantages over peptides, such as more economical production, greater chemical stability, enhanced pharmacological properties (half-life, absorption, potency, efficacy, etc.), and/or reduced antigenicity.

Circular permutations of the peptides described herein or constrained peptides (including cyclized peptides) comprising the motifs described herein or a substantially identical motif can be generated by methods known in the art (Rizo and Gierasch (1992) *Ann. Rev. Biochem.* 61: 387), for example, by adding internal cysteine residues capable of forming intramolecular disulfide bridges which cyclize the peptide.

Peptide Preparation

In various aspects of the invention, the peptides described herein can be chemically synthesized using standard chemical peptide synthesis techniques or, particularly where the peptide does not comprise D-amino acid residues, the peptide can be recombinantly expressed. Where polypeptides containing one or more D-amino acids are to be recombinantly expressed, a host organism (e.g. bacteria, plant, fungal cells, etc.) can be cultured in an environment where one or more of the amino acids is provided to the organism exclusively in a D-form. Recombinantly expressed peptides in such a system then incorporate those D-amino acids. Also, D-amino acids can be incorporated in recombinantly expressed peptides using modified amino acyl-tRNA synthetases that recognize D-amino acids.

The peptides (containing D- and/or L-amino acids) can be chemically synthesized by any of a number of fluid or solid phase peptide synthesis techniques known to those of skill in the art. Solid phase synthesis in which the C-terminal amino acid of the sequence is attached to an insoluble support followed by sequential addition of the remaining amino acids in the sequence is a preferred method for the chemical synthesis of the polypeptides of the invention. Techniques for solid phase synthesis are well known to those of skill in the art and are described, for example, by Barany and Merrifield (1963) *Solid-Phase Peptide Synthesis; pp.* 3-284 in *The Peptides: Analysis, Synthesis, Biology. Vol.* 2: *Special Methods in Peptide Synthesis*, Part A.; Merrifield et al. (1963) *J. Am. Chem. Soc.,* 85: 2149-2156, and Stewart et al. (1984) *Solid Phase Peptide Synthesis,* 2nd ed. Pierce Chem. Co., Rockford, Ill.

The peptides can be synthesized by the solid phase peptide synthesis procedure using a benzhydrylamine resin (Beckman Bioproducts, 0.59 mmol of $NH_2$/g of resin) as the solid support. The carboxy terminal amino acid (e.g., t-butylcarbonyl-Phe) is attached to the solid support through a 4-(oxymethyl)phenacetyl group. This is a more stable linkage than the conventional benzyl ester linkage, yet the finished peptide can still be cleaved by hydrogenation. Transfer hydrogenation using formic acid as the hydrogen donor can be used for this purpose.

It is noted that in the chemical synthesis of peptides, particularly peptides comprising D-amino acids, the synthesis usually produces a number of truncated peptides in addition to the desired full-length product. Thus, the peptides are typically purified using, e.g., HPLC.

D-amino acids, beta amino acids, non-natural amino acids, non-standard amino acids, and the like can be incorporated at one or more positions in the peptide simply by using the appropriately derivatized amino acid residue in the chemical synthesis. Modified residues for solid phase peptide synthesis are commercially available from a number of suppliers (see, e.g., Advanced Chem Tech, Louisville; Nova Biochem, San Diego; Sigma, St Louis; Bachem California Inc., Torrance, etc.). The D-form and/or otherwise modified amino acids can be completely omitted or incorporated at any position in the peptide as desired.

When the peptides are synthesized using recombinant expression systems, a DNA sequence that encodes the desired peptide is typically created, and placed in an expression cassette under the control of a promoter to express the peptide in a host cell. The expressed peptide is isolated and, if required, renatured. DNA encoding a peptide of the invention can be prepared by any suitable method, including, for example, cloning and restriction of appropriate sequences or direct chemical synthesis. This nucleic acid can be easily ligated into an appropriate vector containing appropriate expression control sequences (e.g. promoter, enhancer, etc.), and, optionally, containing one or more selectable markers (e.g. antibiotic resistance genes).

A nucleic acid sequence encoding a peptide described herein can be expressed in a variety of host cells, including, but not limited to, *E. coli*, other bacterial hosts, yeast, fungus, and various higher eukaryotic cells such as insect cells (e.g. SF3), the COS, CHO and HeLa cells lines and myeloma cell lines. The recombinant protein gene will typically be operably linked to appropriate expression control sequences for each host. For *E. coli* this can include a promoter such as the T7, trp, or lambda promoters, a ribosome binding site and preferably a transcription termination signal. For eukaryotic cells, illustrative control sequences can include a promoter and often an enhancer (e.g., an enhancer derived from immunoglobulin genes, SV40, cytomegalovirus, etc.), and a polyadenylation sequence, and may include splice donor and acceptor sequences.

The plasmids can be transferred into the chosen host cell by well-known methods such as calcium chloride transformation for *E. coli* and calcium phosphate treatment or electroporation for mammalian cells. Cells transformed by the plasmids can be selected by resistance to antibiotics conferred by genes contained on the plasmids, such as the amp, gpt, neo and hyg genes.

Once expressed, the recombinant peptides can be purified according to standard procedures of the art, including, but not limited to, ammonium sulfate precipitation, affinity columns, column chromatography, and gel electrophoresis (see, generally, R. Scopes, (1982) *Protein Purification*, Springer-Verlag, N.Y.; Deutscher (1990) *Methods in Enzymology Vol. 182: Guide to Protein Purification.*, Academic Press, Inc. N.Y.). Substantially pure compositions of at least about 90 to 95% homogeneity are preferred, and 98 to 99% or more homogeneity are most preferred.

One of skill in the art would recognize that after chemical synthesis, biological expression, or purification, the peptide may possess a conformation substantially different than desired native conformation. In this case, it may be necessary to denature and reduce the peptide and then to cause the molecule to re-fold into the preferred conformation. Methods of reducing and denaturing proteins and inducing re-folding are well known to those of skill in the art (see, e.g., Debinski et al. (1993) *J. Biol. Chem.*, 268: 14065-14070; Kreitman and Pastan (1993) *Bioconjug. Chem.*, 4: 581-585; and Buchner, et al., (1992) *Anal. Biochem.*, 205: 263-270). Debinski et al., for example, describes the denaturation and reduction of inclusion body proteins in guanidine-DTE. The protein is then refolded in a redox buffer containing oxidized glutathione and L-arginine.

One of skill would recognize that modifications can be made to the peptides of the invention without diminishing their biological activity. Some modifications may be made to facilitate the cloning, expression, or incorporation of the targeting molecule into a fusion protein. Such modifications are well known to those of skill in the art and include, for example, a methionine added at the amino terminus to provide an initiation site, or additional amino acids (e.g., poly His) placed on either terminus to create conveniently located restriction sites or termination codons or purification sequences.

Pharmaceutical and Cosmetic Compositions

Pharmaceutical and cosmetic compositions containing any one or more of the above-described peptides and a pharmaceutically or cosmetically acceptable carrier are also provided.

Further pharmaceutical and cosmetic compositions are also provided. The compositions comprise a pharmaceutically or cosmetically acceptable carrier and a peptide for stimulating subcutaneous adipogenesis. The peptide has a length of 7 to 14 amino acids and comprises the sequence (V):

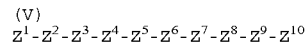

wherein $Z^1$ is lysine (K), alanine (A), or absent; $Z^2$ is leucine (L), isoleucine (I), alanine (A), or valine (V); $Z^3$ is lysine (K), glutamine (Q), arginine (R), glutamic acid (E), valine (V), or alanine (A); $Z^4$ is a negatively charged amino acid, threonine (T), asparagine (N), isoleucine (I), valine (V), alanine (A), tryptophan (Y), glutamine (Q), or glycine (G); $Z^5$ is a negatively charged amino acid, leucine (L), glutamine (Q), lysine (K), or alanine (A); $Z^6$ is asparagine (N), leucine (L), serine (S), glutamic acid (E), isoleucine (I), glutamine (Q), threonine (T), valine (V), lysine (K), or alanine (A); $Z^7$ is any amino acid; $Z^8$ is glutamine (Q) or lysine (K); $Z^9$ is leucine (L), valine (V), isoleucine (I), glycine (G), alanine (A), or is absent; and $Z^{10}$ is lysine (K), arginine (R), alanine (A), glutamic acid (E) or is absent. When the length of the peptide is 14 amino acids, $Z^1$ is lysine (K). When $Z^{10}$ is arginine (R), one of $Z^2$, $Z^3$, $Z^4$, $Z^5$, $Z^6$, $Z^7$, or $Z^9$ is alanine (A). The peptide optionally comprises an aspartic acid residue (D) inserted between $Z_4$ and $Z_5$, or a glutamine residue (Q) inserted between $Z_5$ and $Z_6$.

In the peptides comprising the sequence (V), the peptide preferably does not comprise an aspartic acid residue (D) inserted between $Z_4$ and $Z_5$, or a glutamine residue (Q) inserted between $Z_5$ and $Z_6$.

In the peptides comprising the sequence (V), $Z^1$ is lysine (K) or alanine (A). $Z^1$ is more preferably lysine (K).

In the peptides comprising the sequence (V), $Z^2$ can be leucine (L), isoleucine (I), or alanine (A). $Z^2$ is preferably leucine (L) or isoleucine (I). For example, $Z^2$ can be leucine (L).

In the peptides comprising the sequence (V), $Z^3$ can be lysine (K), glutamine (Q), or alanine (A). $Z^3$ is preferably lysine (K) or alanine (A). For example, $Z^3$ can be lysine (K).

In the peptides comprising the sequence (V), $Z^4$ can be a negatively charged amino acid, threonine (T), or alanine (A). For example, $Z^4$ can be aspartic acid (D), glutamic acid (E), threonine (T), or alanine (A). $Z^4$ is preferably aspartic acid (D), threonine (T), or alanine (A). For example, $Z^4$ can be aspartic acid (D) or threonine (T). $Z^4$ can aspartic acid (D) or alanine (A). $Z^4$ can be aspartic acid (D) or glutamic acid (E). For example, $Z^4$ can be aspartic acid (D).

In the peptides comprising the sequence (V), $Z^5$ can be a negatively charged amino acid or alanine (A). $Z^5$ is preferably a negatively charged amino acid. The negatively charged amino acid is aspartic acid (D) or glutamic acid (E). For example, the negatively charged amino acid can be glutamic acid (E).

In the peptides comprising the sequence (V), $Z^6$ can asparagine (N), leucine (L), or alanine (A). For example, $Z^6$ can be asparagine (N) or leucine (L). As another example, $Z^6$ can be asparagine (N) or alanine (A). $Z^6$ is preferably asparagine (N).

In the peptides comprising the sequence (V), $Z^7$ can be serine (S), asparagine (N), alanine (A), or threonine (T). For example, $Z^7$ can be serine (S), asparagine (N), or alanine (A). As another example, $Z^7$ can be serine (S), alanine (A), or threonine (T). $Z^7$ can be serine (S) or alanine (A). $Z^7$ can be serine (S).

In the peptides comprising the sequence (V), $Z^8$ is preferably glutamine (Q).

In the peptides comprising the sequence (V), $Z^9$ can be leucine (L), valine (V), alanine (A), or can be absent. For example, $Z^9$ can be leucine (L), valine (V), or alanine (A). As another example, $Z^9$ can be leucine (L), valine (V), or is absent. $Z^9$ can be leucine (L) or alanine (A). $Z^9$ is preferably leucine (L).

In the peptides comprising the sequence (V), $Z^{10}$ can be lysine (K), arginine (R), alanine (A), or can be absent. For example, $Z^{10}$ can be lysine (K) or arginine (R), or alanine (A). $Z^{10}$ is preferably lysine (K).

In the peptides comprising the sequence (V), when $Z^6$ is leucine (L), $Z^9$ is optionally not valine (V). When $Z^9$ is valine (V), $Z^6$ is optionally not leucine (L).

In the peptides comprising the sequence (V), when $Z^{10}$ is arginine (R), one of $Z^2$, $Z^4$, or $Z^7$ is preferably alanine (A).

In the peptides comprising the sequence (V), preferably no more than one of $Z^1$, $Z^2$, $Z^3$, $Z^5$, $Z^6$, $Z^7$, $Z^9$, and $Z^{10}$ is alanine (A).

In preferred peptides comprising the sequence (V), $Z^1$ is lysine (K) or alanine (A); $Z^2$ is leucine (L), isoleucine (I), or alanine (A); $Z^3$ is lysine (K), glutamine (Q), or alanine (A); $Z^4$ is aspartic acid (D), glutamic acid (E), threonine (T), or alanine (A); $Z^5$ is aspartic acid (D), glutamic acid (E), or alanine (A); $Z^6$ is asparagine (N), leucine (L), or alanine (A); $Z^7$ is serine (S), asparagine (N), threonine (T), or alanine (A); $Z^9$ is leucine (L), valine (V), alanine (A), or absent; and $Z^{10}$ is lysine (K), arginine (R), alanine (A), or absent.

For example, in the peptides comprising the sequence (V), $Z^5$ can be aspartic acid (D) or glutamic acid (E); $Z^6$ can be asparagine (N) or leucine (L); $Z^7$ can be serine (S), asparagine (N), or alanine (A); and $Z^9$ can be leucine (L), valine (V), or absent.

As another example, in the peptides comprising the sequence (V), $Z^3$ can be lysine (K) or alanine (A); $Z^4$ can be aspartic acid (D), threonine (T), or alanine (A); $Z^6$ can be asparagine (N) or alanine (A); $Z^7$ can be serine (S), threonine (T), or alanine (A); $Z^8$ can be glutamine (Q); $Z^9$ can be leucine (L) or alanine (A); and $Z^{10}$ can be lysine (K), arginine (R), or alanine (A).

As yet another example, in the peptides comprising the sequence (V), $Z^3$ can be lysine (K) or alanine (A); $Z^4$ can be aspartic acid (D), threonine (T), or alanine (A); $Z^5$ can be aspartic acid (D) or glutamic acid (E); $Z^6$ can be asparagine (N); $Z^7$ can be serine (S) or alanine (A); $Z^8$ can be glutamine (Q); $Z^9$ can be leucine (L); and $Z^{10}$ can be lysine (K), arginine (R), or alanine (A).

As a further example, in the peptides comprising the sequence (V), $Z^1$ can be lysine (K); $Z^2$ can be leucine (L) or isoleucine (I); $Z^3$ can be lysine (K) or alanine (A); $Z^4$ can be aspartic acid (D) or threonine (T); $Z^5$ can be aspartic acid (D) or glutamic acid (E); $Z^6$ can be asparagine (N); $Z^7$ can be serine (S); $Z^8$ can be glutamine (Q); $Z^9$ can be leucine (L); and $Z^{10}$ can be lysine (K).

As another example, in the peptides comprising the sequence (V), $Z^1$ can be lysine (K) or alanine (A); $Z^2$ can be leucine (L), isoleucine (I), or alanine (A); $Z^3$ can be lysine (K) or alanine (A); $Z^4$ can be aspartic acid (D) or alanine (A); $Z^5$ can be aspartic acid (D), glutamic acid (E), or alanine (A); $Z^6$ can be asparagine (N) or alanine (A); $Z^7$ can be serine (S), threonine (T), or alanine (A); $Z^8$ can be glutamine (Q); $Z^9$ can be leucine (L) or alanine (A); and $Z^{10}$ can be lysine (K), arginine (R), or alanine (A).

As yet another example, in the peptides comprising the sequence (V), $Z^5$ can be aspartic acid (D) or glutamic acid (E); $Z^6$ can be asparagine (N); $Z^7$ can be serine (S) or alanine (A); and $Z^9$ can be leucine (L).

In other preferred peptides comprising sequence (V), $Z^1$ is lysine (K); $Z^2$ is leucine (L); $Z^3$ is lysine (K), glutamine (Q), or arginine (R); $Z^4$ is a negatively charged amino acid, threonine (T), asparagine (N), isoleucine (I), valine (V), or alanine (A); $Z^5$ is a negatively charged amino acid; $Z^6$ is asparagine (N) or leucine (L); $Z^9$ is leucine (L), valine (V), isoleucine (I), or is absent; and $Z^{10}$ is lysine (K), arginine (R), or is absent. For example, $Z^4$ can be a negatively charged amino acid, threonine (T), or asparagine (N); $Z^8$ can be glutamine (Q); and $Z^9$ can be leucine (L), valine (V), or is absent.

In further preferred peptides comprising sequence (V), $Z^2$ is leucine (L) or isoleucine (I); $Z^3$ is lysine (K), glutamine (Q), arginine (R), or valine (V); $Z^4$ is aspartic acid (D), glutamic acid (E), threonine (T), asparagine (N), isoleucine (I), valine (V), alanine (A), tryptophan (Y), glutamine (Q), or glycine (G); $Z^5$ is aspartic acid (D), glutamic acid (E), leucine (L), or glutamine (Q); $Z^6$ is asparagine (N), serine (S), glutamic acid (E), glutamine (Q), or threonine (T); $Z^7$ is serine (S), asparagine (N), alanine (A), threonine (T), isoleucine (I), lysine (K), leucine (L), phenylalanine (F), glycine (G), valine (V), glutamic acid (E), or histidine (H); $Z^9$ is leucine (L), valine (V), or is absent; and $Z^{10}$ is lysine (K), arginine (R), or is absent. For example, $Z^1$ can be lysine (K); $Z^3$ can be lysine (K); $Z^4$ can be aspartic acid (D), glutamic acid (E), threonine (T), asparagine (N), isoleucine (I), valine (V), or tryptophan (Y); $Z^5$ can be aspartic acid (D), glutamic acid (E), or leucine (L); $Z^6$ can be asparagine (N), serine (S), glutamic acid (E), or glutamine (Q); $Z^7$ can be serine (S), asparagine (N), alanine (A), threonine (T), isoleucine (I), lysine (K), leucine (L), phenylalanine (F), glycine (G), valine (V), or glutamic acid (E); $Z^8$ can be glutamine (Q); $Z^9$ can be leucine (L); and $Z^{10}$ can be lysine (K) or arginine (R).

The amino acid sequence (V) of the peptide can comprise KLKDENSQLK (SEQ ID NO: 3), KLKDENSQL (SEQ ID NO: 119), KLKDENSQ (SEQ ID NO: 120), KLKDDNSQLK (SEQ ID NO: 16), KLKDENAQLK (SEQ ID NO: 18), KLKEENNQLK (SEQ ID NO: 20), KLKEENTQLK (SEQ ID NO: 21), KLKEENSQLR (SEQ ID NO: 22), KLKNENKQLK (SEQ ID NO: 27), KLKNENIQLK (SEQ ID NO: 28), KLKVENGQLK (SEQ ID NO: 32), KVKDENSQLK (SEQ ID NO: 36), KLKDEQEKLK (SEQ ID NO: 39), KLKDENEQLK (SEQ ID NO: 40), KLKNENRQLK (SEQ ID NO: 42), KLEDEQNSQIK (SEQ ID NO: 45), KLKDETSKLK (SEQ ID NO: 46), KLRDENSQLK (SEQ ID NO: 47), KLKQENTQLK (SEQ ID NO: 48), KLQEENHQL (SEQ ID NO: 49), KLKDDEVAQL (SEQ ID NO: 51), KLVEETKQL (SEQ ID NO: 52), LKDENSKL (SEQ ID NO: 54), LKNKNSQLK (SEQ ID NO: 55), LKEENSQ (SEQ ID NO: 56), LKGENEQLK (SEQ ID NO: 58), KLKEEITQL (SEQ ID NO: 59), LKDQNSKL (SEQ ID NO: 61), KLKDENTQLK (SEQ ID NO: 94), KLKTENSQLK (SEQ ID NO: 95), KIKDENSQLK (SEQ ID NO: 92), ALKDENSQLK (SEQ ID NO: 90), KLADENSQLK (SEQ ID NO: 91), KAKDENSQLR (SEQ ID NO: 98), KLADENSQLR (SEQ ID NO: 99), KLKAENSQLR (SEQ ID NO: 100), KLKDANSQLR (SEQ ID NO: 101), KLKDEASQLR (SEQ ID NO: 102), KLKDENAQLR (SEQ ID NO: 103), KLKDENSQAR (SEQ ID NO: 105), KLKDENSQLA (SEQ ID NO: 106), or a combination thereof.

The amino acid sequence (V) of the peptide can comprise KLKQEELNKV (SEQ ID NO: 53).

The amino acid sequence (V) of the peptide preferably comprises KLKDENSQLK (SEQ ID NO: 3), KLKDENSQL (SEQ ID NO: 119), KLKDENSQ (SEQ ID NO: 120), KLQEELNKV (SEQ ID NO: 53), KLKDDNSQLK (SEQ ID NO: 16), KLKTENSQLK, KIKDENSQLK (SEQ ID NO: 92), KLADENSQLK (SEQ ID NO: 91), KLKDENTQLK (SEQ ID NO: 94), ALKDENSQLK (SEQ ID NO: 90), KAKDENSQLR (SEQ ID NO: 98), KLADENSQLR (SEQ ID NO: 99), KLKAENSQLR (SEQ ID NO: 100), KLKDANSQLR (SEQ ID NO: 101), KLKDEASQLR (SEQ ID NO: 102), KLKDENAQLR (SEQ ID NO: 103), KLKDENSQAR (SEQ ID NO: 105), KLKDENSQLA (SEQ ID NO: 106), or a combination thereof.

For example, the amino acid sequence (V) of the peptide can comprise KLKDENSQLK (SEQ ID NO: 3), KLKDENSQL (SEQ ID NO: 119), KLKDENSQ (SEQ ID NO: 120), KLQEELNKV (SEQ ID NO: 53), KLKDDNSQLK (SEQ ID NO: 16), KLKTENSQLK (SEQ ID NO: 95), KIKDENSQLK (SEQ ID NO: 92), KLADENSQLK (SEQ ID NO: 91), ALKDENSQLK (SEQ ID NO: 90), KAKDENSQLR (SEQ ID NO: 98), KLKAENSQLR (SEQ ID NO: 100), KLKDENAQLR (SEQ ID NO: 103), KLKDENSQLA (SEQ ID NO: 106), or a combination thereof.

As another example, the amino acid sequence (V) of the peptide can comprise KLKDENSQLK (SEQ ID NO: 3), KLKDDNSQLK (SEQ ID NO: 16), KLKTENSQLK (SEQ ID NO: 95), KIKDENSQLK (SEQ ID NO: 92), KLADENSQLK (SEQ ID NO: 91), KLKDENTQLK (SEQ ID NO: 94), ALKDENSQLK (SEQ ID NO: 90), KAKDENSQLR (SEQ ID NO: 98), KLADENSQLR (SEQ ID NO: 99), KLKAENSQLR (SEQ ID NO: 100), KLKDANSQLR (SEQ ID NO: 101), KLKDEASQLR (SEQ ID NO: 102), KLKDENAQLR (SEQ ID NO: 103), KLKDENSQAR (SEQ ID NO: 105), KLKDENSQLA (SEQ ID NO: 106), or a combination thereof.

The amino acid sequence (V) of the peptide more preferably comprises KLKDENSQLK (SEQ ID NO: 3), KLKDDNSQLK (SEQ ID NO: 16), KLKTENSQLK (SEQ ID NO: 95), KIKDENSQLK (SEQ ID NO: 92), KLADENSQLK (SEQ ID NO: 91), ALKDENSQLK (SEQ ID NO: 90), KAKDENSQLR (SEQ ID NO: 98), KLKAENSQLR (SEQ ID NO: 100), KLKDENAQLR (SEQ ID NO: 103), KLKDENSQLA (SEQ ID NO: 106), or a combination thereof.

For example, the amino acid sequence (V) of the peptide can comprise KLKDENSQLK (SEQ ID NO: 3), KLKDDNSQLK (SEQ ID NO: 16), KLKTENSQLK (SEQ ID NO: 95), KIKDENSQLK (SEQ ID NO: 92), KLADENSQLK (SEQ ID NO: 91), or a combination thereof.

The amino acid sequence (V) of the peptide can comprise KLKDDNSQLK (SEQ ID NO: 16), KLKTENSQLK (SEQ ID NO: 95), KIKDENSQLK (SEQ ID NO: 92), or a combination thereof.

The amino acid sequence (V) of the peptide can comprise KLKDENSQLK (SEQ ID NO: 3), KLKDENTQLK (SEQ ID NO: 94), KLKDDNSQLK (SEQ ID NO: 16), KIKDENSQLK (SEQ ID NO: 92), ALKDENSQLK (SEQ ID NO: 90), KLADENSQLK (SEQ ID NO: 91), KAKDENSQLR (SEQ ID NO: 98), KLADENSQLR (SEQ ID NO: 99), KLKAENSQLR (SEQ ID NO: 100), KLKDANSQLR (SEQ ID NO: 101), KLKDEASQLR (SEQ ID NO: 102), KLKDENAQLR (SEQ ID NO: 103), KLKDENSQAR (SEQ ID NO: 105), KLKDENSQLA (SEQ ID NO: 106), or a combination thereof.

For example, the amino acid sequence (V) of the peptide can comprise KLKDENSQLK (SEQ ID NO: 3), KLKDDNSQLK (SEQ ID NO: 16), KIKDENSQLK (SEQ ID NO: 92), ALKDENSQLK (SEQ ID NO: 90), KLADENSQLK (SEQ ID NO: 91), KAKDENSQLR (SEQ ID NO: 98), KLKAENSQLR (SEQ ID NO: 100), KLKDENAQLR (SEQ ID NO: 103), KLKDENSQLA (SEQ ID NO: 106), or a combination thereof.

The amino acid sequence (V) of the peptide can comprise KLKDENSQLK (SEQ ID NO: 3).

The amino acid sequence (V) of the peptide can consist of KLKDENSQLK (SEQ ID NO: 3), KLKDENSQL (SEQ ID NO: 119), KLKDENSQ (SEQ ID NO: 120), KLKDDNSQLK (SEQ ID NO: 16), KLKDENAQLK (SEQ ID NO: 18), KLKEENNQLK (SEQ ID NO: 20), KLKEENTQLK (SEQ ID NO: 21), KLKEENSQLR (SEQ ID NO: 22), KLKNENKQLK (SEQ ID NO: 27), KLKNENRQLK (SEQ ID NO: 28), KLKVENGQLK (SEQ ID NO: 32), KVKDENSQLK (SEQ ID NO: 36), KLKDEQEKLK (SEQ ID NO: 39), KLKDENSQLK (SEQ ID NO: 40), KLKNENRQLK (SEQ ID NO: 42), KLEDEQNSQIK (SEQ ID NO: 45), KLKDETSKLK (SEQ ID NO: 46), KLRDENSQLK (SEQ ID NO: 47), KLKQENTQLK (SEQ ID NO: 48), KLQEENHQL (SEQ ID NO: 49), KLKDDEVAQL (SEQ ID NO: 51), KLVEETKQL (SEQ ID NO: 52), LKDENSKL (SEQ ID NO: 54), LKNKNSQLK (SEQ ID NO: 55), LKEENSQ (SEQ ID NO: 56), LKGENEQLK (SEQ ID NO: 58), KLKEEITQL (SEQ ID NO: 59), LKDQNSKL (SEQ ID NO: 61), KLKDENTQLK (SEQ ID NO: 94), KLKTENSQLK (SEQ ID NO: 95), KIKDENSQLK (SEQ ID NO: 92), ALKDENSQLK (SEQ ID NO: 90), KLADENSQLK (SEQ ID NO: 91), KAKDENSQLR (SEQ ID NO: 98), KLADENSQLR (SEQ ID NO: 99), KLKAENSQLR (SEQ ID NO: 100), KLKDANSQLR (SEQ ID NO: 101), KLKDEASQLR (SEQ ID NO: 102), KLKDENAQLR (SEQ ID NO: 103), KLKDENSQAR (SEQ ID NO: 105), KLKDENSQLA (SEQ ID NO: 106), KLKDENSQLKS (SEQ ID NO: 121), KLKDENSQLKSE (SEQ ID NO: 122), KLKDENSQLKSEV (SEQ ID NO: 123), or KLKDENSQLKSEVS (SEQ ID NO: 124).

The amino acid sequence (V) of the peptide can consist of KLQEELNKV (SEQ ID NO: 53).

The amino acid sequence (V) of the peptide preferably consists of KLKDENSQLK (SEQ ID NO: 3), KLKDENSQL (SEQ ID NO: 119), KLKDENSQ (SEQ ID NO: 120), KLQEELNKV (SEQ ID NO: 53), KLKDDNSQLK (SEQ ID NO: 16), KLKTENSQLK (SEQ ID NO: 95), KIKDENSQLK (SEQ ID NO: 92), KLADENSQLK (SEQ ID NO: 91), KLKDENTQLK (SEQ ID NO: 94), ALKDENSQLK (SEQ ID NO: 90), KAKDENSQLR (SEQ ID NO: 98), KLADENSQLR (SEQ ID NO: 99), KLKAENSQLR (SEQ ID NO: 100), KLKDANSQLR (SEQ ID NO: 1101), KLKDEASQLR (SEQ ID NO: 102), KLKDENAQLR (SEQ ID NO: 103), KLKDENSQAR (SEQ ID NO: 105), or KLKDENSQLA (SEQ ID NO: 106).

For example, the amino acid sequence (V) of the peptide can consist of KLKDENSQLK (SEQ ID NO: 3), KLKDENSQL (SEQ ID NO: 119), KLKDENSQ (SEQ ID NO: 120), KLQEELNKV (SEQ ID NO: 53), KLKDDNSQLK (SEQ ID NO: 16), KLKTENSQLK (SEQ ID NO: 95), KIKDENSQLK (SEQ ID NO: 92), KLADENSQLK (SEQ ID NO: 91), ALKDENSQLK (SEQ ID NO: 90), KAKDENSQLR (SEQ ID NO: 98), KLKAENSQLR (SEQ ID NO: 100), KLKDENAQLR (SEQ ID NO: 103), or KLKDENSQLA (SEQ ID NO: 106).

As another example, the amino acid sequence (V) of the peptide can consist of KLKDENSQLK (SEQ ID NO: 3), KLKDDNSQLK (SEQ ID NO: 16), KLKTENSQLK (SEQ ID NO: 95), KIKDENSQLK (SEQ ID NO: 92), KLADENSQLK (SEQ ID NO: 91), KLKDENTQLK (SEQ ID NO:

94), ALKDENSQLK (SEQ ID NO: 90), KAKDENSQLR (SEQ ID NO: 98), KLADENSQLR (SEQ ID NO: 99), KLKAENSQLR (SEQ ID NO: 100), KLKDANSQLR (SEQ ID NO: 101). KLKDEASQLR (SEQ ID NO: 102), KLKDENAQLR (SEQ ID NO: 103), KLKDENSQAR (SEQ ID NO: 105), or KLKDENSQLA (SEQ ID NO: 106).

The amino acid sequence (V) of the peptide more preferably consists of KLKDENSQLK (SEQ ID NO: 3), KLKDDNSQLK (SEQ ID NO: 16), KLKTENSQLK (SEQ ID NO: 95), KIKDENSQLK (SEQ ID NO: 92), KLADENSQLK (SEQ ID NO: 91), ALKDENSQLK (SEQ ID NO: 90), KAKDENSQLR (SEQ H) NO: 98), KLKAENSQLR (SEQ ID NO: 100), KLKDENAQLR (SEQ ID NO: 103), or KLKDENSQLA (SEQ ID NO: 106).

For example, the amino acid sequence (V) of the peptide can consist of KLKDENSQLK (SEQ ID NO: 3), KLKDDNSQLK (SEQ ID NO: 16), KLKTENSQLK (SEQ ID NO: 95), KIKDENSQLK (SEQ ID NO: 92), or KLADENSQLK (SEQ ID NO: 91).

The amino acid sequence (V) of the peptide can consist of KLKDDNSQLK (SEQ ID NO: 16), KLKTENSQLK (SEQ ID NO: 95), or KIKDENSQLK (SEQ ID NO: 92).

The amino acid sequence (V) of the peptide can consist of KLKDENSQLK (SEQ ID NO: 3), KLKDENTQLK (SEQ ID NO: 94), KLKDDNSQLK (SEQ ID NO: 16), KIKDENSQLK (SEQ ID NO: 92), ALKDENSQLK (SEQ ID NO: 90), KLADENSQLK (SEQ ID NO: 91), KAKDENSQLR (SEQ ID NO: 98), KLADENSQLR (SEQ ID NO: 99), KLKAENSQLR (SEQ ID NO: 100), KLKDANSQLR (SEQ ID NO: 101), KLKDENAQLR (SEQ ID NO: 102), KLKDENAQLR (SEQ ID NO: 103), KLKDENSQAR (SEQ ID NO: 105), or KLKDENSQLA (SEQ ID NO: 106).

For example, the amino acid sequence (V) of the peptide can consist of KLKDENSQLK (SEQ ID NO: 3), KLKDDNSQLK (SEQ ID NO: 16), KIKDENSQLK (SEQ ID NO: 92), ALKDENSQLK (SEQ ID NO: 90), KLADENSQLK (SEQ ID NO: 91), KAKDENSQLR (SEQ ID NO: 98), KLKAENSQLR (SEQ ID NO: 100), KLKDENAQLR (SEQ ID NO: 103), or KLKDENSQLA (SEQ ID NO: 106).

The amino acid sequence (V) of the peptide can consist of KLKDENSQLK (SEQ ID NO: 3).

The amino acid sequence (V) of the peptide optionally does not comprise or consist of KLQEELNKV.

The peptides comprising the sequence (V) can have a length of 14 amino acids, 13 amino acids, 12 amino acids, 11 amino acids, 10 amino acids, 9 amino acids, 8 amino acids, or 7 amino acids.

In any of the pharmaceutical or cosmetic compositions described herein, the composition can comprise any one or more of the peptides described herein and a pharmaceutically or cosmetically acceptable carrier. For example, the pharmaceutical or cosmetic composition can comprise any one or more, any two or more, any three or more, any four or more, or any five or more, of the peptides described herein.

The peptides described herein are administered to a subject (e.g., a mammal) in need thereof, e.g., to induce or potentiate subcutaneous adipocyte recruitment or formation (e.g., to induce subcutaneous adipogenesis).

These peptides can be administered in the "native" form or, if desired, in the form of salts, esters, amides, prodrugs, derivatives, and the like, provided the salt, ester, amide, prodrug or derivative is suitable pharmacologically, i.e., effective in the present method(s). Salts, esters, amides, prodrugs and other derivatives of the peptides can be prepared using standard procedures known to those skilled in the art of synthetic organic chemistry and described, for example, by March (1992) *Advanced Organic Chemistry; Reactions, Mechanisms and Structure,* 4th Ed. N.Y. Wiley-Interscience. Methods of formulating such derivatives are known to those of skill in the art. For example, the disulfide salts of a number of delivery agents are described in PCT Publication WO 2000/059863. Similarly, acid salts of therapeutic peptides, peptoids, or other mimetics, and can be prepared from the free base using conventional methodology that typically involves reaction with a suitable acid. Generally, the base form of the peptide is dissolved in a polar organic solvent such as methanol or ethanol and the acid is added thereto. The resulting salt either precipitates or can be brought out of solution by addition of a less polar solvent. Suitable acids for preparing acid addition salts include, but are not limited to, both organic acids, e.g., acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, or salicylic acid, as well as inorganic acids, e.g., hydrochloric acid, hydrobromic acid, sulfuric acid, nitric acid, or phosphoric acid. An acid addition salt can be reconverted to the free base by treatment with a suitable base. Certain particularly preferred acid addition salts of the peptides described herein include halide salts, such as may be prepared using hydrochloric or hydrobromic acids. Conversely, preparation of basic salts of the peptides s described herein are prepared in a similar manner using a pharmaceutically acceptable base such as sodium hydroxide, potassium hydroxide, ammonium hydroxide, calcium hydroxide, or trimethylamine. Basic salts include alkali metal salts, e.g., the sodium salt, and copper salts.

For the preparation of salt forms of a peptide, the pKa of the counterion is preferably at least about 2 pH lower than the pKa of the agent. Similarly, for the preparation of salt forms of acidic agent, the pKa of the counterion is preferably at least about 2 pH greater than the pKa of the agent. This permits the counterion to bring the solution's pH to a level lower than the $pH_{max}$ to reach the salt plateau, at which the solubility of salt prevails over the solubility of free acid or base. The generalized rule of difference in pKa units of the ionizable group in the active pharmaceutical ingredient (API) and in the acid or base is meant to make the proton transfer energetically favorable. When the pKa of the API and counterion are not significantly different, a solid complex may form but may rapidly disproportionate (i.e., break down into the individual entities of peptide and counterion) in an aqueous environment.

Typically, the counterion is a pharmaceutically acceptable counterion. Suitable anionic salt forms include, but are not limited to, acetate, benzoate, benzylate, bitartrate, bromide, carbonate, chloride, citrate, edetate, edisylate, estolate, fumarate, gluceptate, gluconate, hydrobromide, hydrochloride, iodide, lactate, lactobionate, malate, maleate, mandelate, mesylate, methyl bromide, methyl sulfate, mucate, napsylate, nitrate, pamoate (embonate), phosphate and diphosphate, salicylate and disalicylate, stearate, succinate, sulfate, tartrate, tosylate, triethiodide, valerate, and the like, while suitable cationic salt forms include, but are not limited to aluminum, benzathine, calcium, ethylene diamine, lysine, magnesium, meglumine, potassium, procaine, sodium, tromethamine, zinc, and the like.

Preparation of peptide esters typically involves functionalization of hydroxyl and/or carboxyl groups that are present within the molecular structure of the peptide. For example, the esters are typically acyl-substituted derivatives of free alcohol groups, i.e., moieties that are derived from carboxylic acids of the formula RCOOH where R is alkyl, and preferably is lower alkyl. Esters can be reconverted to the free acids, if desired, by using conventional hydrogenolysis or hydrolysis procedures.

Amides of the peptides can also be prepared using techniques known to those skilled in the art. For example, amides can be prepared from esters, using suitable amine reactants, or they can be prepared from an anhydride or an acid chloride by reaction with ammonia or a lower alkyl amine.

The peptides can be formulated for subcutaneous, parenteral, topical, oral, nasal (or otherwise inhaled), rectal, or local administration, such as by aerosol or transdermally. The compositions can be administered in a variety of unit dosage forms depending upon the method of administration. Suitable unit dosage forms, include, but are not limited to powders, tablets, pills, capsules, lozenges, suppositories, patches, nasal sprays, injectables, implantable sustained-release formulations, lipid complexes, etc.

The peptides described herein can also be combined with a pharmaceutically or cosmetically acceptable carrier to form a pharmacological or cosmetic composition. Cosmetic compositions can additionally include a filler (e.g., a hyaluronic filler such as JUVÉDERM® XC, BELOTERO BALANCE, EMERVEL®, RESTYLANE, RADIESSE, a polymethylmethacrylate (PMMA) microspheres and collagen filler such as ARTEFILL®, Calcium Hydroxylapatite (CaHA) microspheres such as RADIESSE®, and the like).

The composition is preferably for topical, subcutaneous, or transdermal administration.

The composition can be a composition for injection.

The composition can further comprise collagen (e.g., a bovine, porcine, or human collagen). The collagen can be a synthetic collagen.

The composition can further comprise an anesthetic (e.g., lidocaine).

The composition can be a skin cream (e.g., a face cream).

Pharmaceutically acceptable carriers and cosmetically acceptable carriers include those approved by a regulatory agency of the Federal or a state government or listed in the U.S. Pharmacopeia or other generally recognized pharmacopeia for use in or on animals, and more particularly humans. A "carrier" refers to, for example, a diluent, adjuvant, excipient, auxiliary agent or vehicle with which one or more of the peptides described herein is administered.

Pharmaceutically acceptable carriers and cosmetically acceptable carriers can contain one or more physiologically acceptable compounds that act, for example, to stabilize the composition or to increase or decrease the absorption of the peptide. Physiologically acceptable compounds can include, for example, carbohydrates, such as glucose, sucrose, or dextrans, antioxidants, such as ascorbic acid or glutathione, chelating agents, low molecular weight proteins, protection and uptake enhancers such as lipids, compounds that reduce the clearance or hydrolysis of the peptides, or other excipients, stabilizers and/or buffers.

Other pharmaceutically acceptable compounds, particularly of use in the preparation of tablets, capsules, gel caps, and the like include, but are not limited to binders, diluent/fillers, disentegrants, lubricants, and suspending agents.

To manufacture an oral dosage form (e.g., a tablet), an excipient (e.g., lactose, sucrose, starch, mannitol, etc.), an optional disintegrator (e.g. calcium carbonate, carboxymethylcellulose calcium, sodium starch glycollate, crospovidone etc.), a binder (e.g. alpha-starch, gum arabic, microcrystalline cellulose, carboxymethylcellulose, polyvinylpyrrolidone, hydroxypropylcellulose, cyclodextrin, etc.), and an optional lubricant (e.g., talc, magnesium stearate, polyethylene glycol 6000, etc.), for instance, are added to the peptide and the resulting composition is compressed. Where necessary, the compressed product is coated using known methods for masking taste or for enteric dissolution or sustained release. Suitable coating materials include, but are not limited to ethyl-cellulose, hydroxymethylcellulose, polyoxyethylene glycol, cellulose acetate phthalate, hydroxypropylmethylcellulose phthalate, and EUDRAGIT (Rohm & Haas, Germany; methacrylic-acrylic copolymer).

Other physiologically acceptable compounds that can be formulated with the peptides include wetting agents, emulsifying agents, dispersing agents or preservatives that are particularly useful for preventing the growth or action of microorganisms. Various preservatives are well known and include, for example, phenol and ascorbic acid. One skilled in the art would appreciate that the choice of pharmaceutically acceptable carrier depends, for example, on the route of administration of the peptide and on the particular physiochemical characteristics of the peptide.

Preferably, the excipients are sterile and generally free of contaminants. These compositions can be sterilized by conventional, well-known sterilization techniques. For various oral dosage form excipients, such as tablets and capsules, sterility is not required; the USP/NF standard is usually sufficient.

Nanoemulsion Formulations

The peptides described herein can be formulated in a nanoemulsion. Nanoemulsions include, but are not limited to, oil-in-water (O/W) nanoemulsions, and water-in-oil (W/O) nanoemulsions. Nanoemulsions can be defined as emulsions with mean droplet diameters ranging from about 20 to about 1000 nm. Usually, the average droplet size is between about 20 nm or 50 nm and about 500 nm. The terms sub-micron emulsion (SME) and mini-emulsion are used as synonyms.

Illustrative oil-in-water O/W nanoemulsions include, but are not limited to: (1) surfactant micelles, which are micelles composed of small molecules, surfactants or detergents (e.g., SDS/PBS/2-propanol) which are suitable for predominantly hydrophobic peptides; (2) polymer micelles, which are micelles composed of polymer, copolymer, or block copolymer surfactants (e.g., Pluronic L64/PBS/2-propanol) which are suitable for predominantly hydrophobic peptides; (3) blended micelles, which are micelles in which there is more than one surfactant component or in which one of the liquid phases (generally an alcohol (e.g., ethanol) or fatty acid compound) participates in the formation of the micelle (e.g., octanoic acid/PBS/EtOH) which are suitable for predominantly hydrophobic peptides; (4) integral peptide micelles, which are blended micelles in which the peptide serves as an auxiliary surfactant, forming an integral part of the micelle (e.g., amphipathic peptide/PBS/mineral oil) which are suitable for amphipathic peptides; and (5) pickering (solid phase) emulsions, which are emulsions in which the peptides are associated with the exterior of a solid nanoparticle (e.g., polystyrene nanoparticles/PBS/no oil phase) which are suitable for amphipathic peptides.

Illustrative water-in-oil (W/O) nanoemulsions include, but are not limited to: (1) surfactant micelles, which are micelles composed of small molecules surfactants or detergents (e.g., dioctyl sulfosuccinate/PBS/2-propanol, isopropylmyristate/PBS/2-propanol, etc.) which are suitable for predominantly hydrophilic peptides; (2) polymer micelles, which are micelles composed of polymer, copolymer, or block copolymer surfactants (e.g., PLURONIC® L121/

PBS/2-propanol), which are suitable for predominantly hydrophilic peptides; (3) blended micelles, which are micelles in which there is more than one surfactant component or in which one of the liquid phases (generally an alcohol (e.g., ethanol) or fatty acid compound) participates in the formation of the micelle (e.g., capric/caprylic diglyceride/PBS/EtOH) which are suitable for predominantly hydrophilic peptides; (4) integral peptide micelles, which are blended micelles in which the peptide serves as an auxiliary surfactant, forming an integral part of the micelle (e.g., amphipathic peptide/PBS/polypropylene glycol) which are suitable for amphipathic peptides; and (5) pickering (solid phase) emulsions, which are emulsions in which the peptides are associated with the exterior of a solid nanoparticle (e.g., chitosan nanoparticles/no aqueous phase/mineral oil) which are suitable for amphipathic peptides.

As indicated above, the nanoemulsions can comprise one or more surfactants or detergents. For example, the surfactant can be a non-anionic detergent (e.g., a polysorbate surfactant or a polyoxyethylene ether). Surfactants that find use in the present invention include, but are not limited to, surfactants such as the TWEEN®, TRITON®, and TYLOXAPOL® families of compounds. Preferably, the surfactant is a polysorbate surfactant (e.g., TWEEN 20®, TWEEN 40®, TWEEN 60®, and TWEEN 80®), a phenoxypolyethoxyethanol (e.g., TRITON® X-100, X-301, X-165, X-102, and X-200, and TYLOXAPOL®), or sodium dodecyl sulfate.

The nanoemulsion can further comprise an emulsifying agent to aid in the formation of the emulsion. Emulsifying agents include compounds that aggregate at the oil/water interface to form a kind of continuous membrane that prevents direct contact between two adjacent droplets. Some oil-in-water emulsion compositions can readily be diluted with water to a desired concentration without impairing their anti-pathogenic properties.

In addition to discrete oil droplets dispersed in an aqueous phase, oil-in-water emulsions can also contain other lipid structures, such as small lipid vesicles (e.g., lipid spheres that often consist of several substantially concentric lipid bilayers separated from each other by layers of aqueous phase), micelles (e.g., amphiphilic molecules in small clusters of 50-200 molecules arranged so that the polar head groups face outward toward the aqueous phase and the apolar tails are sequestered inward away from the aqueous phase), or lamellar phases (lipid dispersions in which each particle consists of parallel amphiphilic bilayers separated by thin films of water). These lipid structures are formed as a result of hydrophobic forces that drive apolar residues (e.g., long hydrocarbon chains) away from water. The lipid preparations can generally be described as surfactant lipid preparations (SLPs). SLPs are minimally toxic to mucous membranes and are believed to be metabolized within the small intestine (see e.g., Hamouda et al., (1998) *J. Infect. Disease* 180: 1939).

The emulsion can comprise a discontinuous oil phase distributed in an aqueous phase, a first component comprising an alcohol (e.g., ethanol) and/or glycerol, and a second component comprising a surfactant or a halogen-containing compound. The aqueous phase can comprise any type of aqueous phase including, but not limited to, water (e.g., deionized water, distilled water, water-for-injection, tap water) and solutions (e.g., phosphate buffered saline solution, or other buffer systems). The oil phase can comprise any type of oil including, but not limited to, plant oils (e.g., soybean oil, avocado oil, flaxseed oil, coconut oil, cottonseed oil, squalene oil, olive oil, canola oil, corn oil, rapeseed oil, safflower oil, and sunflower oil), animal oils (e.g., fish oil), flavor oil, water insoluble vitamins, or mineral oil. Generally, the oil phase comprises about 30 to about 90 volume % of the oil-in-water emulsion (i.e., constitutes 30-90% of the total volume of the final emulsion), more preferably from about 50 to about 80 volume % of the emulsion.

The emulsion can also include a halogen-containing compound such as a chloride salt (e.g., NaCl, KCl, etc.), a cetylpyridinium halide, a cetyltrimethylammonium halide, a cetyldimethylethylammonium halide, a cetyldimethylbenzylammonium halide, a cetyltributylphosphonium halide, a dodecyltrimethylammonium halide, a tetradecyltrimethylammonium halide, cetylpyridinium chloride, cetyltrimethylammonium chloride, cetylbenzyldimethylammonium chloride, cetylpyridinium bromide, cetyltrimethylammonium bromide, cetyldimethylethylammonium bromide, cetyltributylphosphonium bromide, dodecyltrimethylammonium bromide, or tetradecyltrimethylammonium bromide.

The emulsion can also include a quaternary ammonium compound such as N-alkyldimethyl benzyl ammonium saccharinate; 1,3,5-Triazine-1,3,5(2H,4H,6H)-triethanol; 1-Decanaminium, N-decyl-N,N-dimethyl-, chloride (or) Didecyl dimethyl ammonium chloride; 2-(2-(p-(Diisobuyl)cresosxy) ethoxy)ethyl dimethyl benzyl ammonium chloride; 2-(2-(p-(Diisobutyl)phenoxy)ethoxy)ethyl dimethyl benzyl ammonium chloride; alkyl-1- or 3-benzyl-1-(2-hydroxethyl)-2-imidazolinium chloride; alkyl bis(2-hydroxyethyl)benzyl ammonium chloride; alkyl demethyl benzyl ammonium chloride; alkyl dimethyl 3,4-dichlorobenzyl ammonium chloride (100% C12); alkyl dimethyl 3,4-dichlorobenzyl ammonium chloride (50% C14, 40% C12, 10% C16); alkyl dimethyl 3,4-dichlorobenzyl ammonium chloride (55% C14, 23% C12, 20% C16); alkyl dimethyl benzyl ammonium chloride; alkyl dimethyl benzyl ammonium chloride (100% C14); alkyl dimethyl benzyl ammonium chloride (100% C16); alkyl dimethyl benzyl ammonium chloride (41% C14, 28% C12); alkyl dimethyl benzyl ammonium chloride (47% C12, 18% C14); alkyl dimethyl benzyl ammonium chloride (55% C16, 20% C14); alkyl dimethyl benzyl ammonium chloride (58% C14, 28% C16); alkyl dimethyl benzyl ammonium chloride (60% C14, 25% C12); alkyl dimethyl benzyl ammonium chloride (61% C11, 23% C14); alkyl dimethyl benzyl ammonium chloride (61% C12, 23% C14); alkyl dimethyl benzyl ammonium chloride (65% C12, 25% C14); alkyl dimethyl benzyl ammonium chloride (67% C12, 24% C14); alkyl dimethyl benzyl ammonium chloride (67% C12, 25% C14); alkyl dimethyl benzyl ammonium chloride (90% C14, 5% C12); alkyl dimethyl benzyl ammonium chloride (93% C14, 4% C12); alkyl dimethyl benzyl ammonium chloride (95% C16, 5% C18); alkyl dimethyl benzyl ammonium chloride (and) didecyl dimethyl ammonium chloride; alkyl dimethyl benzyl ammonium chloride (as in fatty acids); alkyl dimethyl benzyl ammonium chloride (C12-C16); alkyl dimethyl benzyl ammonium chloride (C12-C18); alkyl dimethyl benzyl and dialkyl dimethyl ammonium chloride; alkyl dimethyl dimethybenzyl ammonium chloride; alkyl dimethyl ethyl ammonium bromide (90% C14, 5% C16, 5% C12); alkyl dimethyl ethyl ammonium bromide (mixed alkyl and alkenyl groups as in the fatty acids of soybean oil); alkyl dimethyl ethylbenzyl ammonium chloride; alkyl dimethyl ethylbenzyl ammonium chloride (60% C14); alkyl dimethyl isoproylbenzyl ammonium chloride (50% C12, 30% C14, 17% C16, 3% C18); alkyl trimethyl ammonium chloride (58% C18, 40% C16, 1% C14, 1% C12); alkyl trimethyl ammonium chloride (90% C18, 10% C16); alkyldimethyl (ethylbenzyl) ammonium chloride (C12-18); Di-(C8-10)- alkyl dimethyl ammonium chlorides; dialkyl dimethyl ammonium chloride; dialkyl dimethyl ammonium chloride; dialkyl dimethyl ammonium chloride; dialkyl methyl benzyl ammonium chloride; didecyl dimethyl ammonium chloride; diisodecyl dimethyl ammonium chloride; dioctyl dimethyl ammonium chloride; dodecyl bis(2-hydroxyethyl) octyl hydrogen ammonium chloride; dodecyl dimethyl benzyl ammonium chloride; dodecylcarbamoyl methyl dimethyl benzyl ammonium chloride; heptadecyl hydroxyethylimidazolinium chloride; hexahydro-1,3,5-tris(2-hydroxyethyl)-s-triazine; myristalkonium chloride and/or quaternium-14; N,N-dimethyl-2-hydroxypropylammonium chloride polymer; n-alkyl dimethyl benzyl ammonium chloride; n-alkyl dimethyl ethylbenzyl ammonium chloride; n-tetradecyl dimethyl benzyl ammonium chloride monohydrate; octyl decyl dimethyl ammonium chloride; octyl dodecyl dimethyl ammonium chloride; octyphenoxyethoxyethyl dimethyl benzyl ammonium chloride; oxydiethylenebis (alkyl dimethyl ammonium chloride); dicoco alkyldimethyl, chloride; trimethoxysily propyl dimethyl octadecyl ammonium chloride; trimethoxysilyl quats, trimethyl dodecylbenzyl ammonium chloride; n-dodecyl dimethyl ethylbenzyl ammonium chloride; n-hexadecyl dimethyl benzyl ammonium chloride; n-tetradecyl dimethyl benzyl ammonium chloride; n-tetradecyl dimethyl ethylbenzyl ammonium chloride; or n-octadecyl dimethyl benzyl ammonium chloride.

Nanoemulsion formulations and methods of making such are well known to those of skill in the art and described for example in U.S. Pat. Nos. 7,476,393, 7,468,402, 7,314,624, 6,998,426, 6,902,737, 6,689,371, 6,541,018, 6,464,990, 6,461,625, 6,419,946, 6,413,527, 6,375,960, 6,335,022, 6,274,150, 6,120,778, 6,039,936, 5,925,341, 5,753,241, 5,698,219, and 5,152,923 and in Fanun et al. (2009) *Microemulsions: Properties and Applications* (*Surfactant Science*), CRC Press, Boca Raton Fla.

Cosmetic Formulations

One or more of the peptides described herein can be incorporated into formulations for cosmetic use. Such cosmetic formulations can be for topical application and can be formulated as skin creams (e.g., face creams) or body lotions, wrinkle-removing creams, or incorporated into cosmetics, sunscreens, or moisturizers.

The peptides can be incorporated into formulations that optionally further include fillers, moisturizers, vitamins (e.g., vitamin E), and/or colorants/tints.

Suitable injectable cosmetic formulations include, but are not limited to, formulations incorporating one or more of the peptides in combination with one or more filler materials. Illustrative materials usable as injectable cosmetic wrinkle fillers include, but are not limited to, temporary (absorbable) fillers such as collagen (e.g., synthetic collagen, bovine collagen, porcine collagen, human collagen, etc.), hyaluronic acid gel, calcium hydroxylapatite (typically implanted in the form of a gel), or poly-L-lactic acid (PLLA). The peptides can also be incorporated into injectable cosmetic formulations containing permanent (non-absorbable) fillers. Illustrative "permanent" fillers include, but are not limited to, polymethylmethacrylate beads (PMMA microspheres).

The peptides described herein can be incorporated into or administered in conjunction with commercial dermal fillers (e.g., RADIESSE® volumizing filler (about 30% by volume calcium hydroxylapatite (CaHA) microspheres (diameter of 25 μm to 45 μm) suspended in a sodium carboxymethylcellulose gel carrier)), JUVEDERM® injectable gel (a cross-linked hyaluronic acid produced by *Streptococcus equi* bacteria, formulated to a concentration of 24 mg/mL, optionally with 0.3% w/w lidocaine, in a physiologic buffer), RESTYLANE® dermal filler (a gel of 20 mg/mL hyaluronic acid generated by *Streptococcus* species of bacteria, chemically crosslinked with BDDE, and suspended in phosphate buffered saline), SCULPTRA® Aesthetic injectable implant (suspension containing microparticles of poly-L-lactic acid (PLLA), carboxymethylcellulose, non-pyrogenic mannitol and sterile water for injection).

Such injectable formulations can additionally include an anesthetic (e.g., lidocaine or an analog thereof).

The injectable formulations are substantially sterile or sterile and/or meet regulatory agency guidelines for subcutaneous injectable fillers.

Dose/Administration

The peptides described herein can be administered to a subject using any route known in the art, including e.g., by injection (e.g., intravenous, intraperitoneal, subcutaneous, intramuscular, or intradermal), inhalation, transdermal application, rectal administration, vaginal administration, or oral administration. Preferred routes of administration include subcutaneous, transdermal, or topical application.

An effective amount of the peptides can be administered via local (i.e., non-systemic) administration, such as by peripheral administration which includes, but is not limited to, peripheral intramuscular, intraglandular, and subcutaneous administration.

Administration of the peptides can be in any convenient manner, e.g., by injection, intravenous and arterial stents (including eluting stents), catheter, oral administration, inhalation, transdermal application, rectal administration, and the like.

The peptides can be formulated with a pharmaceutically acceptable carrier, e.g., as described above, prior to administration. Pharmaceutically acceptable carriers are determined in part by the particular composition being administered, as well as by the particular method used to administer the composition. Accordingly, there are a wide variety of suitable formulations for the peptides described herein (see, e.g., *Remington's Pharmaceutical Sciences,* 17th ed., 1989).

The dose administered to a subject, in the context of the methods described herein should be sufficient to effect a beneficial therapeutic response (e.g., increased subcutaneous adipogenesis) in the subject over time. The dose will be determined by the efficacy of the particular vehicle/delivery method employed, the site of administration, the route of administration, and the condition of the subject, as well as the body weight or surface area of the subject to be treated. The size of the dose also will be determined by the existence, nature, and extent of any adverse side-effects that accompany the administration of a particular peptide in a particular subject.

The terms "effective amount" or "amount effective to" or "therapeutically effective amount" refers to an amount sufficient to induce a detectable therapeutic (or cosmetic) response in the subject (e.g. an amount sufficient to induce or to potentiate adipogenesis). In determining the effective amount of peptide to be administered, the attending physician will decide the dosage with which to treat each individual patient, taking into consideration a variety of factors, such as age, body weight, general health, diet, sex, peptide and formulation to be administered, route of administration, the severity of the condition being treated and the response of the subject and any adverse effects (e.g., irritation or allergies). The peptides described herein can also be administered at a rate determined by the $LD_{50}$ of the peptide and/or the therapeutic efficacy/activity of the peptide, and the side-effects of the peptide at various concentrations, as applied to the mass and overall health of the subject.

The dose of peptide can vary widely, and will be selected primarily based on activity of the active ingredient, and body weight in accordance with the particular mode of administration selected and the subject's needs. Concentrations, however, will typically be selected to provide dosages ranging from about 0.1 to about 50 mg/kg/day or more. Typical dosages range from about 1 mg/kg/day to about 50 mg/kg/day, about 2 mg/kg/day to about 30 mg/kg/day, or about 3 mg/kg/day to about 20 mg/kg/day, such as about 3 mg/kg/day to about 3.5 mg/kg/day, preferably from about 3.5 mg/kg/day to about 7.2 mg/kg/day, more preferably from about 7.2 mg/kg/day to about 11.0 mg/kg/day, or most preferably from about 11.0 mg/kg/day to about 15.0 mg/kg/day. Dosages of peptides can range from about 10 mg/kg/day to about 50 mg/kg/day. Alternatively, the dosages can range from about 20 mg to about 50 mg given twice daily. It will be appreciated that such dosages may be varied to optimize a therapeutic and/or cosmetic regimen in a particular subject or group of subjects.

Administration can be accomplished via single or divided doses, e.g., doses administered on a regular basis (e.g., once daily or twice daily) for a period of time (e.g., 2, 3, 4, 5, or 6 days or 1-3 weeks or more).

The peptides described herein can be administered systemically (e.g., orally, or as an injectable) in accordance with standard methods well known to those of skill in the art. Peptides can be administered to the oral cavity in various forms such as lozenges, aerosol sprays, mouthwash, coated swabs, and the like. Various buccal, and sublingual formulations are also contemplated. The peptides can be administered in a depot formulation when formulated as an injectable to provide treatment over a period of time.

The peptides can be administered topically, e.g., to the skin surface, to a topical lesion or wound, to a surgical site, and the like.

The peptides can also be delivered through the skin using conventional transdermal drug delivery systems, i.e., transdermal "patches" wherein the peptides are typically contained within a laminated structure that serves as a drug delivery device to be affixed to the skin. In such a structure, the drug composition is typically contained in a layer, or "reservoir," underlying an upper backing layer. The term "reservoir" in this context refers to a quantity of active ingredient that is ultimately available for delivery to the surface of the skin. Thus, for example, the "reservoir" may include the active ingredient peptide in an adhesive on a backing layer of the patch, or in any of a variety of different matrix formulations known to those of skill in the art. The patch may contain a single reservoir, or it may contain multiple reservoirs. For example, the reservoir can comprise a polymeric matrix of a pharmaceutically acceptable contact adhesive material that serves to affix the system to the skin during drug delivery. Examples of suitable skin contact adhesive materials include, but are not limited to, polyethylenes, polysiloxanes, polyisobutylenes, polyacrylates, polyurethanes, and the like. Alternatively, for example, the drug-containing reservoir and skin contact adhesive are present as separate and distinct layers, with the adhesive underlying the reservoir which, in this case, may be either a polymeric matrix as described above, or it may be a liquid or hydrogel reservoir, or may take some other form. The backing layer in these laminates, which serves as the upper surface of the device, preferably functions as a primary structural element of the "patch" and provides the device with much of its flexibility. The material selected for the backing layer is preferably substantially impermeable to the peptides and any other materials that are present.

Other formulations for topical delivery include, but are not limited to, ointments, gels, sprays, fluids, and creams. Ointments are semisolid preparations that are typically based on petrolatum or other petroleum derivatives. As with other carriers or vehicles, an ointment base should be inert, stable, nonirritating and nonsensitizing. Creams containing the selected peptide are typically viscous liquid or semisolid emulsions, often either oil-in-water or water-in-oil. Cream bases are typically water-washable, and contain an oil phase, an emulsifier and an aqueous phase. The oil phase, also sometimes called the "internal" phase, is generally comprised of petrolatum and a fatty alcohol such as cetyl or stearyl alcohol; the aqueous phase usually, although not necessarily, exceeds the oil phase in volume, and generally contains a humectant. The emulsifier in a cream formulation is generally a nonionic, anionic, cationic or amphoteric surfactant. The specific ointment or cream base to be used, as will be appreciated by those skilled in the art, is one that will provide for optimum drug delivery.

One or more peptides described herein can be provided as a "concentrate", e.g., in a storage container (e.g., in a premeasured volume) ready for dilution, or in a soluble capsule ready for addition to a volume of water, alcohol, hydrogen peroxide, or other diluent. For example, the peptides can be lyophilized for later reconstitution.

Uses

The adipogenic peptides (or mimetics thereof) and compositions described herein find use in a number of applications. In particular, the peptides and compositions can be used for any pharmaceutical or cosmetic use benefitting from blocking RHAMM function. For example, enhancing the formation of subcutaneous fat has use in plastic surgery procedures since subcutaneous fat provides plumpness and firmness to skin. Aging skin contains less subcutaneous fat. Therefore administering one or more peptides or compositions described herein to the desired area to promote subcutaneous fat formation results in plumper and more youthful appearing skin. This approach can replace current methods for transplanting adipocytes from other areas of the body (e.g., the thigh or buttocks), a procedure that often exhibits a low success rate.

The peptides and compositions described herein can be administered to selectively enhance subcutaneous adipose tissue (e.g., to enhance subcutaneous adipose tissue without substantially increasing visceral adipose and/or other adipose tissue). In response to administration of the peptides or compositions, adipocyte formation occurs in dermal fibroblasts and volume is added in a selected subcutaneous area in the subject.

The peptides and compositions described herein can be used to reduce scarring or fibrosis. This can be accomplished by administering one or more of the peptides or compositions in an amount sufficient to reduce an area of scarring or fibrosis and/or improve the appearance of a scarred or fibrotic area. The scarring or fibrosis, for example, can be scarring or fibrosis produced by a burn, scarring or fibrosis produced by surgery, scarring or fibrosis produced by acne, scarring or fibrosis produced by a biopsy, or scarring or fibrosis produced by a disease or an injury.

The peptides and compositions described herein can be used, e.g., in various cosmetic procedures, to improve the appearance of skin. This can be accomplished by administering one or more of the peptides or compositions in an amount sufficient to improve the appearance of skin in an area of a subject. Such administering can include subcutaneously administration to a region such as lips, eye lids, cheeks, forehead, chin, neck, and the like. The peptides and compositions can be used in these methods, or others to reduce wrinkles, reduce sagging skin, improve the surface texture of skin, diminish, remove or fill-in wrinkles, remove or diminish age spots, and/or remove dark circles under the eyes. These cosmetic applications are illustrative and not intended to be limiting. In view of the teachings provided herein, other cosmetic applications will be recognized by and available to one of skill in the art.

The peptides and compositions described herein can be used to improve tissue volume in an area of a subject. This can be accomplished by administering one or more of the peptides or compositions described herein in an amount sufficient to increase tissue volume in an area of a subject. For example, the increase of tissue volume can involve firming or augmenting breast tissue and/or firming or augmenting tissue in the buttocks or other regions of the body or face.

The peptides and compositions can also be used to smooth skin in an area of a subject. This can be accomplished by administering one or more of the peptides or compositions described herein in an amount sufficient to smooth skin in the desired area. The smoothing can include smoothing skin scarred by acne, smoothing areas of cellulite, smoothing or reducing stretch marks, and/or smoothing out wrinkles.

The peptides and compositions described herein can be used to recruit stem cells to the formation of subcutaneous fat in a subject. This can be accomplished by administering one or more of the peptides or compositions described herein in an amount sufficient to recruit stem cells to the formation of subcutaneous fat. This has utility, for example, in various reconstructive surgical procedures and the like.

The peptides and compositions described herein can be used to reconstructing tissue in a subject. Such reconstruction can include, for example, breast reconstruction (e.g. after surgery to remove tumors), or face or limb reconstruction (e.g. after car accident or burning). This can be accomplished by administering one or more of the peptides or compositions described herein in an amount to increase the volume of the tissue during or after a tissue reconstruction procedure. The peptides or compositions are optionally used in conjunction with tissue grafting material or other procedures that enhance youthful skin or repair of damaged tissues.

The peptides and compositions can also be used to reduce heel pain in a subject by administering one or more of the peptides or compositions described herein in an amount sufficient to reduce heel pain experienced by the subject when walking. Without being bound by any particular theory, it is believed that the peptides or compositions when administered in a sufficient amount inhibit RHAMM function associated with biological responses including, but not limited to, adipogenesis and anti-fibrosis that lead to reduced heel pain in a treated subject when walking.

The peptides and compositions described herein can be administered for augmentation of subcutaneous fat to improve thermoregulation and/or improve immune function. The subject can be treated with the peptides or compositions to prevent disease or to treat ongoing disease associated with increased organ fat including but not limited to cardiovascular disease, and other obesity associated diseases.

The administration in any of these methods can be local or systemic, and can be by any route described herein, such as topical, subcutaneous, transdermal, oral, nasal, vaginal, and/or rectal administration. Preferably, the peptides and compositions are administered by subcutaneous injection. Alternatively, the peptides and compositions are preferably administered topically in the form of a skin cream such as a face cream, or transdermally via a transdermal patch.

While the uses and methods are described with respect to use in humans, they are also suitable for animal, e.g., veterinary use. Thus certain preferred organisms include, but are not limited to humans, non-human primates, canines, equines, felines, porcines, ungulates, largomorphs, and the like.

Having described the invention in detail, it will be apparent that modifications and variations are possible without departing from the scope of the invention defined in the appended claims.

EXAMPLES

The following non-limiting examples are provided to further illustrate the present invention.

Example 1

Assays to Measure Adipogenesis

The following assays were used to assess adipogenic activity of the peptides in the experiments described in Examples 3 and 4 below and to generate the data shown in FIGS. 3A, 3B, 6A, and 6B.
Assay 1
Reagents: (1) 3-isobutyl-1-methylxanthine (IBMX) solution: 0.5M in DMSO; (2) Insulin Solution: 10 mg/mL recombinant human insulin; (3) Dexamethasone Solution in 10 mM in ethanol; (4) Oil Red O (0.36% in 60% isopropanol).
Preparation of Media:
Adipogenesis Initiation Media: mesenchymal stem cell expansion media/0.5 mM IBMX/1 µM dexamethasone. Mesenchymal stem cell expansion media is commercially available from Millipore. The IBMX Solution was diluted 1:1000 and the Dexamethasone Solution was diluted 1:10,000 in expansion media containing antibiotics and antimycotics. The prepared media was stored at 4° C.

Adipogenesis Progression Media for positive control: mesenchymal stem cell expansion media/10 µg/mL insulin. The Insulin Solution was diluted 1:1000 in the expansion media and stored at 4° C.

Experimental Adipogenesis Progression Media: mesenchymal stem cell expansion media/1-100 µg/mL RHAMM antagonist peptides.

Adipogenesis Maintenance Media: mesenchymal stem cell expansion media containing antibiotics and antimycotics.

Negative Control Media: Dulbecco's Modified Eagle's Medium (DMEM)/10% normal calf serum.
Assay Method:
Pre-adipocyte stem cells including bone marrow mesenchymal stem cells and fibroblasts were propagated using standard tissue culture methods. Cells were trypsinized to remove the cells from the substratum. The trypsin was neutralized and cells were counted using a hemocytometer. Cells were resuspended at 20,000 cells/mL in expansion media. 1 mL of cell suspension was plated per well of 48-well plate, with several wells left empty for blank well (blank control) staining.

Cells were incubated until they reached confluency. When cells were fully confluent, the expansion media was replaced with 0.5 mL of Adipogenesis Initiation Media. For negative controls (no insulin, no peptides), expansion media only was used at this step and for subsequent media changes. For all media changes, media was replaced as gently as possible to avoid disturbing the monolayer.

Cells were incubated in Adipogenesis Initiation Media for 72 hours at 37° C., 5% $CO_2$. 0.5 mL media was then removed from each well, and replaced with 0.5 mL of either positive control or experimental Adipogenesis Progression Media per well. Cells were again incubated for 96 hours at 37° C., 5% $CO_2$, after which time media was replaced every 48 hours with Adipogenesis Maintenance Media (0.5 mL of media was removed from each well and replaced with 0.5 mL Adipogenesis Maintenance Media per well). Media added to empty wells served as blank controls for blank well background staining. Cells were incubated in Adipogenesis Maintenance Medium for at least 96 hours at 37° C., 5% $CO_2$ after which time media was replaced with Adipogenesis Maintenance Medium. Lipid droplets had appeared by the time Adipogenesis Maintenance Medium was initially added and continued to accumulate and increase in size for 7-14 days. Experiments were terminated between seven and fourteen days after the initial addition of Adipogenesis Maintenance Medium.

Quantification of Adipogenesis:

Oil Red O Staining

For quantification of Oil Red O staining, media was removed and cells were washed twice with PBS, using care to gently add the PBS. Cells were then fixed in 4% paraformaldehyde (0.5 mL/well) and incubated for 30 minutes. The fixation solution was then removed and wells were washed two times with 1 mL of phosphate buffered saline (PBS) and once with 1 mL Milli-Q water. 0.25 mL Oil Red O solution was added per well of 48-well plate, including to the wells lacking cells, but containing media. Cells were incubated for 15 minutes at room temperature. The staining solution was then removed and wells were washed two times with 1 mL of Milli-Q water and once with washing solution (63% isopropanol in water).

Adipogenesis was quantified using a spectrophotometer. 0.25 mL Dye Extraction Solution (isopropyl alcohol) was added per well, and the plate was set on an orbital shaker or platform rocker for 30 minutes. Extracted dye was transferred into a cuvette and absorbance was read in a spectrophotometer at visible range for oil red O or transferred to a 96-well plate and quantified in a plate reader at its maximum absorbance of 520 nm.

Blank Well Staining

The stain extracted from wells lacking cells represents non-specific binding of the dye to the plate. The average absorbance value of the blank wells was subtracted from the absorbance of experimental wells to obtain a more accurate measure of cell-specific staining.

Assay 2

Reagents: The Dexamethasone, IBMX, Insulin, and Oil Red O Solutions were the same as described above for assay 1. Indomethacin Solution contained 10 mM indomethacin in methanol.

Preparation of Media:

Adipogenesis Maintenance Media was prepared as described above.

Adipogenesis Induction Media: To prepare 501.5 mL of Adipogenesis Induction Media, 50 μL of the 10 mM stock Dexamethasone Solution, 500 μL of the 0.5 M IBMX stock solution, 500 μL of the 10 mg/ml stock Insulin Solution, 5 ml of a 10 mM stock Indomethacin Solution, and 5 mL of a 100× stock solution of penicillin and streptomycin were added to 490 mL of mesenchymal stem cell expansion media.

Assay Method:

Pre-adipocyte stem cells, bone marrow mesenchymal stem cells or fibroblasts such as dermal reticular and papillary fibroblasts were propagated using standard tissue culture methods. Cells were trypsinized to remove cells from the substratum, the trypsin was neutralized, and cells were counted using a hemocytometer. Cells were resuspended at 20,000 cells/ml in DMEM containing 10% calf serum. 1 mL of cell suspension per well was plated in a 48-well plate, with several wells left empty for blank well (blank control) staining.

Cells were incubated for 2 days overnight and had reached confluency at this point. Media was removed from each well and replaced with 0.5 ml Adipogenesis Induction Media. For negative control (no insulin, no peptide) wells, expansion medium only was used at this step and for subsequent media changes. For all media changes, media was replaced as gently as possible to avoid disturbing the monolayer.

Cells were incubated for 72 hours at 37° C., 5% $CO_2$. Media was removed and replaced with 0.5 ml of Adipogenesis Maintenance Media containing either RHAMM antagonist peptides (experimental group) or insulin (concentration as in the Adipogenesis Induction Media and used as a positive control). Cells were incubated for at least 96 hours in this media at 37° C., 5% $CO_2$. Media was replaced every 48 hours and experiments were terminated between seven and fourteen days after addition of insulin or peptides.

Media was removed and Oil Red O staining was performed as described above for assay 1.

Example 2

Identification and Testing of Adipogenic Peptides

Ablation of RHAMM expression promotes adipogenesis (Tolg et al., 2006, J Cell Biol). As described in PCT Publication No. WO 2014/082042, a RHAMM carboxy-terminal sequence from mouse RHAMM [AA681LDAFEAEKQA LLNEHGATQE QLNKIRDSYA QLLGHQNLKQ KIKHVVKLKD ENSQLKSEVS KLRSQLVKRK QNELRLQGEL DKALGIRHFD PSKAF-CHASK ENFTPLKEGN PNCC$^{aa794}$] (SEQ ID NO: 11) was produced as a recombinant protein, and antibodies were prepared to this protein fragment. It was shown that both this 114 amino acid protein fragment and the antibody promoted adipogenesis using a commercially available mesenchymal stem cell kit.

Figure 2:
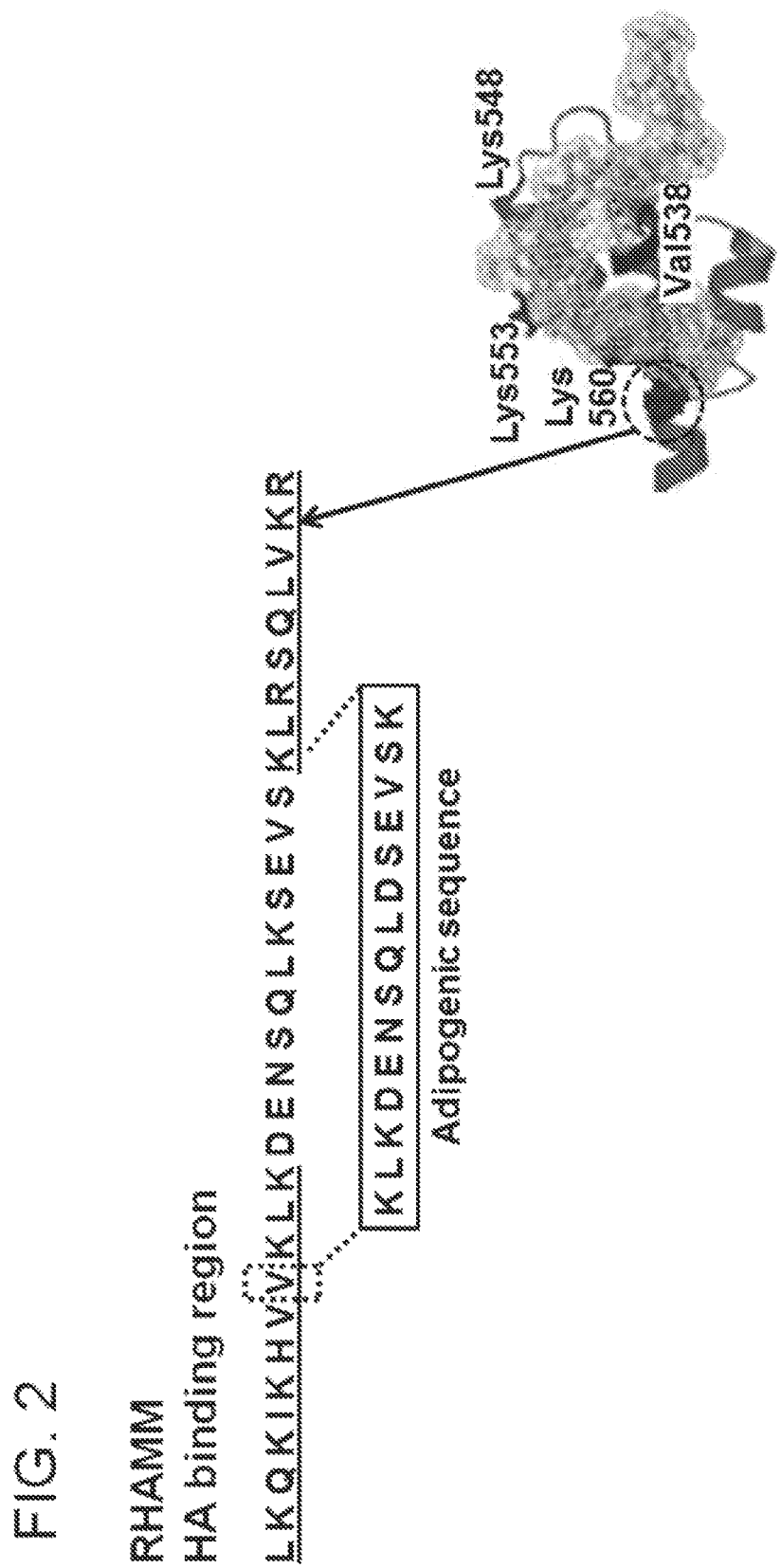
FIG. 2 illustrates the RHAMM HA binding region and the adipogenic subdomain.

It was hypothesized that the fragment and the antibody were blocking RHAMM function by competitive inhibition and by direct binding/blocking of RHAMM, respectively. Using truncation analyses, the size of the peptide was further reduced to 32 amino acids (LKQKIKHVVKLKDENSQLK-SEVSKLRSQLVKR; SEQ ID NO: 12), and it was shown that adipogenic activity is localized to a 15 amino acid peptide (KLKDENSQLKSEVSK; SEQ ID NO: 2, referred to as "peptide B" herein) shown in FIG. 2. This peptide was chemically synthesized to use as a competitive blocker, and antibodies were prepared against this sequence tagged with keyhole lymphocyte hemacyanin (KLH) to directly bind/block RHAMM function. Both types of reagents were found to effectively block RHAMM function and promote adipogenesis in tissue culture and in vivo.

Peptide B, peptide P15-1, and antibody to peptide B were all found to have adipogenic effects in pre-adipocyte stem cells in culture, when injected into the dermis of aged rats, and in two-dimensional cultures of human pre-adipocytes.

It was further found that all of these reagents could replace insulin in their ability to promote adipogenesis in mesenchymal stem cells or papillary fibroblasts. For example, in bone marrow mesenchymal stem cells, a maximum adipogenic effect was obtained at 1-5 µg of peptide B (SEQ ID NO: 2), depending upon the screening assay used.

In vivo, 25-50 µg of peptide B per injection site in a rat dermal skin model of adipogenesis induced significant fat accumulation. Peptide B was also effective in promoting adipogenesis in a nude guinea pig model.

Two approaches were used to identify additional adipogenic peptides and to identify the key adipogenic sequences. The RHAMM sequence that contains adipogenic activity also contains the hyaluronan binding region of this protein. Thus, in the first approach, an unbiased screen was performed to identify hyaluronan-binding peptides using 15-mer random phage libraries. Peptide sequences identified in this screen were sorted for: (a) their alignment to the HA binding region of RHAMM, and (b) their lack of alignment to the HA binding region of CD44. A 15 amino acid hyaluronan binding peptide having the sequence STMMSRSHKTRSHHV (SEQ ID NO: 1, referred to as peptide P15-1 herein), was identified in this manner. Peptide P15-1 promotes adipogenesis in tissue culture and in vivo.

In the second approach, a series of truncations and alanine mutagenesis on peptide B were performed in order to identify the smallest active sequence. Fragments of peptide B were prepared and assayed for adipogenesis. First, fragments corresponding to the two halves of peptide B were prepared (KLKDENS (SEQ ID NO: 8) and SQLKSEVSK (SEQ ID NO: 13)). Only the carboxy-terminal SQLKSEVSK fragment (SEQ ID NO: 13) was found to be adipogenic. This fragment was then further shortened to LKSEVSK (SEQ ID NO: 14) and KSEVSK (SEQ ID NO: 7), both of which were also found to be adipogenic. Thus, the truncation experiments identified a 9-mer (SQLKSEVSK; SEQ ID NO: 13), a 7-mer (LKSEVSK; SEQ ID NO: 14) and a 6-mer (KSEVSK; SEQ ID NO: 7) that exhibited adipogenic activity.

The KSEVSK 6-mer (SEQ ID NO: 7) was found to exhibit adipogenic activity in both assays 1 and 2 (described in Example 1 above), and of the 9-mer, 7-mer, and 6-mer fragments, the KSEVSK 6-mer had the highest specific activity in both assays 1 and 2. The KSEVSK 6-mer (SEQ ID NO: 7) was also tested in vivo and found to induce large fat pads in rat skin. The KSEVSK 6-mer (SEQ ID NO: 7) also exhibited adipogenic activity in human primary cells directly isolated from human subcutaneous fat or dermal tissue.

Peptide P15-1 was also truncated to create an amino-terminal 9-mer having the sequence STMMSRSHK (SEQ ID NO: 15), which was also found to have adipogenic activity. Alignments of peptide P15-1 with the KSEVSK (SEQ ID NO: 7) hexamer using the COBALT and MUSCLE alignment tools revealed that the sequence KSEVSK aligns with the STMMSR portion of peptide P15-1, as shown below:

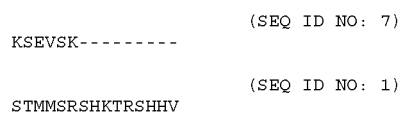

```
                             (SEQ ID NO: 7)
KSEVSK---------

(SEQ ID NO: 1)
STMMSRSHKTRSHHV
```

Based on this alignment, the STMMSR peptide (SEQ ID NO: 10) was expected to have adipogenic activity. A BLAST query of the STMMSR sequence (SEQ ID NO: 10) identified a number of similar sequences found in other proteins linked to both adipogenesis and hyaluronan. Several of these peptides were found to exhibit adipogenic effects in Assays 1 and 2.

As noted above, when fragments corresponding to the two halves of peptide B were prepared (KLKDENS (SEQ ID NO: 8) and SQLKSEVSK (SEQ ID NO: 13)), only the carboxy-terminal SQLKSEVSK fragment was found to be adipogenic. The amino-terminal fragment, KLKDENS (SEQ ID NO: 8), did not exhibit adipogenic activity. It has now unexpectedly been found that a slightly longer amino terminal fragment of peptide B, having the sequence KLKDENSQLK (SEQ ID NO: 3), has adipogenic activity.

It has also unexpectedly been found that a 7-mer fragment derived from the carboxy-terminal end of the P15-1 peptide has adipogenic activity. This 7-mer fragment has the sequence KTRSHHV (SEQ ID NO: 6).

The adipogenic effects of the KLKDENSQLK (SEQ ID NO: 3) and KTRSHHV (SEQ ID NO: 6) peptides and related sequences are described further in the examples below.

Example 3

Adipogenic Activity of KLKDENSQLK and Related Peptides

The 10-mer KLKDENSQLK (SEQ ID NO: 3) fragment derived from the amino-terminal end of peptide B was tested for adipogenic effects in rat mesenchymal stem cells using Assays 1 and 2 described above in Example 1. Assay 1 is an assay that promotes transdifferentiation of fibroblasts into adipocytes, whereas Assay 2 promotes differentiation of multi-potential mesenchymal progenitor cells into adipocytes. Immortalized rat bone marrow mesenchymal stem cells were used for both assays. These cells contain cells of different lineages, including fibroblasts, pre-adipocytes, pre-chondrocytes and pre-osteoblasts. Thus, Assay 1 was used to promote transdifferentiation of fibroblast lineages into adipocytes and Assay 2 was used to promote differentiation of the pre-adipocytes into adipocytes.

As described in Example 1 above, the priming stimulus for Assay 1 includes IBMX (3-isobutyl-1-methylxanthine) and dexamethasone, and then insulin as the final adipogenic stimulus. The priming stimulus for assay 2 includes IBMX, dexamethasone and indomethacin, and then insulin as the final adipogenic stimulus.

Adipogenesis was quantified by Oil Red O staining. The peptide was tested at concentrations of 5 and 50 µg/ml over a period of three weeks. Cells were plated in 48-well culture plates, and the purity of the peptides was >95%. All data are presented as the fold change relative to the negative control (Ctr(−))±standard error. The KSEVSK 6-mer (SEQ ID NO: 7) was used as a positive control. Negative controls did not receive an adipogenic stimulus.

Figure 3B:
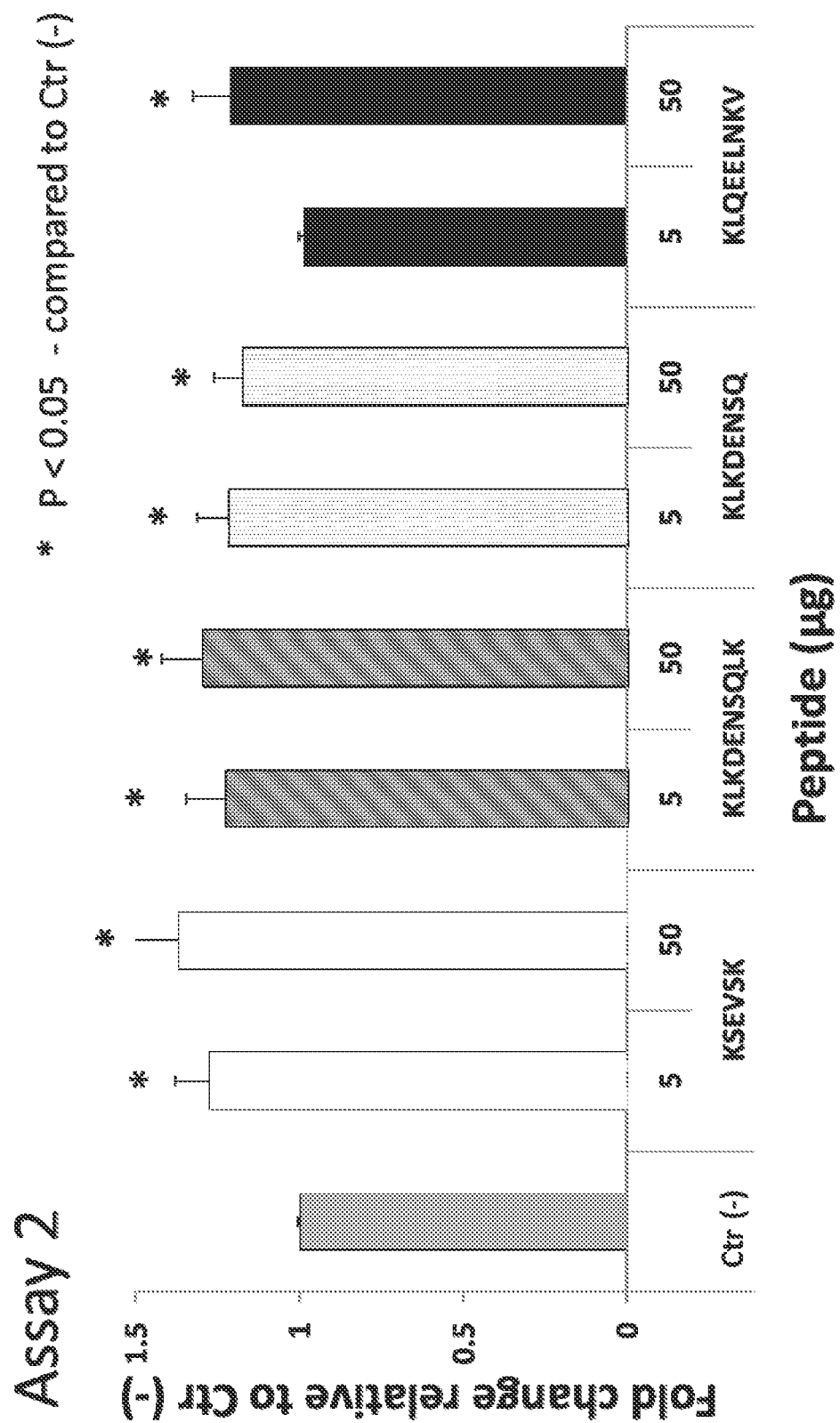

As shown in FIGS. 3A and 3B, KLKDENSQLK (SEQ ID NO: 3) caused a significant increase in adipogenesis as compared to the negative control in both Assay 1 and Assay 2 and at both concentrations tested.

To identify a minimal motif sufficient to impart adipogenic activity to a peptide, the KLKDENSQLK 10-mer (SEQ ID NO: 3) was used to query the unigene data banks (http://www.ncbi.nlm.nih.gov/unigene/) to identify evolutionarily conserved sequences in RHAMM proteins from other organisms. Peptide sequences that were homologous to RHAMM KLKDENSQLK (SEQ ID NO: 3) were identified from chordate to animal phyla. The results of this query are shown below in Table 1.

TABLE 1

Evolutionary conservation of the KLKDENSQLK sequence in RHAMM proteins from various species.

| Sequence | Species | SEQ ID NO. |
|---|---|---|
| KLKDENSQLK | Homo sapiens, Condylura cristata, Myotis davidii, and Gorilla gorilla gorilla | 3 |
| KLKDDNSQLK | Camelus ferus | 16 |
| KLKDENSQLR | Erinaceus euronaeus | 17 |
| KLKDENAQLK | Chrysemys pict bellii and Pelodisus sinensis | 18 |
| KLKDENSNLK | Ovis aries and Bos taunus | 19 |
| KLKEENNQLK | Monodelphis domestica and Sarcophilus harrisii | 20 |
| KLKEENTQLK | Anolis carolinesis and Python bivittatus | 21 |
| KLKEENSQLR | Latimeria chalumnae | 22 |
| KLKTENSELK | Xenopus laevis | 23 |
| KLKIENSELK | Xenopus (Silurana) tropicalis | 24 |
| KLKDENISLK | Haplochromis burtoni, Pundamilia nyererei, and Neolamprologus brichardi | 25 |
| KLKEENTHLK | Columba livia and Falco peregrinus | 26 |
| KLKNENKQLK | Caenorhabditus briggsae | 27 |
| KLKNENIQLK | Alligator mississippiensis | 28 |
| KLKEENLELK | Danio rerio | 29 |
| KLKDENTSLK | Takifugu rubripes | 30 |
| KLKEENFNLK | Lepisosteus oculatus | 31 |
| KLKVENGQLK | Callorhinchus milli | 32 |
| KIKEESVALK | Ciona intestinalis | 33 |
| KTKYLEKTKK | Tribolium castaneum | 34 |

In addition, a BLAST query of the KLKDENSQLK (SEQ ID NO: 3) sequence against the human and other genomes identified a number of similar sequences found in other proteins including those linked to adipogenesis and/or hyaluronan and/or sugar metabolism and/or synthesis. The sequences that were similar to KLKDENSQLK (SEQ ID NO: 3) in other non-RHAMM proteins were identified using the protein BLAST function on NCBI (http://blast.ncbi.nlm.nih.gov/Blast.cgi). These sequences are shown below in Table 2.

TABLE 2

KLKDENSQLK-like sequences identified by BLAST searching.

| Sequence | Source Protein(s) | SEQ ID NO. |
|---|---|---|
| KLKDENSQLR | unnamed protein product (Homo sapiens) | 17 |
| KLKDENSALK | unnamed protein product (Tetraodon migroviridis) | 35 |
| KLKTENSELK | microtubule associated protein (Xenpus laevis)* | 23 |
| KVKDENSQLK | hypothetical protein (Bacillus timonensis) | 36 |
| KLKEENAALK | hypothetical protein (Desulfovibrio piezophilus) | 37 |
| KLKDENDALK | Hypothetical protein AURDEDRAFT_181694 (Auricularia delicata) | 38 |
| KLKDEQEKLK | phosducin protein (Echinococcus multilocularus)* | 39 |
| KLKDENEQLK | hypothetical protein (Aminobacterium mobiler) | 40 |

TABLE 2-continued

KLKDENSQLK-like sequences identified by BLAST searching.

| Sequence | Source Protein(s) | SEQ ID NO. |
|---|---|---|
| KLKDENSRLK | hypothetical protein IMG5_020530 (*Ichthyophthirius multifiliis*) | 41 |
| KLKNENRQLK | uncharacterized protein LOC100213125 (*Hydra vulgaris*) | 42 |
| KLRDENSTLK | kinesin (*Angomonas deanei*)* | 43 |
| KLKIQNLEGE | hypothetical protein TTHERM_0016330 (*Tetrahymena thermophila*) | 44 |
| KLKDENAQLK | hypothetical protein (*Trichonanas vaginalis*) | 18 |
| KLEDEQNSQIK† | hypothetical protein (*Paramecium tetraurelia*) | 45 |
| KLKDETSKLK | hypothetical protein SELMODRAFT_410667 (*Selaginella moellendorffii*) | 46 |
| KLRDENSQLK | DNA-directed RNA polymerase, beta subunit (*Alloprevotella rava*)* | 47 |
| KLKQENTQLK | rab11 family-interacting protein (*Homo sapiens*)* | 48 |
| KLQEENHQL- | RUN and FYVE domain-containing protein 2 isoform X6 (*Scleropages formosus*) | 49 |
| KLKAENDRLK | neuron navigator 2 isoform X9 (*Homo sapiens*) | 50 |
| KLKDDEVAQL† | L-lactate dehydrogenase B chain (*Tupaia chinensio*)* | 51 |
| KLVEETKQL- | unconventional myosin-Va isoform X5 (*Colobus angolensis palliates*)* | 57 |
| KLQEELNKV- | RHAMM (*Ovis aries*)* | 53 |
| -LKDENSKL- | serologically defined colon cancer antigen 3 isoform (*Heterocephalus glaber*)* | 54 |
| -LKNKNSQLK | acidic mammalian chitinase isoform c precursor (*Myotis brandtii*)** | 55 |
| -LKEENSQ-- | centrosomal protein of 112 kDa isoform b (*Homo sapiens*)* | 56 |
| -LKDEKSNLK | RNA polymerase-associated protein CTR9 homolog (*Pan troglodytes*) | 57 |
| -LKGENEQLK | coiled-coil domain-containing protein 152 (*Macaca fasicularis*)* | 58 |
| LLKEEITQL- | kinesin-like protein KIF20B isoform 2 (*Loxodonta africana*) | 59 |
| -LKAENSHL- | adenomatous polyposis coli protein 2 isoform X5 (*Homo sapiens*)* | 60 |
| -LKDQNSKL- | Golgin subfamily B member 1 isoform 4 (*Homo sapiens*)* | 61 |

*Sequence found in protein(s) implicated in adipogenesis
**Sequence found in protein(s) implicated in HA and/or sugar metabolism and/or synthesis
†The sequences KLEDEQNSQIK (SEQ. ID NO: 45) and KLKDDEVAQL- (SEQ ID NO: 51) have insertions, which are shown in bold text and underlined.

Using the same methods as described above for KLKDENSQLK (SEQ ID NO: 3), a further truncated version of KLKDENSQLK, KLKDENSQ (SEQ ID NO: 9) was also tested for adipogenic activity, as was one of the sequences identified in the BLAST query, KLQEELNKV (SEQ ID NO: 53). As shown in FIGS. 3A and 3B, the KLKDENSQ 8-mer (SEQ ID NO: 9) had a significant adipogenic effect as compared to the negative control in both Assay 1 and Assay 2, and at both concentrations tested (5 and 50 μg/ml). The adipogenic effects of the 10-mer KLKDENSQLK (SEQ ID NO: 3) and the 8-mer KLKDENSQ (SEQ ID NO: 9) were surprising, since, as noted above, the 7-mer KLKDENS (SEQ ID NO: 8) had previously been found to lack adipogenic activity.

Furthermore, as shown in FIGS. 3A and 3B, KLQEELNKV (SEQ ID NO: 53) also significantly increased adipogenesis as compared to the negative control in both Assays 1 and 2. In Assay 1, this was seen at both concentrations of peptide tested, while in assay 2, the effect was only observed when a concentration of 50 µg/ml was used.

The sequences in Tables 1 and 2 were aligned with one another and with the KLKDENSQLK (SEQ ID NO: 3) sequence, and in combination with the data shown in FIGS. 3A and 3B as well as the data described in Examples 6 and 8 below and shown in FIGS. 8, 9, and 12, were used to generate the motifs described herein.

The KLKDENSQLK (SEQ ID NO: 3) peptide, peptide B (KLKDENSQLKSEVSK, SEQ ID NO: 2), and KSEVSK (SEQ ID NO: 7) are present in a complicated functional region of RHAMM, depicted in FIG. 4. In the sequence shown in FIG. 4 (SEQ ID NO: 4), the region underlined with a dotted underline is an ERK1 docking site (D domain), while the residues indicated in large font are required for HA binding. The region underlined with a solid single underline is the HA binding region, as determined by point mutation and NMR. The bolded leucine residues form a leucine zipper that may be required for association of RHAMM with microtubules and/or could promote RHAMM dimerization or partnering with other proteins that contain a leucine zipper. The double underlined sequence was identified in a BLAST search, but is also present in human RHAMM downstream of the complicated functional region.

Figure 5:
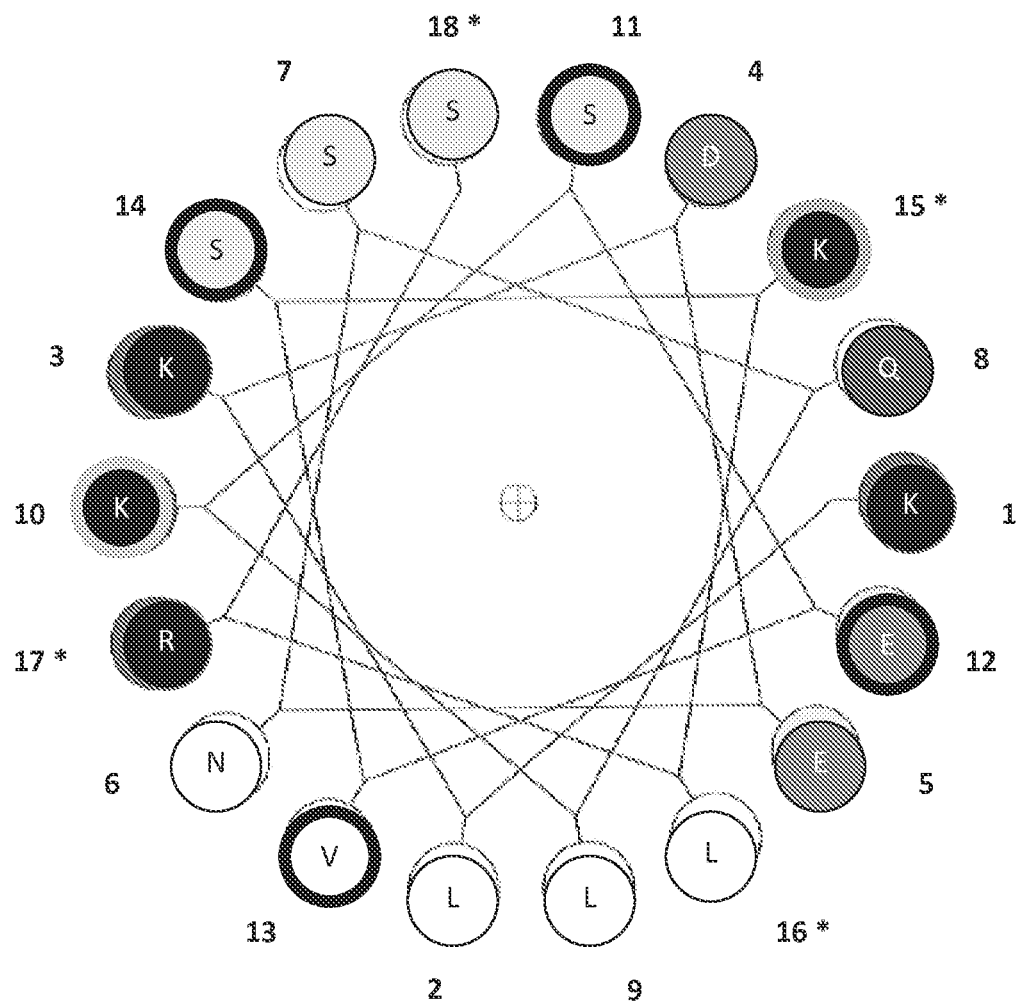
FIG. 5 provides a helical wheel prediction for the sequence KLKDENSQLKSEVSKLRS (SEQ ID NO: 5).

Secondary protein prediction tools indicate that this entire the region of RHAMM containing peptide B forms an alpha-helical coiled-coil. FIG. 5 shows a helical wheel prediction for the 18-amino acid long sequence KLKDEN-SQLKSEVSKLRS (SEQ ID NO: 5). Placing this sequence on a helical wheel results a helix having opposing faces of serines and leucines, which are known sites for protein:protein interactions in other proteins. These are flanked by pockets of charged amino acids. The adipogenic peptides described herein are predicted to disrupt the two faces and also at least one charged pocket.

In FIG. 5, residues 10-15 are the KSEVSK sequence (indicated by bolded outlines of the circles), which was used as the positive control in the adipogenesis assays described herein.

Example 4

Adipogenic Activity of KTRSHHV and Related Peptides

The 7-mer KTRSHHV (SEQ ID NO: 6) fragment derived from the carboxy terminus of the P15-1 peptide was tested for adipogenic effects in rat mesenchymal stem cells using Assays 1 and 2 described above in Example 1.

Adipogenesis was quantified by Oil Red O staining. The peptide was tested at concentrations of 5 and 50 µg/ml over a period of three weeks. Cells were plated in 48-well culture plates, and the purity of the peptides was >95%. All data are presented as the fold change relative to the negative control (Ctr(-))±standard error. The KSEVSK 6-mer (SEQ ID NO: 7) was used as a positive control.

Figure 6A:
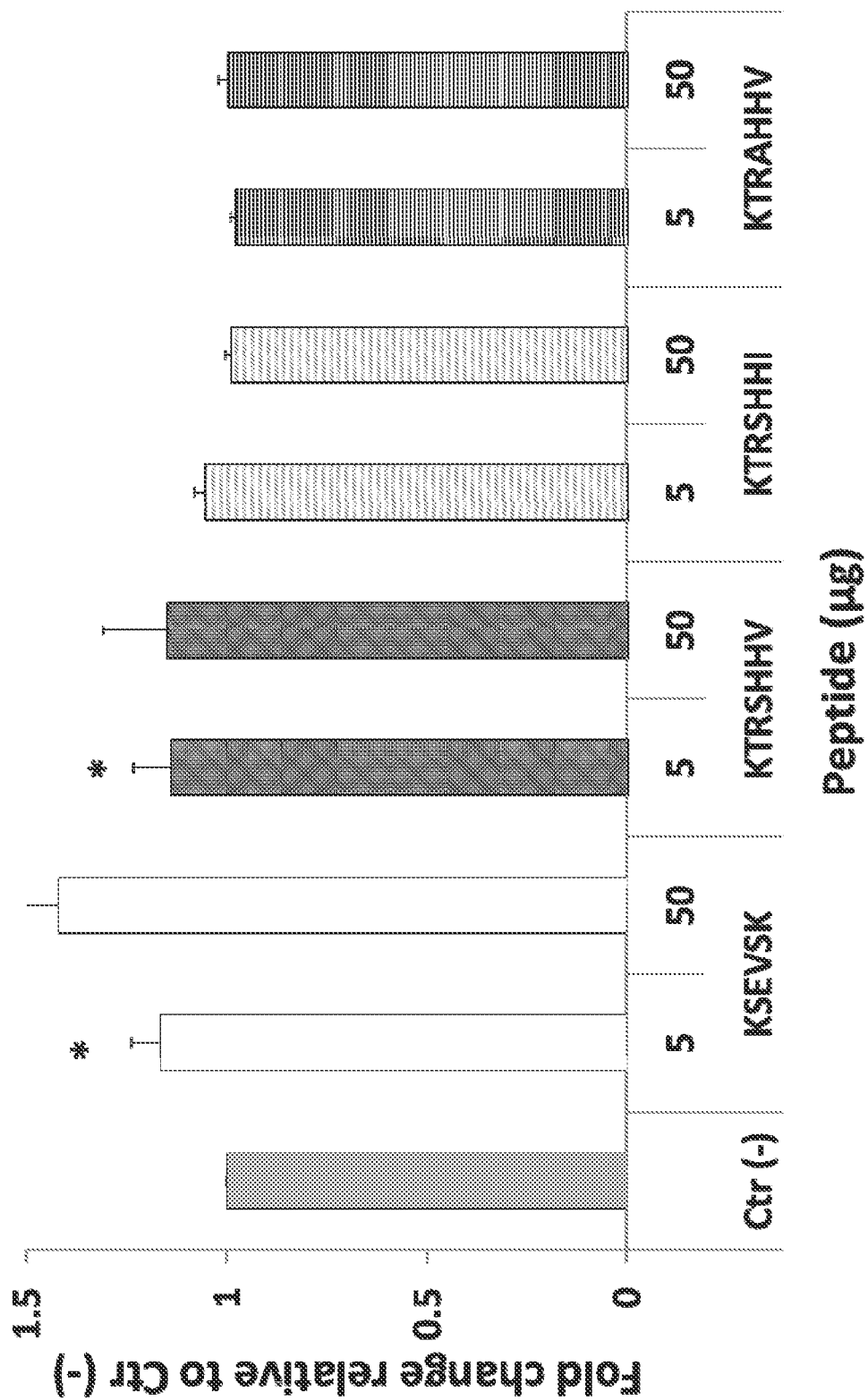
FIGS. 6A and 6B show illustrative data regarding the adipogenic effects of KTRSHHV (SEQ ID NO: 6) and several related sequences in Assay 1 (FIG. 6A) and Assay 2 (FIG. 6B).
Figure 6B:
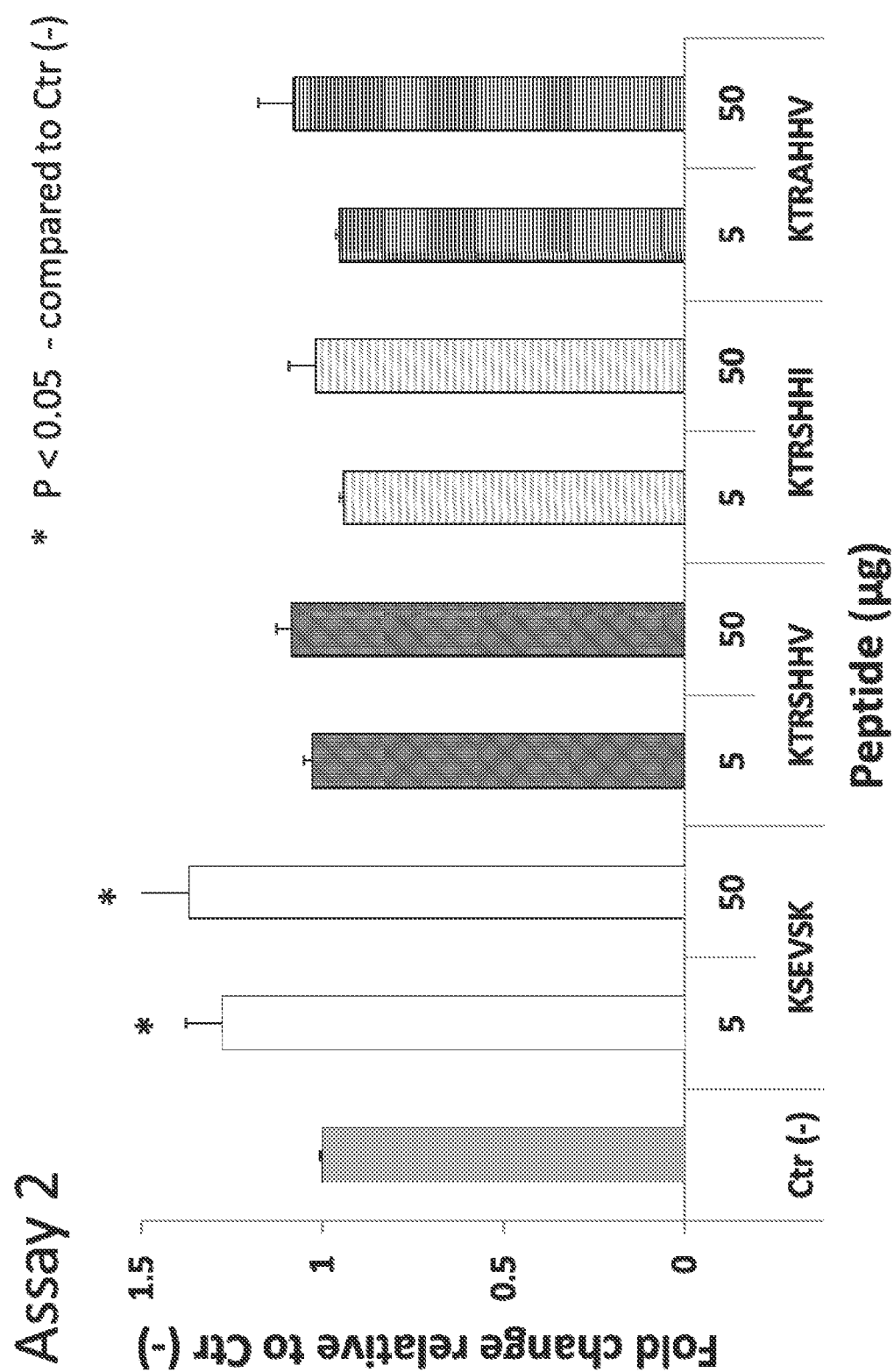

As shown in FIGS. 6A and 6B, the KTRSHHV fragment (SEQ ID NO: 6) derived from the carboxy terminus of the P15-1 peptide caused a significant increase in adipogenesis as compared to the negative control when used at a concentration of 5 µg/ml in assay 1, which is optimized for promoting adipogenesis in fibroblasts, but not in assay 2, which is optimized for differentiation of mesenchymal stem cells into adipocytes.

To identify a minimal motif sufficient to impart adipogenic activity to a peptide, a BLAST query of the sequence KTRSHHV (SEQ ID NO: 6) against the human genome and other genomes was used to identify a number of similar sequences found in other proteins including those linked to adipogenesis and/or hyaluronan and/or sugar metabolism and/or synthesis. The sequences identified in the BLAST query are shown below in Table 3.

TABLE 3

KTRSHHV-like sequences identified by BLAST searching

| Sequence | Source Protein(s) | SEQ ID NO. |
|---|---|---|
| Human | | |
| KTRSHSV | UPF0722 protein C11orf88 isoform 1 (human) | 62 |
| KTRSHTAHV† | cadherin EGF LAG seven-pass G-type receptor 1 precursor* | 63 |
| Other species | | |
| RTRSHHV | cupin domain-containing protein [Rhizoctonia solani AG-1 IA, imethylailyladenosine tRNA methylthiotransferase [Thermodesulfatator atlanticus] | 64 |
| KTKSHHV | LdpA, partial [uncultured Synechococcus sp., MULTISPECIES: XRE family transcriptional regulator [Vibrio], GH18783 [Drosophila grimshawi]* | 65 |
| KARSHHV | hypothetical protein EMIHUDRAFT_255630, partial [Emiliania huxleyi CCMP151.6], DNA-entry nuclease [Lactobacillus amylovorus GRL 1112 | 66 |
| KSRSHHV | predicted protein [Micromonas sp. RCC299], ADP-ribosylation factor-like protein 11 [Sorex araneus]* | 67 |

TABLE 3-continued

KTRSHHV-like sequences identified by BLAST searching

| Sequence | Source Protein(s) | SEQ ID NO. |
|---|---|---|
| KIRSHHV | Sugar transferase, PEP-CTERM/EpsH1 system associated [Novosphingobium resinovorum], glycosyl transferase family 1 [Novosphingobium sp. AP12], hypothetical protein [Novosphingobium lindaniciasticum], group 1 glycosyl transferase [Novosphingobium sp. PP1Y], prosper-homeobox protein 1-like [Latimeria chalumnae]* | 68 |
| KNRSHHV | V-type ATPase 116 kDa subunit [Dethiosulfovibrio peptidovorans]* | 69 |
| KPRSHHV | unnamed protein product [Oikopleura dioica], olfactory receptor KSOR5 [Lampropeltis getula]* | 70 |
| KTSSHHV | hypothetical protein ACD_44C00030G0002 [uncultured bacterium] membrane related protein CPS [Arabidopsis thaliana] | 71 |
| KDRSHHV | hypothetical protein PARA_13480 [Haemophilus parainfluenzae T3T1], ankyrin repeat [Pandoravirus salinus]* | 72 |
| KKRSHHV | unnamed protein product [Penicillium roqueforti] | 73 |
| KQRSHHV | oxidoreductase [Proteus penneri], FAD-binding oxidase (flavoprotein) [Proteus hauseri] | 74 |
| KERSHHV | Glycogen &branching enzyme [Arcticibacter svalbardensis]** | 75 |
| KLRSHHV | aldehyde dehydrogenase (NAD) family protein [Beauveria bassiana ARSEF 2860], olfactory receptor 4K1-like [Ochotona princeps]* | 76 |
| KVRSHHV | hypothetical protein Ecym_1322 [Eremothecium cymbalariae DBVPG#7215] putative transposase for insertion sequence element [Hyphomicrobium denitrificans 1NES1] | 77 |
| KTTSHHV | acylamino-acid-releasing enzyme, putative [Entamoeba invadens IP1]* | 78 |
| KSKSHHV | hypothetical protein Galf_1833 [Gallionella capsiferriformans ES-2] endonuclease/exonuclease/phosphatase domain-containing protein, putative [Eimeria praecox] | 79 |
| KTASHHV | hypothetical protein [Mycobacterium ,sp. 360MFTsu5.1] hypothetical protein MIMGU_mgv1a000031mg [Mimulus guttatus] | 80 |
| KTESHHV | hypothetical protein CGGC5_13625 [Colletotrichum gloeosporioides Nara gc5] | 81 |
| KTLSHHV | PREDICTED: uncharacterized protein KIAA1755 homolog [Pteropus alecto] hypothetical protein PAL_GLEAN10024321 [Pteropus alecto] | 82 |
| KRRSHHV | Hypothetical protein [Bradyrhizobium sp. STM 3809] | 83 |
| KTYSHHV | hypothetical protein [Bacteroides sp. D2] endo-1,4-beta-xylanase [Sphingobacterium spiritivorum]** | 84 |
| RTKSHHV | nerve growth factor beta polypeptide, partial [Chamaeleo calyptratus]* | 85 |

TABLE 3-continued

KTRSHHV-like sequences identified by BLAST searching

| Sequence | Source Protein(s) | SEQ ID NO. |
|---|---|---|
| KTRSHHI | FGFR1 oncogene partner isoform X2 [*Monodelphis domestica*]* | 86 |
| KTRAHHV | hypothetical protein X809_19600 [*Paenibacillus polymyxa* CR1] | 87 |

*Sequence found in protein(s) implicated in adipogenesis
**Sequence found in protein(s) implicated in HA and/or sugar metabolism and/or synthesis
†The sequence KTRSHTAHV (SEQ ID NO: 63) has insertions, which are shown in bold text and underlined KTRSHHI (SEQ ID NO: 86) and KTRAHHV (SEQ ID NO: 87) were tested for adipogenic activity in Assays 1 and 2 using the same methods as described above for KTRSHHV (SEQ ID NO: 6). It was found that substitution of the carboxy terminal valine of KTRSHHV (SEQ ID NO: 6) with an isoleucine or substitution of the serine at position four of KTRSHHV with an alanine ablated adipogenic activity when these peptides were tested for adipogenic activity in Assay 1 or 2 described above in Example 1 (see FIG. 6A). These results show that even very conservative substitutions at the carboxy terminal valine of KTRSHHV (SEQ ID NO: 6) can ablate adipogenic activity, indicating that the carboxy terminal valine is important for adipogenic activity. Substitution of the serine at position four of KTRSHHV (SEQ ID NO: 6) with an alanine also ablated adipogenic activity when this peptide was tested in Assay 1 or Assay 2, but as explained further below in Example 8, KTRAHHV (SEQ ID NO: 87) induced adipogenesis in vivo in rats injected with this peptide.

The sequences in Table 3 were aligned with one another and with the KTRSHHV (SEQ ID NO: 6) sequence, and in combination with the data in FIG. 6A as well as the data described in Examples 6 and 8 below and shown in FIGS. 8, 9, and 12, were used to generate the motifs described herein. In addition, it was previously reported in U.S. Pat. No. 6,271,344 that the peptide STMMSRSHKTRSCHH (SEQ ID NO: 88) binds to HA. Thus, the motifs described herein allow for a cysteine insertion following the serine or alanine residue present at position four of the peptides in this family.

The KTRSHHV sequence (SEQ ID NO: 6) aligns with a sequence from RHAMM that starts with the carboxyl terminal lysine of the KSEVSK sequence (KLRSQLVK, SEQ ID NO: 89) as follows:

```
                                        (SEQ ID NO: 6)
    KTRSHHV (SEQ ID NO: 89, RHAMM sequence)
    KLRSQLVK
```

The asterisks in the helical wheel shown in FIG. 5 indicate that KTRSHHV (SEQ ID NO: 6) will align with K15, L16, R17 and S18 so that it will disrupt the serine and leucine faces and two charged pockets.

Example 5

Evaluation of the Adipogenic Effects of the Peptides Using an Adiponectin Assay

The peptides described above as well as certain additional peptides were further assessed for their ability to stimulate adiponectin secretion. The methods described in this example were used to generate the data described below in Example 6 and shown in FIGS. 7, 8, and 9.

Culture and Adipogenic Differentiation of 3T3L Cells:

3T3L cells were cultured in T75 culture flasks, in expansion medium (Millipore Corporation), and stored in a 5% $CO_2$ humidified incubator at 37° C. Media was changed every two days until the cells reached 80% confluency. Cells were subcultured in a 96 well plate with a seeding density of $3 \times 10^4$ cells per $cm^2$.

Once cells had just reached confluency, expansion media was replaced with 0.5 mL of Adipogenic Induction Media per well containing 5% serum that had been screened for an ability to maintain stem cells in an undifferentiated state (LifeTechnologies). Cells were incubated for 48 hours at 37° C., 5% $CO_2$. The Adipogenic Induction Media contained DMEM (low glucose, Gibco) +5% serum (LifeSciences) with 0.5 mM IBMX solution, 1 µM Dexamethasone Solution, and 100 µM Indomethacin Solution (priming stimulus). After 48 hr the Adipogenic Induction media was replaced with new media containing 10 µg/ml insulin alone (positive control), or 10 µg/ml peptide (experimental conditions). Negative controls were DMEM +5% serum only. Plates were incubated for two days prior to adiponectin ELISA analyses. Peptides were added daily at 10 µg/ml throughout the remainder of the experiment.

Peptide Synthesis and Purification:

Peptides were synthesized and purified to >90% purity. Purity of peptides was confirmed using mass spectrophotometry.

Adiponectin ELISA for in Vitro Quantification of Adipogenesis:

Adiponectin present in the supernatant medium was measured using a mouse adiponectin ELISA (Novex, LifeTechnologies). Briefly, supernatant medium was collected and diluted 1:100. One hundred microliters of the diluted supernatant medium was added to each well of the ELISA plate and incubated for one hour at 37° C. Wells were washed three times with 1× wash buffer and then 100 µl of antibody was added to each well and incubated for one hour at 37° C. The wells were then washed and incubated with 100 µl detector antibody for 1 hr at 37° C. The wells were washed five times with wash buffer and 100 µl of substrate solution was added to each well and incubated for twenty minutes in the dark. The reaction was then stopped by the addition of 100 µl stop solution. Plates were read at 450 nm and concentrations of adiponectin were derived from a standard curve included in the ELISA plate.

Example 6

Testing of KLKDENSQLK, KTRSHHV, and Related Peptides for Ability to Stimulate Adiponectin Secretion The peptides KLKDENSQLK (SEQ ID NO: 3), KTRSHHV (SEQ ID NO: 6), and peptides related to each of these sequences were tested for their ability to stimulate adiponectin secretion in vitro.

Figure 7:
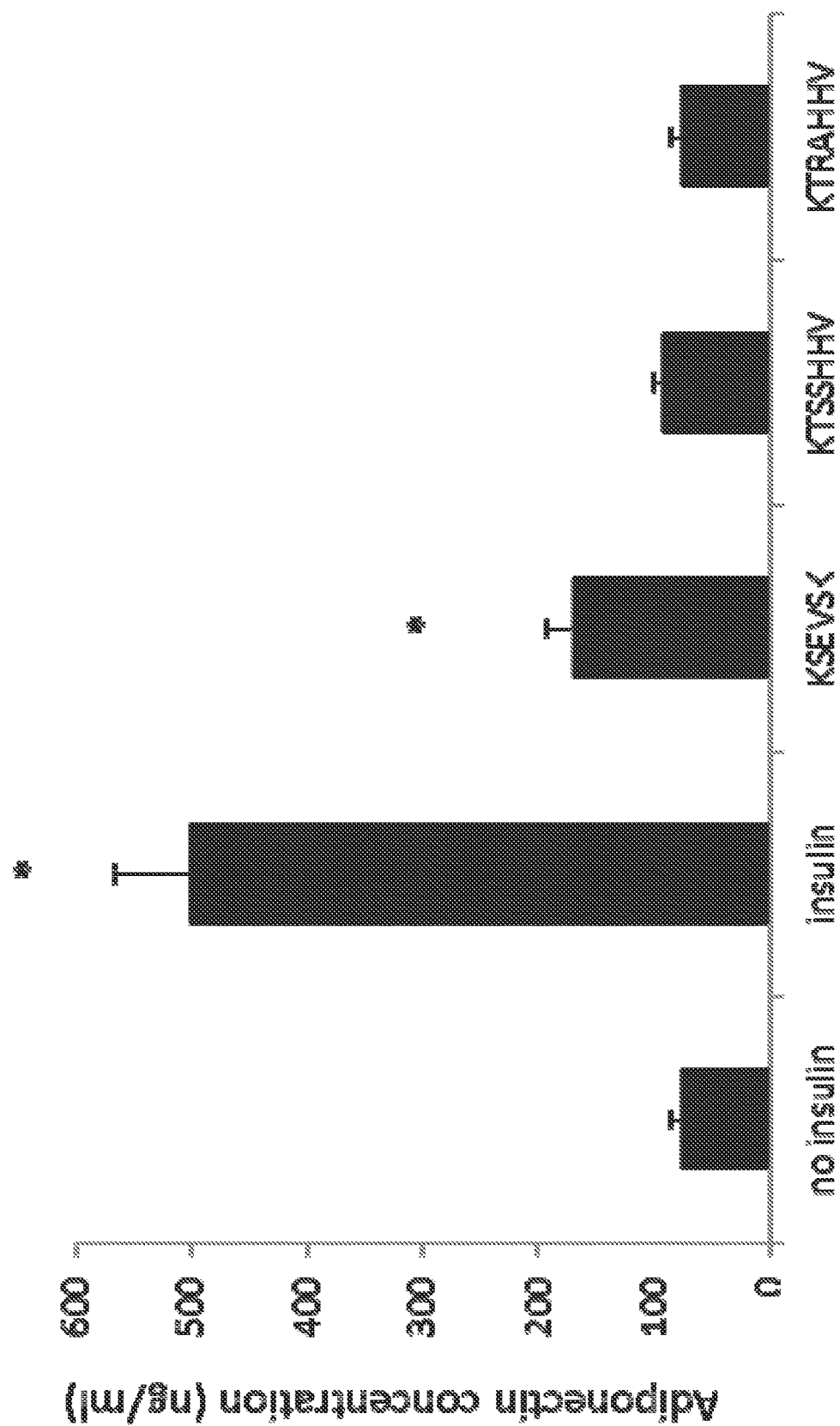

To verify that the adiponectin assay could be used to detect the adipogenic activity of insulin and peptides, adiponectin concentrations were measured in supernatant medium from 3T3L cells that received IBMX, dexamethasone and indomethacin (e.g. "primed") but had not been induced with insulin (no insulin), "primed" and received insulin (insulin), or "primed" and treated with peptides (KSEVSK (SEQ ID NO: 7), KTSSHHV (SEQ ID NO: 71), or KTRAHHV (SEQ ID NO: 87)). Insulin and the KSEVSK peptide (SEQ ID NO: 7) served as positive controls. KTSSHHV (SEQ ID NO: 71) and KTRAHHV (SEQ ID NO: 87) are examples of peptides that were found to lack an ability to promote adipogenesis when assayed using the adiponectin assay. (However, as described further below in Example 8, KTRAHHV (SEQ ID NO: 87) was found to induce adipogenesis in vivo in mammary fat pads of aged female rats). The results of this assay are shown in FIG. 7. In FIG. 7, values marked by asterisks represent significant changes relative to the no insulin control (i.e., the negative control) using a two-tailed Student's T test, $p<0.05$.

KLKDENSQLK (SEQ ID NO: 3) and certain peptides related to KLKDENSQLK were tested for adipogenic activity using the adiponectin assay. In addition to KLKDENSQLK (SEQ ID NO: 3), KLKDENSNLK (SEQ ID NO: 19), KLKDDNSQLK (SEQ ID NO: 16), and KLKDENSQLR (SEQ ID NO: 17) were selected for testing from among the evolutionarily conserved RHAMM sequences listed in Table 1 above. KLKDENSQLR (SEQ ID NO: 17) was also identified in the BLAST search for sequences similar to KLKDENSQLK (SEQ ID NO: 3) in other proteins (see Table 2 above). Many of the other evolutionarily conserved RHAMM sequences in Table 1 and the sequences identified by BLAST searching for sequences similar to KLKDENSQLK (SEQ ID NO: 3) in other proteins (Table 2) had multiple differences as compared to KLKDENSQLK. In order to identify amino acids important for adipogenicity, peptides were synthesized that had only a single amino acid substitution as compared to KLKDENSQLK (SEQ ID NO: 3). The single amino acid substitutions were selected based on the sequences shown in Tables 1 and 2. The evolutionarily conserved RHAMM sequences listed in Table 1 showed that the lysine residues at positions 1 and 3 of KLKDENSQLK (SEQ ID NO: 3) were highly conserved. Alanine was therefore substituted for each of these lysine residues to create the peptides ALKDENSQLK (SEQ ID NO: 90) and KLADENSQLK (SEQ ID NO: 91). In contrast, the leucine at position 2 and the serine at position 7 of KLKDENSQLK (SEQ ID NO: 3) varied in the sequences shown in Tables 1 and 2. Thus, based on the amino acids present at these positions in the sequences in Tables 1 and 2, an isoleucine or threonine residue was substituted for the leucine at position 2 of KLKDENSQLK (SEQ ID NO: 3) to create the peptides KIKDENSQLK (SEQ ID NO: 92) and KTKDENSQLK (SEQ ID NO: 93), respectively. A threonine was substituted for the serine at position 7 of KLKDENSQLK (SEQ ID NO: 3) to create the peptide KLKDENTQLK (SEQ ID NO: 94). Similarly, the aspartic acid at position 4 and the leucine at position 9 of KLKDENSQLK (SEQ ID NO: 3) also varied in the sequences shown in Tables 1 and 2. Thus, based on the amino acids present at these positions in Tables 1 and 2, a threonine was substituted for the aspartic acid at position 4 of KLKDENSQLK (SEQ ID NO: 3) to create the peptide KLKTENSQLK (SEQ ID NO: 95) and a lysine was substituted for the leucine at position 9 of KLKDENSQLK (SEQ ID NO: 3) to create the peptide KLKDENSQKK (SEQ ID NO: 96). These peptides were tested for their ability to stimulate adiponectin secretion.

Figure 8:
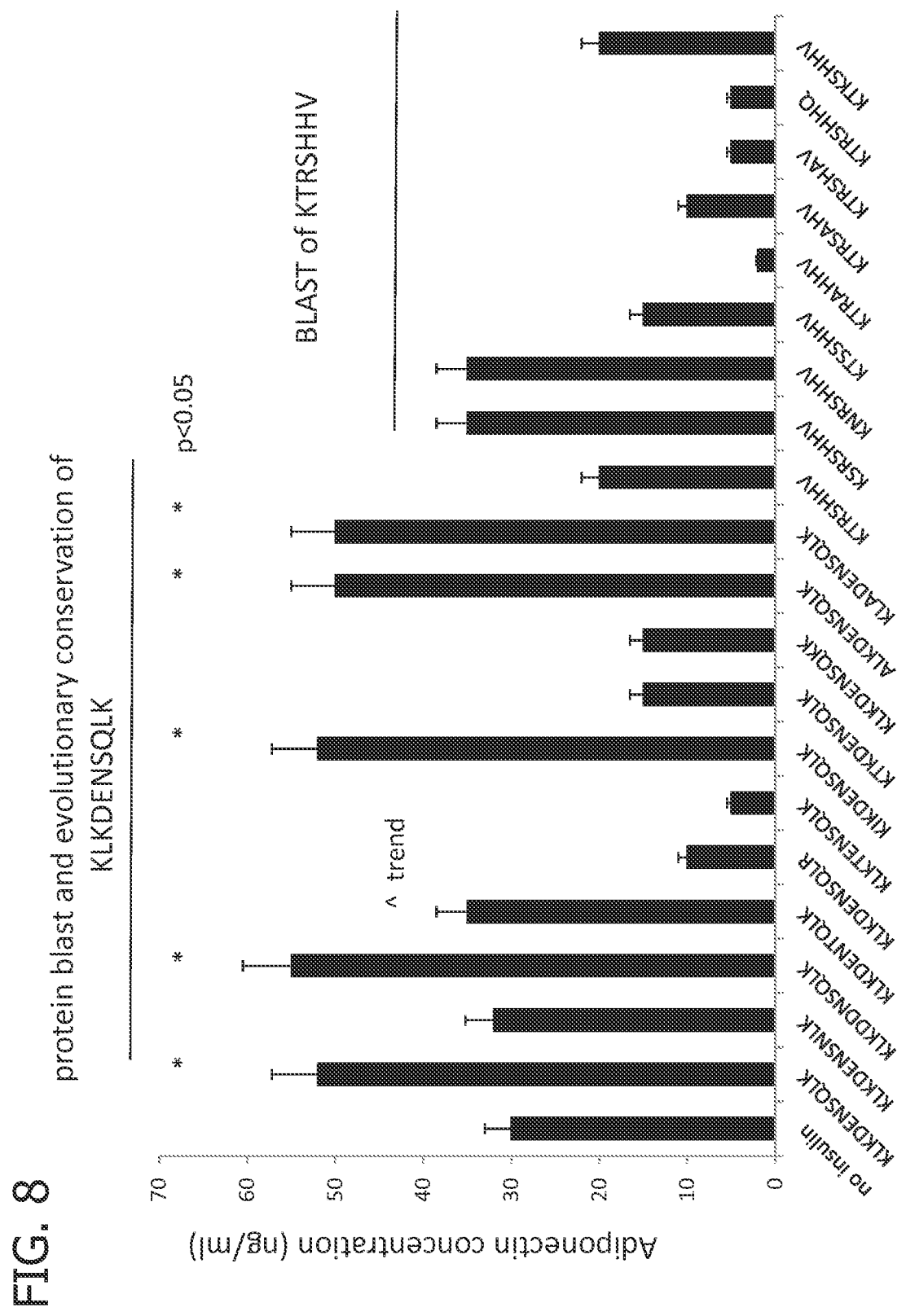

The results of this assay are shown in FIG. 8. Adiponectin concentrations were measured in supernatant medium from 3T3L cells that had received a priming stimulus of IBMX, dexamethasone and indomethacin "primed" but not induced with insulin (no insulin), or "primed" and treated with the indicated peptide. In FIG. 8, asterisks mark significant increases compared to the no insulin control (two-tailed Student's T test, $p<0.05$) while ^ marks changes that trended towards increases when compared to the no insulin control but were not statistically significant at $p<0.05$.

FIG. 8 shows that while the peptide KLKDENSQLR was not subsequently shown to be adipogenic in adiponectin and rat mammary fat pad assays, this peptide had initially showed promising results in Oil Red O assays, and alanine walking was therefore performed using the KLKDENSQLR peptide. Single alanine mutations were made at each of positions 1-10 of KLKDENSQLR (SEQ ID NO: 17) to create the peptides ALKDENSQLR (SEQ ID NO: 97), KAKDENSQLR (SEQ ID NO: 98), KLADENSQLR (SEQ ID NO: 99), KLKAENSQLR (SEQ ID NO: 100), KLKDANSQLR (SEQ ID NO: 101), KLKDEASQLR (SEQ ID NO: 102), KLKDENAQLR (SEQ ID NO: 103), KLKDENSALR (SEQ ID NO: 104), KLKDENSQAR (SEQ ID NO: 105), and KLKDENSQLA (SEQ ID NO: 106). The peptides KLKDENSQLR (SEQ ID NO: 17) and KLKTENSQLR (SEQ ID NO: 107) were also included in this assay. KLKTENSQLR (SEQ ID NO: 107) was tested in order to assess the importance of the aspartic acid at the four position of KLKDENSQLK (SEQ ID NO: 3). A threonine residue was selected to replace the aspartic acid since there is a threonine at position 4 of the *Xenopus laevis* RHAMM sequence (see SEQ ID NO: 23 in Table 1). These peptides were synthesized, purified and purity was confirmed as described in Example 5 above. These peptides were tested for their ability to stimulate adiponectin secretion.

Figure 9:
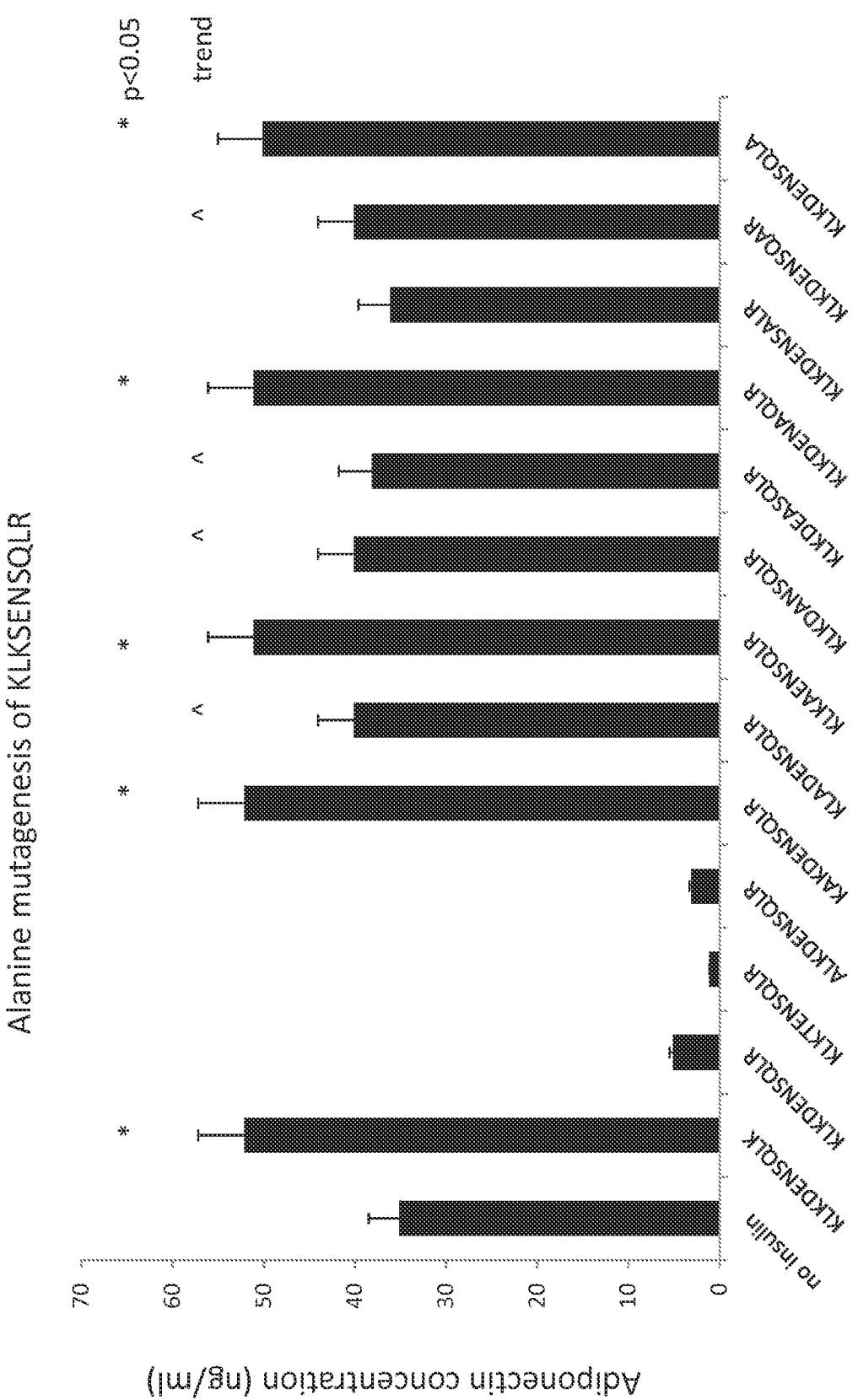

The results of this assay are shown in FIG. 9. Adiponectin concentrations were measured in supernatant medium of 3T3L cells that had been "primed" with IBMX, dexamethasone and indomethacin but not induced with insulin (no insulin), or "primed" and treated with the indicated peptides. In FIG. 9, significant increases in adiponectin production relative to the no insulin control are marked by asterisks (two-tailed Student's T test, $p<0.05$) while ^ marks changes that trended towards increases when compared to the no insulin control but were not statistically significant at $p<0.05$.

The adiponectin assay was also used to test KTRSHHV (SEQ ID NO: 6) and certain related peptides for adipogenic activity using the adiponectin assay. In addition to KTRSHHV (SEQ ID NO: 6), the peptides KTKSHHV (SEQ ID NO: 65), KSRSHHV (SEQ ID NO: 67), KNRSHHV (SEQ ID NO: 69), KTSSHHV (SEQ ID NO: 71), and KTRAHHV (SEQ ID NO: 87), which were identified in the BLAST query of the sequence KTRSHHV (SEQ ID NO: 6) to identify similar sequences found in other proteins (see Table 3 above), were tested. In addition, the sequences identified in this BLAST query indicated that the histidine residues at positions 5 and 6 and the valine at position 7 were highly conserved. The histidine residues at positions 5 and 6 were therefore each substituted with alanine to create the peptides KTRSAHV (SEQ ID NO: 108) and KTRSHAV (SEQ ID NO: 109). The valine at position 8 was substituted with a glutamine (a non-conservative substitution was selected, since both valine and alanine are hydrophobic) to create the peptide KTRSHHQ (SEQ ID NO: 110). These peptides were tested for their ability to stimulate adiponectin secretion using the assay described above. The results of this assay are shown in FIG. 8. As noted above, in FIG. 8, asterisks mark significant increases compared to the no insulin control (two-tailed Student's T test, p<0.05) while ˆ marks changes that trended towards increases when compared to the no insulin control but were not statistically significant at p<0.05.

Example 7

In Vivo Testing of Peptides for Adipogenesis in Rats

Peptides were also tested for their ability to stimulate adipogenesis in mammary fat pads of aged (8 month old) female rats in vivo. Mammary fat pads are rich in adipocyte progenitor cells. The methods described in this example were used to generate the data described below in Example 8 and shown in FIGS. 11 and 12.

Peptides were synthesized and purified and purity of peptides was confirmed by mass spectrophotometry as described above in Example 5.

Figure 10:
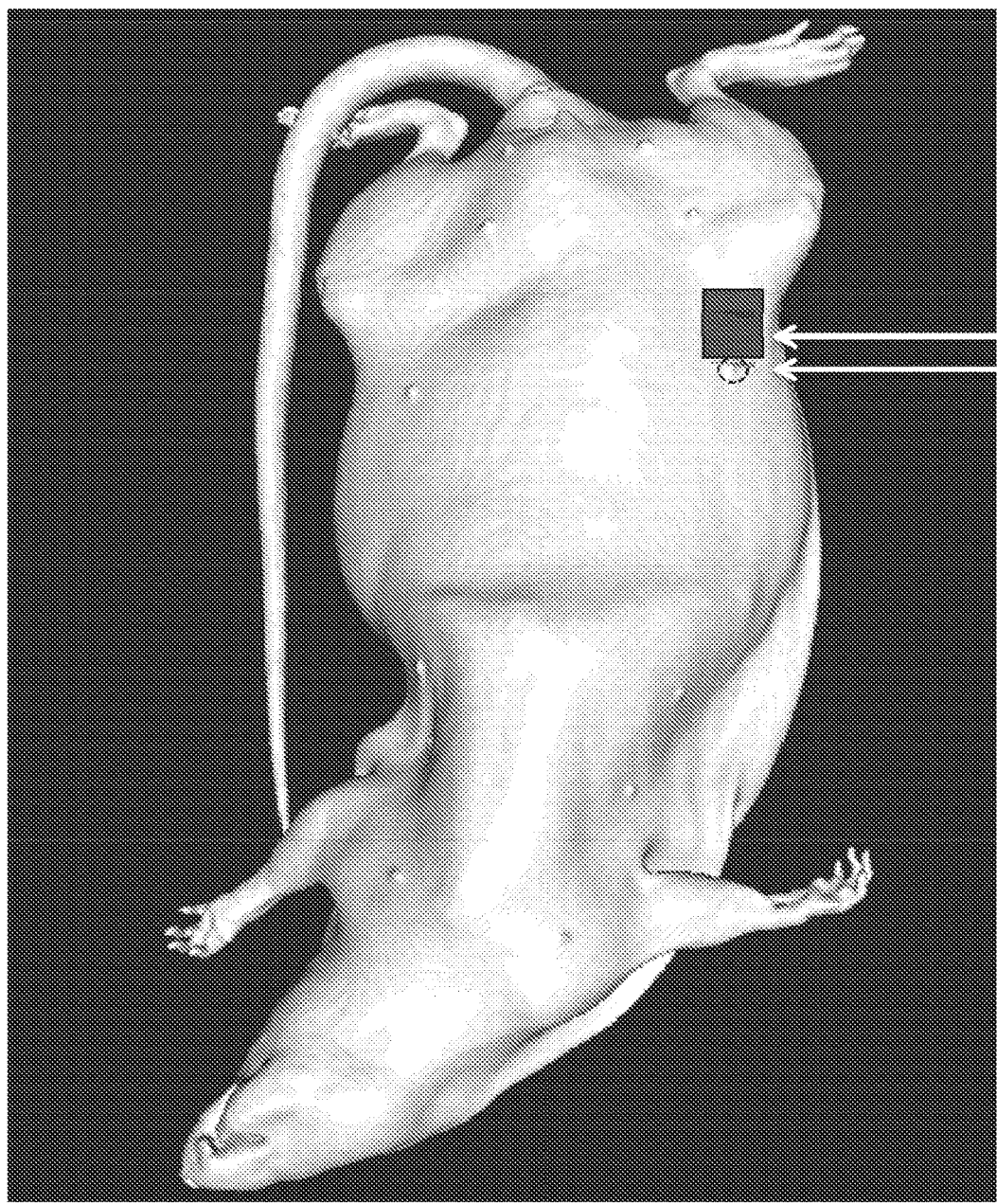
FIG. 10 provides an image of a rat showing the location (region of interest, black square) used to measure adipogenesis in the fourth right mammary fat pad under the nipple (indicated by the dotted circle).

Eight-month-old female Sprague Dawley rats (retired breeders) were injected with 100 μl collagen gel (Vitrogen) containing 100 μg peptide into the fourth right mammary fat pad, as depicted in FIG. 10. FIG. 10 shows an image of a rat showing the location of the fourth right mammary pad (region of interest (ROI)) as a black square under the nipple (dotted circle). The collagen and peptides were injected at the top of the ROI nearest the nipple. The fat pad is below the nipple as can be seen in the transverse sections shown in FIG. 11. The collagen and peptide diffuse into the fat pad following injection and active peptides target RHAMM-positive progenitor cells present in the fat pad. Collagen alone was injected into the fourth left mammary fat pad as a negative control.

Following injection of the collagen and peptide or collagen alone, animals were maintained on rat chow and water for 7 days and then euthanized. Micro-computed tomography (microCT) imaging of the mice was performed on animals using a Locus Ultra scanner (GE Healthcare, London, ON, Canada). The animals were imaged ex vivo with an X-ray tube voltage of 80 kV and a tube current of 55 mA. Nine hundred projections of data were acquired at an angular increment of 0.4 degrees around the rat in an exposure time of 16 ms. The data were then reconstructed into a 3D volume image with a voxel size of 154 μm. The subcutaneous mammary fat measured in 10×5×3 mm rectangular area (the region of interest (ROI)) below the nipple, avoiding measurement of underlying visceral fat (see the region labeled "fat pad" in FIG. 11). The amount of fat in the ROI was calculated as mass (mg) per ROI.

Example 8

Figure 11:
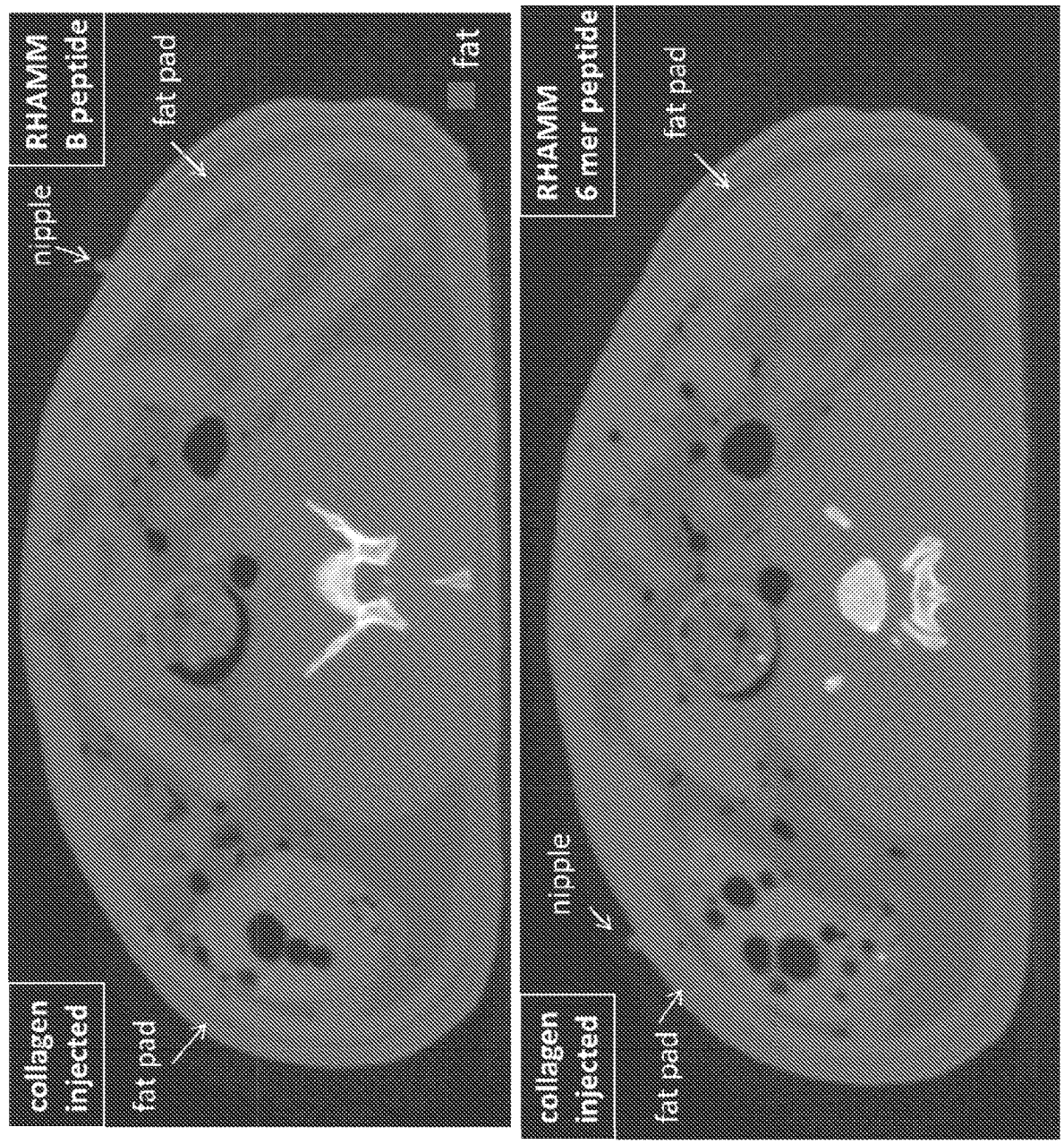
FIG. 11 provides illustrative microCT images showing mammary fat pad enlargement in aged female rats treated with the peptide KLKDENSQLKSEVSK (SEQ ID NO: 2; "RHAMM B peptide") or KSEVSK (SEQ ID NO: 7; "RHAMM 6 mer peptide").

Testing of KLKDENSQLK, KTRSHHV, and Related Peptides for Their Ability to Stimulate Adipogenesis in Vivo In an initial experiment conducted to verify that peptides known to be adipogenic could stimulate adipogenesis in vivo, KLKDENSQLKSEVSK (SEQ ID NO: 2, the B peptide) and KSEVSK (SEQ ID NO: 7) were tested for their ability to stimulate adipogenesis in vivo in rats using the methods described above in Example 7. The results of this testing are shown in FIG. 11. Specifically, FIG. 11 provides microCT images showing mammary fat pad enlargement in the right fourth mammary fat pads of eight-month-old female rats, which were injected with KLKDENSQLKSEVSK (SEQ ID NO: 2, "RHAMM B peptide," upper image) or KSEVSK (SEQ ID NO: 7, "RHAMM 6 mer peptide," lower image). The left fourth mammary fat pads were injected with collagen gel only and served as negative controls.

KLKDENSQLK (SEQ ID NO: 3) and the related peptides KLKDENSNLK (SEQ ID NO: 19), KLKDDNSQLK (SEQ ID NO: 16), KLKDENTQLK (SEQ ID NO: 94), KLKDENSQLR (SEQ ID NO: 17), KLKTENSQLK (SEQ ID NO: 95), KIKDENSQLK (SEQ ID NO: 92), KTKDENSQLK (SEQ ID NO: 93), KLKDENSQKK (SEQ ID NO: 96), ALKDENSQLK (SEQ ID NO: 90), and KLADENSQLK (SEQ ID NO: 91) were also tested for their ability to stimulate adipogenesis in vivo using the methods described in Example 7. In addition, KTRSHHV (SEQ ID NO: 6) and the related peptides KTKSHHV, KSRSHHV (SEQ ID NO: 67), KNRSHHV (SEQ ID NO: 69), KTSSHHV (SEQ ID NO: 71), KTRAHHV (SEQ ID NO: 87), KTRSAHV (SEQ ID NO: 108), KTRSHAV (SEQ ID NO: 109), and KTRSHHQ (SEQ ID NO: 110) were likewise tested for their ability to stimulate adipogenesis in vivo.

Figure 12:
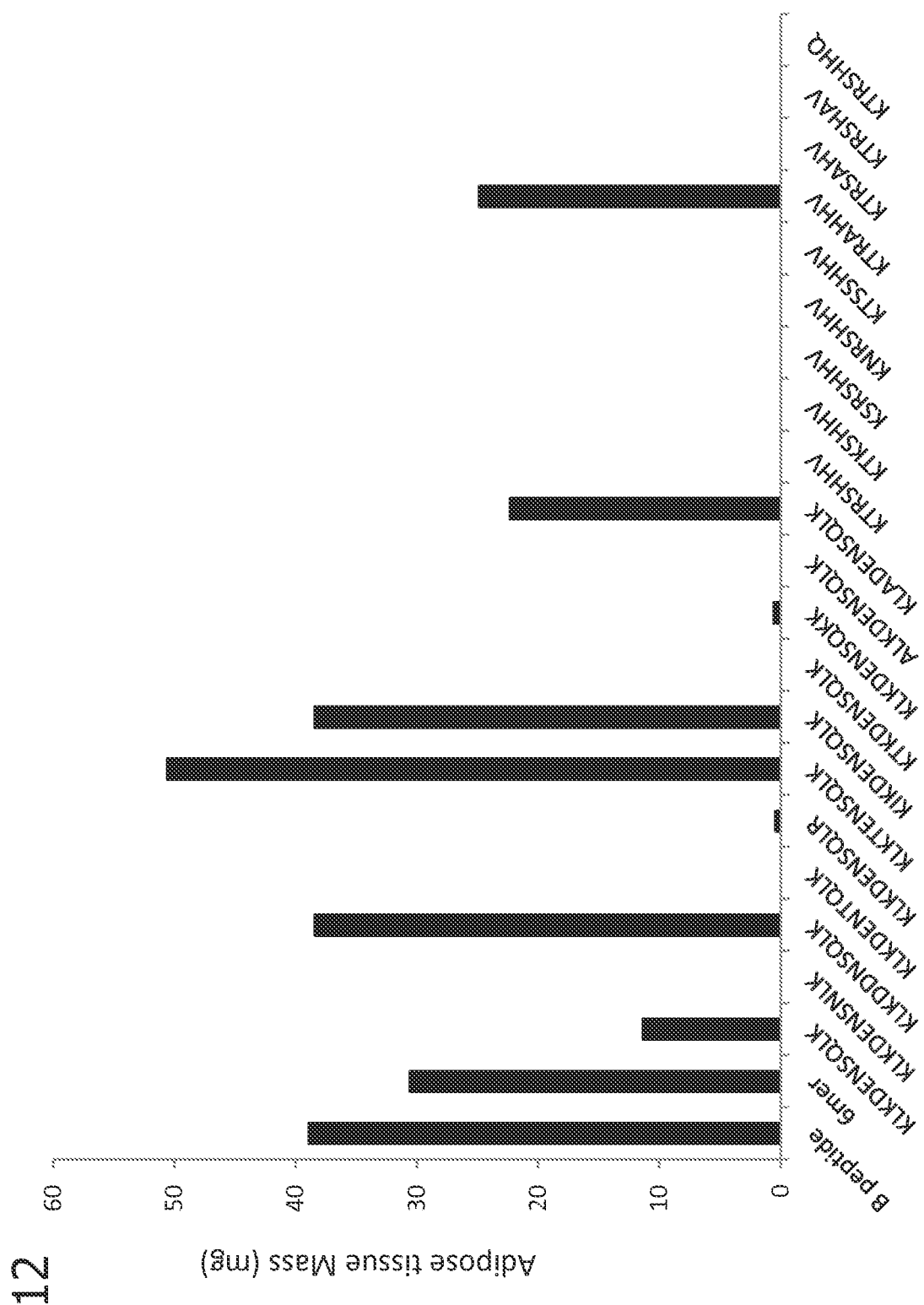
FIG. 12 provides illustrative microCT for peptides injected into mammary fat pads in aged female rats.

The results of this testing are shown in FIG. 12. In particular FIG. 12 shows the effects of the indicated peptides on adipogenesis in the fourth mammary fat pads of eight-month-old female rats. Values shown are peptide-treated fat pads minus collagen only fat pads quantified as milligrams adipose tissue mass per ROI. In FIG. 12, "B peptide" refers to the peptide KLKDENSQLKSEVSK (SEQ ID NO: 2) and "timer" refers to the peptide KSEVSK (SEQ ID NO: 7).

It will be appreciated from the foregoing that some peptides exhibited adipogenic activity in each of the assays in which they were tested. For example, the peptide KLKDENSQLK (SEQ ID NO: 3) exhibited activity in Assays 1 and 2 (with quantification of adipogenesis by Oil Red O staining), in the adiponectin assay, and in vivo following injection into female rats. Others of the peptides exhibited adipogenic effects in some assays but not others. For example, KTRASHHV did not exhibit adipogenic activity in the adiponectin assay, but was able to induce adipogenesis in vivo. Without wishing to be bound to any particular theory, it is believed that differences between assays can result from peptide stability in culture vs. in vivo, availability/number of appropriate RHAMM-positive adipocyte precursor cells, and differences in assay sensitivity. For example, if peptides are unstable in serum (e.g. cultures contain 5-10% serum), their activity may be blunted in culture as compared to an injection into a tissue in vivo (e.g., a mammary fat pad) which does not contain serum. In addition, the adiponectin assay is more sensitive than the Oil Red O assays (Assays 1 and 2) and measure an early stage in adipogenesis as compared to Oil Red O which measures the end stage (e.g. fat droplets) of this differentiation process.

When introducing elements of the present invention or the preferred embodiments(s) thereof, the articles "a," "an," "the" and "said" are intended to mean that there are one or more of the elements. The terms "comprising," "including"

and "having" are intended to be inclusive and mean that there may be additional elements other than the listed elements.

In view of the above, it will be seen that the several objects of the invention are achieved and other advantageous results attained.

As various changes could be made in the above peptides, compositions, and methods without departing from the scope of the invention, it is intended that all matter contained in the above description and shown in the accompanying drawings shall be interpreted as illustrative and not in a limiting sense.

What is claimed is:

1. A modified peptide or peptidomimetic having a length of 10 to 14 amino acids and comprising the sequence (III):

$$Z1\text{-}Z2\text{-}Z3\text{-}Z4\text{-}Z5\text{-}Z6\text{-}Z7\text{-}Z8\text{-}Z9\text{-}Z10 \quad (III)$$

wherein:
- Z1 is lysine (K) or alanine (A);
- Z2 is leucine (L), isoleucine (I), or alanine (A);
- Z3 is lysine (K) or alanine (A);
- Z4 is aspartic acid (D), threonine (T), or alanine (A);
- Z5 is glutamic acid (E);
- Z6 is asparagine (N)
- Z7 is serine (S) or alanine (A);
- Z8 is glutamine (Q);
- Z9 is leucine (L); and
- Z10 is lysine (K), arginine (R), or alanine (A);

wherein the modified peptide:
- comprises a protecting group, wherein the modified peptide has improved ex vivo and/or in vivo peptide stability and/or improved skin penetration when administered topically, relative to an unmodified peptide of the same sequence; or
- is functionalized with a polymer selected from the group consisting of a polyethylene glycol, a cellulose, and a modified cellulose, wherein the modified peptide has increased bioavailability, relative to an unmodified peptide of the same sequence; and wherein the peptidomimetic comprises one or more peptide linkages replaced with a linkage selected from the group consisting of —CH$_2$NH—, —CH$_2$S—, —CH$_2$—CH$_2$—, —CH=CH—, —COCH$_2$—, —CH(OH)CH$_2$—, and —CH$_2$SO, wherein the peptidomimetic has an improvement in a property, relative to an unmodified peptide of the same sequence, wherein the property is selected from the group consisting of: economy of production, chemical stability, half-life, absorption, potency, efficacy, and/or reduced antigenicity.

2. The modified peptide or peptidomimetic of claim 1, which is a modified peptide comprising a protecting group, wherein the modified peptide has improved ex vivo and/or in vivo peptide stability and/or improved skin penetration when administered topically, relative to an unmodified peptide of the same sequence.

3. The modified peptide or peptidomimetic of claim 1, which is a modified peptide functionalized with a polymer selected from the group consisting of a polyethylene glycol, a cellulose, and a modified cellulose, wherein the modified peptide has increased bioavailability, relative to an unmodified peptide of the same sequence.

4. The modified peptide or peptidomimetic of claim 1, which is a peptidomimetic comprising one or more peptide linkages replaced with a linkage selected from the group consisting of —$CH_2NH$—, —$CH_2S$—, —$CH_2$—$CH_2$—, —CH=CH—, —$COCH_2$—, —$CH(OH)CH_2$—, and —$CH_2SO$, wherein the peptidomimetic has an improvement in a property, relative to an unmodified peptide of the same sequence, wherein the property is selected from the group consisting of: economy of production, chemical stability, half-life, absorption, potency, efficacy, and/or reduced antigenicity.

5. A pharmaceutical or cosmetic composition comprising: the modified peptide or peptidomimetic of claim 1; and a pharmaceutically or cosmetically acceptable carrier.

6. The composition of claim 5, wherein the composition is for topical administration, subcutaneous administration, transdermal administration, or injection.

7. The composition of claim 5, wherein the composition further comprises collagen and/or an anesthetic.

8. The modified peptide or peptidomimetic of claim 1, wherein the amino acid sequence of the modified peptide or peptidomimetic comprises KIKDENSQLK (SEQ ID NO: 92).

9. The modified peptide or peptidomimetic of claim 1, wherein the amino acid sequence of the modified peptide or peptidomimetic comprises ALKDENSQLK (SEQ ID NO: 90).

10. The modified peptide or peptidomimetic of claim 1, wherein the amino acid sequence of the modified peptide or peptidomimetic comprises KLADENSQLK (SEQ ID NO: 91).

11. The modified peptide or peptidomimetic of claim 1, wherein the amino acid sequence of the modified peptide or peptidomimetic comprises KAKDENSQLR (SEQ ID NO: 98).

12. The modified peptide or peptidomimetic of claim 1, wherein the amino acid sequence of the modified peptide or peptidomimetic comprises KLKAENSQLR (SEQ ID NO: 100).

13. The modified peptide or peptidomimetic of claim 1, wherein the amino acid sequence of the modified peptide or peptidomimetic comprises KLKDENAQLR (SEQ ID NO: 103).

14. The modified peptide or peptidomimetic of claim 1, wherein the amino acid sequence of the modified peptide or peptidomimetic comprises KLKDENSQLA (SEQ ID NO: 106).

15. The modified peptide or peptidomimetic of claim 1, wherein the amino acid sequence of the modified peptide or peptidomimetic comprises KLKTENSQLK (SEQ ID NO: 95).

16. The modified peptide or peptidomimetic of claim 1, wherein the modified peptide or peptidomimetic is capable of stimulating subcutaneous adipogenesis.

17. A method of stimulating adipogenesis in a subject, the method comprising administering the modified peptide or peptidomimetic of claim 1 topically to a subject in an amount sufficient to stimulate adipogenesis.

18. A method of stimulating adipogenesis in a subject, the method comprising administering the modified peptide or peptidomimetic of claim 1 subcutaneously to a subject in an amount sufficient to stimulate adipogenesis.

19. A method of stimulating adipogenesis in a subject, the method comprising administering the modified peptide or peptidomimetic of claim 1 transdermally to the subject in an amount sufficient to stimulate adipogenesis.

20. The method of claim 17, wherein the subject is human.
21. The method of claim 18, wherein the subject is human.
22. The method of claim 19, wherein the subject is human.

* * * * *

```
                              SEQUENCE LISTING

<160> NUMBER OF SEQ ID NOS: 124

<210> SEQ ID NO 1
<211> LENGTH: 15
<212> TYPE: PRT
<213> ORGANISM: Artificial Sequence
<220> FEATURE:
<223> OTHER INFORMATION: Synthetic construct

<400> SEQUENCE: 1

Ser Thr Met Met Ser Arg Ser His Lys Thr Arg Ser His His Val
1               5                   10                  15

<210> SEQ ID NO 2
<211> LENGTH: 15
<212> TYPE: PRT
<213> ORGANISM: Homo sapiens

<400> SEQUENCE: 2

Lys Leu Lys Asp Glu Asn Ser Gln Leu Lys Ser Glu Val Ser Lys
1               5                   10                  15

<210> SEQ ID NO 3
<211> LENGTH: 10
<212> TYPE: PRT
<213> ORGANISM: Homo sapiens

<400> SEQUENCE: 3

Lys Leu Lys Asp Glu Asn Ser Gln Leu Lys
1               5                   10

<210> SEQ ID NO 4
<211> LENGTH: 51
<212> TYPE: PRT
<213> ORGANISM: Homo sapiens

<400> SEQUENCE: 4

Ala Lys Gln Lys Ile Lys His Val Val Lys Leu Lys Asp Glu Asn Ser
1               5                   10                  15

Gln Leu Lys Ser Glu Val Ser Lys Leu Arg Cys Gln Leu Ala Lys Lys
            20                  25                  30

Lys Gln Ser Glu Thr Lys Leu Gln Glu Glu Leu Asn Lys Val Leu Gly
        35                  40                  45

Ile Lys His
    50

<210> SEQ ID NO 5
<211> LENGTH: 18
<212> TYPE: PRT
<213> ORGANISM: Homo sapiens

<400> SEQUENCE: 5

Lys Leu Lys Asp Glu Asn Ser Gln Leu Lys Ser Glu Val Ser Lys Leu
1               5                   10                  15

Arg Ser
```

-continued

```
<210> SEQ ID NO 6
<211> LENGTH: 7
<212> TYPE: PRT
<213> ORGANISM: Artificial Sequence
<220> FEATURE:
<223> OTHER INFORMATION: Synthetic construct

<400> SEQUENCE: 6

Lys Thr Arg Ser His His Val
1               5

<210> SEQ ID NO 7
<211> LENGTH: 6
<212> TYPE: PRT
<213> ORGANISM: Homo sapiens

<400> SEQUENCE: 7

Lys Ser Glu Val Ser Lys
1               5

<210> SEQ ID NO 8
<211> LENGTH: 7
<212> TYPE: PRT
<213> ORGANISM: Homo sapiens

<400> SEQUENCE: 8

Lys Leu Lys Asp Glu Asn Ser
1               5

<210> SEQ ID NO 9
<211> LENGTH: 8
<212> TYPE: PRT
<213> ORGANISM: Homo sapiens

<400> SEQUENCE: 9

Lys Leu Lys Asp Glu Asn Ser Gln
1               5

<210> SEQ ID NO 10
<211> LENGTH: 6
<212> TYPE: PRT
<213> ORGANISM: Artificial Sequence
<220> FEATURE:
<223> OTHER INFORMATION: Synthetic construct

<400> SEQUENCE: 10

Ser Thr Met Met Ser Arg
1               5

<210> SEQ ID NO 11
<211> LENGTH: 114
<212> TYPE: PRT
<213> ORGANISM: Mus musculus

<400> SEQUENCE: 11

Leu Asp Ala Phe Glu Ala Glu Lys Gln Ala Leu Leu Asn Glu His Gly
1               5                   10                  15

Ala Thr Gln Glu Gln Leu Asn Lys Ile Arg Asp Ser Tyr Ala Gln Leu
                20                  25                  30

Leu Gly His Gln Asn Leu Lys Gln Lys Ile Lys His Val Lys Leu
                35                  40                  45

Lys Asp Glu Asn Ser Gln Leu Lys Ser Glu Val Ser Lys Leu Arg Ser
        50                  55                  60

Gln Leu Val Lys Arg Lys Gln Asn Glu Leu Arg Leu Gln Gly Glu Leu
```

```
                65                  70                  75                  80
Asp Lys Ala Leu Gly Ile Arg His Phe Asp Pro Ser Lys Ala Phe Cys
                    85                  90                  95
His Ala Ser Lys Glu Asn Phe Thr Pro Leu Lys Glu Gly Asn Pro Asn
                100                 105                 110
Cys Cys

<210> SEQ ID NO 12
<211> LENGTH: 32
<212> TYPE: PRT
<213> ORGANISM: Mus musculus

<400> SEQUENCE: 12

Leu Lys Gln Lys Ile Lys His Val Val Lys Leu Lys Asp Glu Asn Ser
1               5                   10                  15
Gln Leu Lys Ser Glu Val Ser Lys Leu Arg Ser Gln Leu Val Lys Arg
                20                  25                  30

<210> SEQ ID NO 13
<211> LENGTH: 9
<212> TYPE: PRT
<213> ORGANISM: Homo sapiens

<400> SEQUENCE: 13

Ser Gln Leu Lys Ser Glu Val Ser Lys
1               5

<210> SEQ ID NO 14
<211> LENGTH: 7
<212> TYPE: PRT
<213> ORGANISM: Homo sapiens

<400> SEQUENCE: 14

Leu Lys Ser Glu Val Ser Lys
1               5

<210> SEQ ID NO 15
<211> LENGTH: 9
<212> TYPE: PRT
<213> ORGANISM: Artificial Sequence
<220> FEATURE:
<223> OTHER INFORMATION: Synthetic construct

<400> SEQUENCE: 15

Ser Thr Met Met Ser Arg Ser His Lys
1               5

<210> SEQ ID NO 16
<211> LENGTH: 10
<212> TYPE: PRT
<213> ORGANISM: Camelus ferus

<400> SEQUENCE: 16

Lys Leu Lys Asp Asp Asn Ser Gln Leu Lys
1               5                   10

<210> SEQ ID NO 17
<211> LENGTH: 10
<212> TYPE: PRT
<213> ORGANISM: Erinaceus europaeus

<400> SEQUENCE: 17

Lys Leu Lys Asp Glu Asn Ser Gln Leu Arg
```

```
1               5                  10
```

<210> SEQ ID NO 18
<211> LENGTH: 10
<212> TYPE: PRT
<213> ORGANISM: Chrysemys picta bellii

<400> SEQUENCE: 18

```
Lys Leu Lys Asp Glu Asn Ala Gln Leu Lys
1               5                  10
```

<210> SEQ ID NO 19
<211> LENGTH: 10
<212> TYPE: PRT
<213> ORGANISM: Ovis aries

<400> SEQUENCE: 19

```
Lys Leu Lys Asp Glu Asn Ser Asn Leu Lys
1               5                  10
```

<210> SEQ ID NO 20
<211> LENGTH: 10
<212> TYPE: PRT
<213> ORGANISM: Monodelphis domestica

<400> SEQUENCE: 20

```
Lys Leu Lys Glu Glu Asn Asn Gln Leu Lys
1               5                  10
```

<210> SEQ ID NO 21
<211> LENGTH: 10
<212> TYPE: PRT
<213> ORGANISM: Anolis carolinensis

<400> SEQUENCE: 21

```
Lys Leu Lys Glu Glu Asn Thr Gln Leu Lys
1               5                  10
```

<210> SEQ ID NO 22
<211> LENGTH: 10
<212> TYPE: PRT
<213> ORGANISM: Latimeria chalumnae

<400> SEQUENCE: 22

```
Lys Leu Lys Glu Glu Asn Ser Gln Leu Arg
1               5                  10
```

<210> SEQ ID NO 23
<211> LENGTH: 10
<212> TYPE: PRT
<213> ORGANISM: Xenopus laevis

<400> SEQUENCE: 23

```
Lys Leu Lys Thr Glu Asn Ser Glu Leu Lys
1               5                  10
```

<210> SEQ ID NO 24
<211> LENGTH: 10
<212> TYPE: PRT
<213> ORGANISM: Xenopus (Silurana) tropicalis

<400> SEQUENCE: 24

```
Lys Leu Lys Ile Glu Asn Ser Glu Leu Lys
1               5                  10
```

<210> SEQ ID NO 25
<211> LENGTH: 10
<212> TYPE: PRT
<213> ORGANISM: Haplochromis burtoni

<400> SEQUENCE: 25

Lys Leu Lys Asp Glu Asn Ile Ser Leu Lys
1               5                   10

<210> SEQ ID NO 26
<211> LENGTH: 10
<212> TYPE: PRT
<213> ORGANISM: Columba livia

<400> SEQUENCE: 26

Lys Leu Lys Glu Glu Asn Thr His Leu Lys
1               5                   10

<210> SEQ ID NO 27
<211> LENGTH: 10
<212> TYPE: PRT
<213> ORGANISM: Caenorhabditis briggsae

<400> SEQUENCE: 27

Lys Leu Lys Asn Glu Asn Lys Gln Leu Lys
1               5                   10

<210> SEQ ID NO 28
<211> LENGTH: 10
<212> TYPE: PRT
<213> ORGANISM: Alligator mississippiensis

<400> SEQUENCE: 28

Lys Leu Lys Asn Glu Asn Ile Gln Leu Lys
1               5                   10

<210> SEQ ID NO 29
<211> LENGTH: 10
<212> TYPE: PRT
<213> ORGANISM: Danio rerio

<400> SEQUENCE: 29

Lys Leu Lys Glu Glu Asn Leu Glu Leu Lys
1               5                   10

<210> SEQ ID NO 30
<211> LENGTH: 10
<212> TYPE: PRT
<213> ORGANISM: Takifugu rubripes

<400> SEQUENCE: 30

Lys Leu Lys Asp Glu Asn Thr Ser Leu Lys
1               5                   10

<210> SEQ ID NO 31
<211> LENGTH: 10
<212> TYPE: PRT
<213> ORGANISM: Lepisosteus oculatus

<400> SEQUENCE: 31

Lys Leu Lys Glu Glu Asn Phe Asn Leu Lys
1               5                   10

<210> SEQ ID NO 32

```
<211> LENGTH: 10
<212> TYPE: PRT
<213> ORGANISM: Callorhynchus milii

<400> SEQUENCE: 32

Lys Leu Lys Val Glu Asn Gly Gln Leu Lys
1               5                   10

<210> SEQ ID NO 33
<211> LENGTH: 10
<212> TYPE: PRT
<213> ORGANISM: Ciona intestinalis

<400> SEQUENCE: 33

Lys Ile Lys Glu Glu Ser Val Ala Leu Lys
1               5                   10

<210> SEQ ID NO 34
<211> LENGTH: 10
<212> TYPE: PRT
<213> ORGANISM: Tribolium castaneum

<400> SEQUENCE: 34

Lys Thr Lys Tyr Leu Glu Lys Thr Lys Lys
1               5                   10

<210> SEQ ID NO 35
<211> LENGTH: 10
<212> TYPE: PRT
<213> ORGANISM: Tetraodon migroviridis

<400> SEQUENCE: 35

Lys Leu Lys Asp Glu Asn Ser Ala Leu Lys
1               5                   10

<210> SEQ ID NO 36
<211> LENGTH: 10
<212> TYPE: PRT
<213> ORGANISM: Bacillus timonensis

<400> SEQUENCE: 36

Lys Val Lys Asp Glu Asn Ser Gln Leu Lys
1               5                   10

<210> SEQ ID NO 37
<211> LENGTH: 10
<212> TYPE: PRT
<213> ORGANISM: Desulfovibrio piezophilus

<400> SEQUENCE: 37

Lys Leu Lys Glu Glu Asn Ala Ala Leu Lys
1               5                   10

<210> SEQ ID NO 38
<211> LENGTH: 10
<212> TYPE: PRT
<213> ORGANISM: Auricularia delicata

<400> SEQUENCE: 38

Lys Leu Lys Asp Glu Asn Asp Ala Leu Lys
1               5                   10

<210> SEQ ID NO 39
<211> LENGTH: 10
<212> TYPE: PRT
```

```
<213> ORGANISM: Echinococcus multilocularis

<400> SEQUENCE: 39

Lys Leu Lys Asp Glu Gln Glu Lys Leu Lys
1               5                   10

<210> SEQ ID NO 40
<211> LENGTH: 10
<212> TYPE: PRT
<213> ORGANISM: Aminobacterium mobiler

<400> SEQUENCE: 40

Lys Leu Lys Asp Glu Asn Glu Gln Leu Lys
1               5                   10

<210> SEQ ID NO 41
<211> LENGTH: 10
<212> TYPE: PRT
<213> ORGANISM: Ichthyophthirius multifiliis

<400> SEQUENCE: 41

Lys Leu Lys Asp Glu Asn Ser Arg Leu Lys
1               5                   10

<210> SEQ ID NO 42
<211> LENGTH: 10
<212> TYPE: PRT
<213> ORGANISM: Hydra vulgaris

<400> SEQUENCE: 42

Lys Leu Lys Asn Glu Asn Arg Gln Leu Lys
1               5                   10

<210> SEQ ID NO 43
<211> LENGTH: 10
<212> TYPE: PRT
<213> ORGANISM: Angomonas deanei

<400> SEQUENCE: 43

Lys Leu Arg Asp Glu Asn Ser Thr Leu Lys
1               5                   10

<210> SEQ ID NO 44
<211> LENGTH: 10
<212> TYPE: PRT
<213> ORGANISM: Tetrahymena thermophila

<400> SEQUENCE: 44

Lys Leu Lys Ile Gln Asn Leu Glu Gly Glu
1               5                   10

<210> SEQ ID NO 45
<211> LENGTH: 11
<212> TYPE: PRT
<213> ORGANISM: Paramecium tetraurelia

<400> SEQUENCE: 45

Lys Leu Glu Asp Glu Gln Asn Ser Gln Ile Lys
1               5                   10

<210> SEQ ID NO 46
<211> LENGTH: 10
<212> TYPE: PRT
<213> ORGANISM: Selaginella moellendorffii
```

```
<400> SEQUENCE: 46

Lys Leu Lys Asp Glu Thr Ser Lys Leu Lys
1               5                   10

<210> SEQ ID NO 47
<211> LENGTH: 10
<212> TYPE: PRT
<213> ORGANISM: Alloprevotella rava

<400> SEQUENCE: 47

Lys Leu Arg Asp Glu Asn Ser Gln Leu Lys
1               5                   10

<210> SEQ ID NO 48
<211> LENGTH: 10
<212> TYPE: PRT
<213> ORGANISM: Homo sapiens

<400> SEQUENCE: 48

Lys Leu Lys Gln Glu Asn Thr Gln Leu Lys
1               5                   10

<210> SEQ ID NO 49
<211> LENGTH: 9
<212> TYPE: PRT
<213> ORGANISM: Scleropages formosus

<400> SEQUENCE: 49

Lys Leu Gln Glu Glu Asn His Gln Leu
1               5

<210> SEQ ID NO 50
<211> LENGTH: 10
<212> TYPE: PRT
<213> ORGANISM: Homo sapiens

<400> SEQUENCE: 50

Lys Leu Lys Ala Glu Asn Asp Arg Leu Lys
1               5                   10

<210> SEQ ID NO 51
<211> LENGTH: 10
<212> TYPE: PRT
<213> ORGANISM: Tupaia chinensio

<400> SEQUENCE: 51

Lys Leu Lys Asp Asp Glu Val Ala Gln Leu
1               5                   10

<210> SEQ ID NO 52
<211> LENGTH: 9
<212> TYPE: PRT
<213> ORGANISM: Colobus angolensis palliates

<400> SEQUENCE: 52

Lys Leu Val Glu Glu Thr Lys Gln Leu
1               5

<210> SEQ ID NO 53
<211> LENGTH: 9
<212> TYPE: PRT
<213> ORGANISM: Ovis aries

<400> SEQUENCE: 53
```

```
Lys Leu Gln Glu Glu Leu Asn Lys Val
1               5

<210> SEQ ID NO 54
<211> LENGTH: 8
<212> TYPE: PRT
<213> ORGANISM: Heterocephalus glaber

<400> SEQUENCE: 54

Leu Lys Asp Glu Asn Ser Lys Leu
1               5

<210> SEQ ID NO 55
<211> LENGTH: 9
<212> TYPE: PRT
<213> ORGANISM: Myotis brandtii

<400> SEQUENCE: 55

Leu Lys Asn Lys Asn Ser Gln Leu Lys
1               5

<210> SEQ ID NO 56
<211> LENGTH: 7
<212> TYPE: PRT
<213> ORGANISM: Homo sapiens

<400> SEQUENCE: 56

Leu Lys Glu Glu Asn Ser Gln
1               5

<210> SEQ ID NO 57
<211> LENGTH: 9
<212> TYPE: PRT
<213> ORGANISM: Pan troglodytes

<400> SEQUENCE: 57

Leu Lys Asp Glu Lys Ser Asn Leu Lys
1               5

<210> SEQ ID NO 58
<211> LENGTH: 9
<212> TYPE: PRT
<213> ORGANISM: Macaca fascicularis

<400> SEQUENCE: 58

Leu Lys Gly Glu Asn Glu Gln Leu Lys
1               5

<210> SEQ ID NO 59
<211> LENGTH: 9
<212> TYPE: PRT
<213> ORGANISM: Loxodonta africana

<400> SEQUENCE: 59

Lys Leu Lys Glu Glu Ile Thr Gln Leu
1               5

<210> SEQ ID NO 60
<211> LENGTH: 8
<212> TYPE: PRT
<213> ORGANISM: Homo sapiens

<400> SEQUENCE: 60

Leu Lys Ala Glu Asn Ser His Leu
1               5
```

<210> SEQ ID NO 61
<211> LENGTH: 8
<212> TYPE: PRT
<213> ORGANISM: Homo sapiens

<400> SEQUENCE: 61

Leu Lys Asp Gln Asn Ser Lys Leu
1               5

<210> SEQ ID NO 62
<211> LENGTH: 7
<212> TYPE: PRT
<213> ORGANISM: Homo sapiens

<400> SEQUENCE: 62

Lys Thr Arg Ser His Ser Val
1               5

<210> SEQ ID NO 63
<211> LENGTH: 9
<212> TYPE: PRT
<213> ORGANISM: Homo sapiens

<400> SEQUENCE: 63

Lys Thr Arg Ser His Thr Ala His Val
1               5

<210> SEQ ID NO 64
<211> LENGTH: 7
<212> TYPE: PRT
<213> ORGANISM: Rhizoctonia solani

<400> SEQUENCE: 64

Arg Thr Arg Ser His His Val
1               5

<210> SEQ ID NO 65
<211> LENGTH: 7
<212> TYPE: PRT
<213> ORGANISM: Synechococcus sp.

<400> SEQUENCE: 65

Lys Thr Lys Ser His His Val
1               5

<210> SEQ ID NO 66
<211> LENGTH: 7
<212> TYPE: PRT
<213> ORGANISM: Emiliania huxleyi

<400> SEQUENCE: 66

Lys Ala Arg Ser His His Val
1               5

<210> SEQ ID NO 67
<211> LENGTH: 7
<212> TYPE: PRT
<213> ORGANISM: Micromonas sp.

<400> SEQUENCE: 67

Lys Ser Arg Ser His His Val
1               5

<210> SEQ ID NO 68
<211> LENGTH: 7
<212> TYPE: PRT
<213> ORGANISM: Novosphingobium resinovorum

<400> SEQUENCE: 68

Lys Ile Arg Ser His His Val
1               5

<210> SEQ ID NO 69
<211> LENGTH: 7
<212> TYPE: PRT
<213> ORGANISM: Dethiosulfovibrio peptidovorans

<400> SEQUENCE: 69

Lys Asn Arg Ser His His Val
1               5

<210> SEQ ID NO 70
<211> LENGTH: 7
<212> TYPE: PRT
<213> ORGANISM: Oikopleura dioica

<400> SEQUENCE: 70

Lys Pro Arg Ser His His Val
1               5

<210> SEQ ID NO 71
<211> LENGTH: 7
<212> TYPE: PRT
<213> ORGANISM: Arabidopsis thaliana

<400> SEQUENCE: 71

Lys Thr Ser Ser His His Val
1               5

<210> SEQ ID NO 72
<211> LENGTH: 7
<212> TYPE: PRT
<213> ORGANISM: Haemophilus parainfluenzae

<400> SEQUENCE: 72

Lys Asp Arg Ser His His Val
1               5

<210> SEQ ID NO 73
<211> LENGTH: 7
<212> TYPE: PRT
<213> ORGANISM: Penicillium roqueforti

<400> SEQUENCE: 73

Lys Lys Arg Ser His His Val
1               5

<210> SEQ ID NO 74
<211> LENGTH: 7
<212> TYPE: PRT
<213> ORGANISM: Proteus penneri

<400> SEQUENCE: 74

Lys Gln Arg Ser His His Val
1               5

<210> SEQ ID NO 75
<211> LENGTH: 7

```
<212> TYPE: PRT
<213> ORGANISM: Arcticibacter svalbardensis

<400> SEQUENCE: 75

Lys Glu Arg Ser His His Val
1               5

<210> SEQ ID NO 76
<211> LENGTH: 7
<212> TYPE: PRT
<213> ORGANISM: Beauveria bassiana

<400> SEQUENCE: 76

Lys Leu Arg Ser His His Val
1               5

<210> SEQ ID NO 77
<211> LENGTH: 7
<212> TYPE: PRT
<213> ORGANISM: Eremothecium cymbalariae

<400> SEQUENCE: 77

Lys Val Arg Ser His His Val
1               5

<210> SEQ ID NO 78
<211> LENGTH: 7
<212> TYPE: PRT
<213> ORGANISM: Entamoeba invadens

<400> SEQUENCE: 78

Lys Thr Thr Ser His His Val
1               5

<210> SEQ ID NO 79
<211> LENGTH: 7
<212> TYPE: PRT
<213> ORGANISM: Gallionella capsiferriformans

<400> SEQUENCE: 79

Lys Ser Lys Ser His His Val
1               5

<210> SEQ ID NO 80
<211> LENGTH: 7
<212> TYPE: PRT
<213> ORGANISM: Mycobacterium sp.

<400> SEQUENCE: 80

Lys Thr Ala Ser His His Val
1               5

<210> SEQ ID NO 81
<211> LENGTH: 7
<212> TYPE: PRT
<213> ORGANISM: Colletotrichum gloeosporioides

<400> SEQUENCE: 81

Lys Thr Glu Ser His His Val
1               5

<210> SEQ ID NO 82
<211> LENGTH: 7
<212> TYPE: PRT
<213> ORGANISM: Pteropus alecto
```

```
<400> SEQUENCE: 82

Lys Thr Leu Ser His His Val
1               5

<210> SEQ ID NO 83
<211> LENGTH: 7
<212> TYPE: PRT
<213> ORGANISM: Bradyrhizobium sp.

<400> SEQUENCE: 83

Lys Arg Arg Ser His His Val
1               5

<210> SEQ ID NO 84
<211> LENGTH: 7
<212> TYPE: PRT
<213> ORGANISM: Bacteroides sp.

<400> SEQUENCE: 84

Lys Thr Tyr Ser His His Val
1               5

<210> SEQ ID NO 85
<211> LENGTH: 7
<212> TYPE: PRT
<213> ORGANISM: Chamaeleo calyptratus

<400> SEQUENCE: 85

Arg Thr Lys Ser His His Val
1               5

<210> SEQ ID NO 86
<211> LENGTH: 7
<212> TYPE: PRT
<213> ORGANISM: Monodelphis domestica

<400> SEQUENCE: 86

Lys Thr Arg Ser His His Ile
1               5

<210> SEQ ID NO 87
<211> LENGTH: 7
<212> TYPE: PRT
<213> ORGANISM: Paenibacillus polymyxa

<400> SEQUENCE: 87

Lys Thr Arg Ala His His Val
1               5

<210> SEQ ID NO 88
<211> LENGTH: 15
<212> TYPE: PRT
<213> ORGANISM: Artificial Sequence
<220> FEATURE:
<223> OTHER INFORMATION: Synthetic construct

<400> SEQUENCE: 88

Ser Thr Met Met Ser Arg Ser His Lys Thr Arg Ser Cys His His
1               5                   10                  15

<210> SEQ ID NO 89
<211> LENGTH: 8
<212> TYPE: PRT
<213> ORGANISM: Artificial Sequence
```

```
<220> FEATURE:
<223> OTHER INFORMATION: Synthetic construct

<400> SEQUENCE: 89

Lys Leu Arg Ser Gln Leu Val Lys
1               5

<210> SEQ ID NO 90
<211> LENGTH: 10
<212> TYPE: PRT
<213> ORGANISM: Artificial Sequence
<220> FEATURE:
<223> OTHER INFORMATION: Synthetic construct

<400> SEQUENCE: 90

Ala Leu Lys Asp Glu Asn Ser Gln Leu Lys
1               5                   10

<210> SEQ ID NO 91
<211> LENGTH: 10
<212> TYPE: PRT
<213> ORGANISM: Artificial Sequence
<220> FEATURE:
<223> OTHER INFORMATION: Synthetic construct

<400> SEQUENCE: 91

Lys Leu Ala Asp Glu Asn Ser Gln Leu Lys
1               5                   10

<210> SEQ ID NO 92
<211> LENGTH: 10
<212> TYPE: PRT
<213> ORGANISM: Artificial Sequence
<220> FEATURE:
<223> OTHER INFORMATION: Synthetic construct

<400> SEQUENCE: 92

Lys Ile Lys Asp Glu Asn Ser Gln Leu Lys
1               5                   10

<210> SEQ ID NO 93
<211> LENGTH: 10
<212> TYPE: PRT
<213> ORGANISM: Artificial Sequence
<220> FEATURE:
<223> OTHER INFORMATION: Synthetic construct

<400> SEQUENCE: 93

Lys Thr Lys Asp Glu Asn Ser Gln Leu Lys
1               5                   10

<210> SEQ ID NO 94
<211> LENGTH: 10
<212> TYPE: PRT
<213> ORGANISM: Artificial Sequence
<220> FEATURE:
<223> OTHER INFORMATION: Synthetic construct

<400> SEQUENCE: 94

Lys Leu Lys Asp Glu Asn Thr Gln Leu Lys
1               5                   10

<210> SEQ ID NO 95
<211> LENGTH: 10
<212> TYPE: PRT
<213> ORGANISM: Artificial Sequence
<220> FEATURE:
```

```
<223> OTHER INFORMATION: Synthetic construct

<400> SEQUENCE: 95

Lys Leu Lys Thr Glu Asn Ser Gln Leu Lys
1               5                   10

<210> SEQ ID NO 96
<211> LENGTH: 10
<212> TYPE: PRT
<213> ORGANISM: Artificial Sequence
<220> FEATURE:
<223> OTHER INFORMATION: Synthetic construct

<400> SEQUENCE: 96

Lys Leu Lys Asp Glu Asn Ser Gln Lys Lys
1               5                   10

<210> SEQ ID NO 97
<211> LENGTH: 10
<212> TYPE: PRT
<213> ORGANISM: Artificial Sequence
<220> FEATURE:
<223> OTHER INFORMATION: Synthetic construct

<400> SEQUENCE: 97

Ala Leu Lys Asp Glu Asn Ser Gln Leu Arg
1               5                   10

<210> SEQ ID NO 98
<211> LENGTH: 10
<212> TYPE: PRT
<213> ORGANISM: Artificial Sequence
<220> FEATURE:
<223> OTHER INFORMATION: Synthetic construct

<400> SEQUENCE: 98

Lys Ala Lys Asp Glu Asn Ser Gln Leu Arg
1               5                   10

<210> SEQ ID NO 99
<211> LENGTH: 10
<212> TYPE: PRT
<213> ORGANISM: Artificial Sequence
<220> FEATURE:
<223> OTHER INFORMATION: Synthetic construct

<400> SEQUENCE: 99

Lys Leu Ala Asp Glu Asn Ser Gln Leu Arg
1               5                   10

<210> SEQ ID NO 100
<211> LENGTH: 10
<212> TYPE: PRT
<213> ORGANISM: Artificial Sequence
<220> FEATURE:
<223> OTHER INFORMATION: Synthetic construct

<400> SEQUENCE: 100

Lys Leu Lys Ala Glu Asn Ser Gln Leu Arg
1               5                   10

<210> SEQ ID NO 101
<211> LENGTH: 10
<212> TYPE: PRT
<213> ORGANISM: Artificial Sequence
<220> FEATURE:
<223> OTHER INFORMATION: Synthetic construct
```

```
<400> SEQUENCE: 101

Lys Leu Lys Asp Ala Asn Ser Gln Leu Arg
1               5                   10

<210> SEQ ID NO 102
<211> LENGTH: 10
<212> TYPE: PRT
<213> ORGANISM: Artificial Sequence
<220> FEATURE:
<223> OTHER INFORMATION: Synthetic construct

<400> SEQUENCE: 102

Lys Leu Lys Asp Glu Ala Ser Gln Leu Arg
1               5                   10

<210> SEQ ID NO 103
<211> LENGTH: 10
<212> TYPE: PRT
<213> ORGANISM: Artificial Sequence
<220> FEATURE:
<223> OTHER INFORMATION: Synthetic construct

<400> SEQUENCE: 103

Lys Leu Lys Asp Glu Asn Ala Gln Leu Arg
1               5                   10

<210> SEQ ID NO 104
<211> LENGTH: 10
<212> TYPE: PRT
<213> ORGANISM: Artificial Sequence
<220> FEATURE:
<223> OTHER INFORMATION: Synthetic construct

<400> SEQUENCE: 104

Lys Leu Lys Asp Glu Asn Ser Ala Leu Arg
1               5                   10

<210> SEQ ID NO 105
<211> LENGTH: 10
<212> TYPE: PRT
<213> ORGANISM: Artificial Sequence
<220> FEATURE:
<223> OTHER INFORMATION: Synthetic construct

<400> SEQUENCE: 105

Lys Leu Lys Asp Glu Asn Ser Gln Ala Arg
1               5                   10

<210> SEQ ID NO 106
<211> LENGTH: 10
<212> TYPE: PRT
<213> ORGANISM: Artificial Sequence
<220> FEATURE:
<223> OTHER INFORMATION: Synthetic construct

<400> SEQUENCE: 106

Lys Leu Lys Asp Glu Asn Ser Gln Leu Ala
1               5                   10

<210> SEQ ID NO 107
<211> LENGTH: 10
<212> TYPE: PRT
<213> ORGANISM: Artificial Sequence
<220> FEATURE:
<223> OTHER INFORMATION: Synthetic construct
```

```
<400> SEQUENCE: 107

Lys Leu Lys Thr Glu Asn Ser Gln Leu Arg
1               5                   10

<210> SEQ ID NO 108
<211> LENGTH: 7
<212> TYPE: PRT
<213> ORGANISM: Artificial Sequence
<220> FEATURE:
<223> OTHER INFORMATION: Synthetic construct

<400> SEQUENCE: 108

Lys Thr Arg Ser Ala His Val
1               5

<210> SEQ ID NO 109
<211> LENGTH: 7
<212> TYPE: PRT
<213> ORGANISM: Artificial Sequence
<220> FEATURE:
<223> OTHER INFORMATION: Synthetic construct

<400> SEQUENCE: 109

Lys Thr Arg Ser His Ala Val
1               5

<210> SEQ ID NO 110
<211> LENGTH: 7
<212> TYPE: PRT
<213> ORGANISM: Artificial Sequence
<220> FEATURE:
<223> OTHER INFORMATION: Synthetic construct

<400> SEQUENCE: 110

Lys Thr Arg Ser His His Gln
1               5

<210> SEQ ID NO 111
<211> LENGTH: 8
<212> TYPE: PRT
<213> ORGANISM: Artificial Sequence
<220> FEATURE:
<223> OTHER INFORMATION: Synthetic construct

<400> SEQUENCE: 111

Lys Thr Arg Ser Cys His His Val
1               5

<210> SEQ ID NO 112
<211> LENGTH: 8
<212> TYPE: PRT
<213> ORGANISM: Artificial Sequence
<220> FEATURE:
<223> OTHER INFORMATION: Synthetic construct

<400> SEQUENCE: 112

His Lys Thr Arg Ser His His Val
1               5

<210> SEQ ID NO 113
<211> LENGTH: 9
<212> TYPE: PRT
<213> ORGANISM: Artificial Sequence
<220> FEATURE:
<223> OTHER INFORMATION: Synthetic construct

<400> SEQUENCE: 113
```

```
Ser His Lys Thr Arg Ser His His Val
1               5

<210> SEQ ID NO 114
<211> LENGTH: 10
<212> TYPE: PRT
<213> ORGANISM: Artificial Sequence
<220> FEATURE:
<223> OTHER INFORMATION: Synthetic construct

<400> SEQUENCE: 114

Arg Ser His Lys Thr Arg Ser His His Val
1               5                   10

<210> SEQ ID NO 115
<211> LENGTH: 11
<212> TYPE: PRT
<213> ORGANISM: Artificial Sequence
<220> FEATURE:
<223> OTHER INFORMATION: Synthetic construct

<400> SEQUENCE: 115

Ser Arg Ser His Lys Thr Arg Ser His His Val
1               5                   10

<210> SEQ ID NO 116
<211> LENGTH: 12
<212> TYPE: PRT
<213> ORGANISM: Artificial Sequence
<220> FEATURE:
<223> OTHER INFORMATION: Synthetic construct

<400> SEQUENCE: 116

Met Ser Arg Ser His Lys Thr Arg Ser His His Val
1               5                   10

<210> SEQ ID NO 117
<211> LENGTH: 13
<212> TYPE: PRT
<213> ORGANISM: Artificial Sequence
<220> FEATURE:
<223> OTHER INFORMATION: Synthetic construct

<400> SEQUENCE: 117

Met Met Ser Arg Ser His Lys Thr Arg Ser His His Val
1               5                   10

<210> SEQ ID NO 118
<211> LENGTH: 14
<212> TYPE: PRT
<213> ORGANISM: Artificial Sequence
<220> FEATURE:
<223> OTHER INFORMATION: Synthetic construct

<400> SEQUENCE: 118

Thr Met Met Ser Arg Ser His Lys Thr Arg Ser His His Val
1               5                   10

<210> SEQ ID NO 119
<211> LENGTH: 9
<212> TYPE: PRT
<213> ORGANISM: Homo sapiens

<400> SEQUENCE: 119

Lys Leu Lys Asp Glu Asn Ser Gln Leu
1               5
```

```
<210> SEQ ID NO 120
<211> LENGTH: 8
<212> TYPE: PRT
<213> ORGANISM: Homo sapiens

<400> SEQUENCE: 120

Lys Leu Lys Asp Glu Asn Ser Gln
1               5

<210> SEQ ID NO 121
<211> LENGTH: 11
<212> TYPE: PRT
<213> ORGANISM: Homo sapiens

<400> SEQUENCE: 121

Lys Leu Lys Asp Glu Asn Ser Gln Leu Lys Ser
1               5                   10

<210> SEQ ID NO 122
<211> LENGTH: 12
<212> TYPE: PRT
<213> ORGANISM: Homo sapiens

<400> SEQUENCE: 122

Lys Leu Lys Asp Glu Asn Ser Gln Leu Lys Ser Glu
1               5                   10

<210> SEQ ID NO 123
<211> LENGTH: 13
<212> TYPE: PRT
<213> ORGANISM: Homo sapiens

<400> SEQUENCE: 123

Lys Leu Lys Asp Glu Asn Ser Gln Leu Lys Ser Glu Val
1               5                   10

<210> SEQ ID NO 124
<211> LENGTH: 14
<212> TYPE: PRT
<213> ORGANISM: Homo sapiens

<400> SEQUENCE: 124

Lys Leu Lys Asp Glu Asn Ser Gln Leu Lys Ser Glu Val Ser
1               5                   10
```